(12) United States Patent
Klaus et al.

(10) Patent No.: US 9,446,064 B2
(45) Date of Patent: Sep. 20, 2016

(54) COMBINATION THERAPY FOR TREATING CANCER

(71) Applicant: Epizyme, Inc., Cambridge, MA (US)

(72) Inventors: Christine Klaus, Waban, MA (US); Maria Alejandra Raimondi, Jamaica Plain, MA (US); Scott R. Daigle, Newburyport, MA (US); Roy MacFarlane Pollock, Medford, MA (US)

(73) Assignee: Epizyme, Inc., Cambridge, MA (US)

( * ) Notice: Subject to any disclaimer, the term of this patent is extended or adjusted under 35 U.S.C. 154(b) by 62 days.

(21) Appl. No.: 14/210,511

(22) Filed: Mar. 14, 2014

(65) Prior Publication Data

US 2014/0323421 A1    Oct. 30, 2014

Related U.S. Application Data

(60) Provisional application No. 61/785,446, filed on Mar. 14, 2013.

(51) Int. Cl.

| | |
|---|---|
| *A61K 31/7076* | (2006.01) |
| *A61K 31/704* | (2006.01) |
| *A61K 31/706* | (2006.01) |
| *A61K 31/136* | (2006.01) |
| *A61K 31/4745* | (2006.01) |
| *A61K 31/7068* | (2006.01) |
| *A61K 31/135* | (2006.01) |
| *A61K 31/5377* | (2006.01) |

(52) U.S. Cl.
CPC .......... *A61K 31/7076* (2013.01); *A61K 31/135* (2013.01); *A61K 31/136* (2013.01); *A61K 31/4745* (2013.01); *A61K 31/5377* (2013.01); *A61K 31/704* (2013.01); *A61K 31/706* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 8,580,762 B2 * | 11/2013 | Olhava | C07D 487/04 514/46 |
| 8,722,877 B2 | 5/2014 | Chesworth et al. | |
| 9,029,343 B2 | 5/2015 | Chesworth et al. | |
| 9,096,634 B2 * | 8/2015 | Olhava | C07D 487/04 |
| 9,145,438 B2 | 9/2015 | Chesworth et al. | |
| 2004/0127453 A1 | 7/2004 | Lyons et al. | |
| 2008/0108559 A1 | 5/2008 | DiMatino | |
| 2012/0142625 A1 * | 6/2012 | Olhava | C07D 487/04 514/46 |
| 2013/0338173 A1 | 12/2013 | Olhava et al. | |
| 2015/0216890 A1 | 8/2015 | Olhava et al. | |
| 2015/0284422 A1 | 10/2015 | Olhava et al. | |
| 2015/0366893 A1 | 12/2015 | Olhava et al. | |
| 2016/0045531 A1 | 2/2016 | Klaus et al. | |

FOREIGN PATENT DOCUMENTS

| | | |
|---|---|---|
| WO | WO 2004/026319 A2 | 4/2004 |
| WO | WO 2009/126537 A1 | 10/2009 |
| WO | WO 2012/075492 A2 | 6/2012 |
| WO | WO 2012/075500 A2 | 6/2012 |
| WO | WO 2016/025635 A2 | 2/2016 |

OTHER PUBLICATIONS

Perna et al., "Depletion of L3MBTL 1 promotes the erythroid differentiation of human hematopoietic progenitor cells: possible role in 20q-polycythemia vera", *Blood*, 2010, vol. 116, No. 15, pp. 2812-2821.

* cited by examiner

*Primary Examiner* — Traviss C McIntosh, III
(74) *Attorney, Agent, or Firm* — Cooley LLP; Heidi A. Erlacher; Lian Ouyang

(57) ABSTRACT

The present invention relates to compositions comprising inhibitors of human histone methyltransferase DOT1L and one or more therapeutic agents, particularly anticancer agents, and methods of combination therapy for administering to subjects in need thereof for the treatment of cancer.

23 Claims, 18 Drawing Sheets

MOLM-13 7 Day Cotreatment
Compound A2 and Hypomethylating Agents

A

Decitabine

| CI For experimental values | | | |
|---|---|---|---|
| Cpd A2 (nM) | Decitabine (nM) | Fa | CI |
| 39.0625 | 0.625 | 0.21279 | 1.325 |
| 78.125 | 1.25 | 0.30262 | 1.685 |
| 156.25 | 2.5 | 0.68447 | 0.828 |
| 312.5 | 5 | 0.88664 | 0.643 |
| 625 | 10 | 0.98902 | 0.298 |
| 1250 | 20 | 0.99988 | 0.063 |

B

Vidaza

| CI For experimental values | | | |
|---|---|---|---|
| Cpd A2 (nM) | Vidaza (nM) | Fa | CI |
| 39.0625 | 39.0625 | 0.23317 | 0.799 |
| 78.125 | 78.125 | 0.4212 | 0.712 |
| 156.25 | 156.25 | 0.56659 | 0.832 |
| 312.5 | 312.5 | 0.79715 | 0.617 |
| 625 | 625 | 0.94892 | 0.316 |
| 1250 | 1250 | 0.99438 | 0.095 |
| 2500 | 2500 | 0.99932 | 0.035 |

MV4-11 Combination Study
Compound A2 with Daunorubicin

A

4 Day Pretreatment + 3 Day Cotreatment

| CI For experimental values | | |
|---|---|---|
| Cpd A2 (nM) | Daunorubicin (nM) | |
| | | CI |
| 7.8125 | 0.78125 | 1.732 |
| 15.625 | 1.5625 | 1.135 |
| 31.25 | 3.125 | 0.629 |
| 62.5 | 6.25 | 0.267 |
| 125 | 12.5 | 0.144 |
| 250 | 25 | 0.050 |
| 500 | 50 | 0.029 |

B

7 Day Cotreatment

| CI For experimental values | | | |
|---|---|---|---|
| Cpd A2 (nM) | Daunorubicin (nM) | Fa | CI |
| 15.625 | 0.15625 | 0.57409 | 1.728 |
| 31.25 | 0.3125 | 0.86298 | 0.617 |
| 62.5 | 0.625 | 0.92861 | 0.642 |
| 125 | 1.25 | 0.98462 | 0.430 |

MV411 Combination Studies
Compound A2 and IBET-151

A

4 Day Pretreatment + 3 Day Cotreatment n=1

| CI For experimental values | | | |
|---|---|---|---|
| Cpd A2 (B) (nM) | IBET151 (nM) | Fa | CI |
| 15.625 | 156.25 | 0.42109 | 0.962 |
| 31.25 | 312.5 | 0.69894 | 0.769 |
| 62.5 | 625 | 0.92906 | 0.484 |
| 125 | 1250 | 0.9917 | 0.262 |
| 250 | 2500 | 0.9999 | 0.044 |
| 500 | 5000 | 0.99993 | 0.072 |

B

7 Day Cotreatment

| CI For experimental values | | | |
|---|---|---|---|
| Cpd A2 (nM) | IBET (nM) | Fa | CI |
| 15.625 | 15.625 | | 2.566 |
| 31.25 | 31.25 | 0.14481 | 0.975 |
| 62.5 | 62.5 | 0.44397 | 0.542 |
| 125 | 125 | 0.77494 | 0.378 |
| 250 | 250 | 0.95944 | 0.402 |
| | | 0.99411 | |

7 Day Cotreatment
Compound A2 with Tranylcypromine

A

MOLM-13
Tranylcypromine n=1

CI For experimental values

| Cpd A2 (nM) | TCP (nM) | Fa | CI |
|---|---|---|---|
| 50 | 625 | 0.23074 | 1.027 |
| 100 | 1250 | 0.37066 | 1.048 |
| 200 | 2500 | 0.60495 | 0.810 |
| 400 | 5000 | 0.86155 | 0.401 |
| 800 | 10000 | 0.95058 | 0.261 |
| 1600 | 20000 | 0.99309 | 0.071 |

B

MV4-11
Tranylcypromine

CI For experimental values

| Cpd A2 (nM) | Tranylcypromine (nM) | Fa | CI |
|---|---|---|---|
| 2.5 | 2500 | 0.25998 | 0.992 |
| 5 | 5000 | 0.45472 | 0.868 |
| 10 | 10000 | 0.72128 | 0.609 |
| 20 | 20000 | 0.86342 | 0.549 |
| 40 | 40000 | 0.95014 | 0.427 |

COMBINATION THERAPY FOR TREATING CANCER

RELATED APPLICATIONS

This application claims priority to, and the benefit of U.S. Provisional Application No. 61/785,446, field Mar. 14, 2013, the entire contents of which are incorporated herein by reference in their entireties.

FIELD OF INVENTION

This invention relates to compositions comprising inhibitors of human histone methyltransferase DOT1L and one or more other therapeutic agents, particularly anticancer agents, and methods of combination therapy for treating cancer.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., DOT1L), many of which are associated with specific genetic alterations that can cause human disease.

Disease-associated chromatin-modifying enzymes (e.g., DOT1L) play a role in diseases such as proliferative disorders, metabolic disorders, and blood disorders. Thus, there is a need for the development of compositions that are capable of modulating the activity of DOT1L.

SUMMARY OF THE INVENTION

In one aspect, this present invention features a composition comprising a compound of Formula (I):
or pharmaceutically acceptable salts thereof, and one or more therapeutic agents,
wherein,
T is a linker group of a 6-10 carbon atoms, in which one or more carbon atoms are optionally replaced with a heteroatom and T is optionally substituted;
$R_9$ comprises a $C_6$-$C_{10}$ aryl or 5 to 10-membered heteroaryl optionally substituted with one or more substituents selected from the group consisting of unsubstituted or substituted t-butyl, $CF_3$, cyclohexyl, $C_6$-$C_{10}$ aryl, and 5 to 10-membered heteroaryl;
A is O or $CH_2$;
each of G and J, independently, is H, halo, C(O)OH, C(O)O—$C_1$-$C_6$ alkyl or $OR_a$, $R_a$ being H, $C_1$-$C_6$ alkyl, C(O)—$C_1$-$C_6$ alkyl, or silyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;
each X independently is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
each of $R_1$ and $R_2$, independently is H, halo, hydroxyl, carboxyl, cyano, or $R_{S2}$, $R_{S2}$ being amino, $C_1$-$C_6$ alkoxyl, $C_1$-$C_6$ alkyl, $C_2$-$C_6$ alkenyl, $C_2$-$C_6$ alkynyl, or $C_3$-$C_8$ cycloalkyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl; and
Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl.

In some embodiments, the compound has formula (IV):

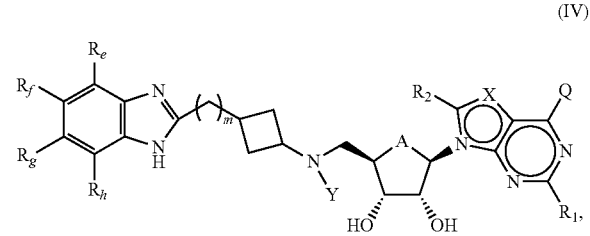

(IV)

wherein each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or $N(R_t)$, $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_r$, and $R_{S4}$ being optionally substituted with one or more substituents selected from halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, and m is 0, 1, or 2.

In one aspect, the present invention provides a composition comprising any one of the compounds listed in Tables 1-4 or pharmaceutically acceptable salts thereof and one or more therapeutic agents.

In one aspect, the present invention provides a composition comprising Compound A2:

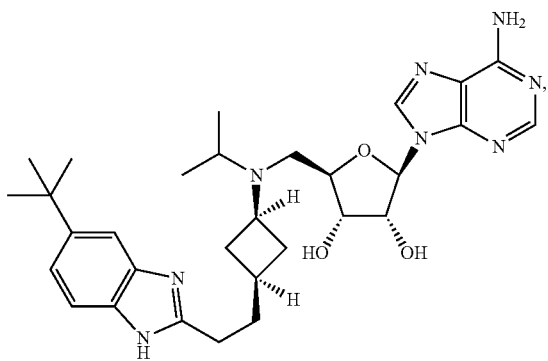 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

or pharmaceutically acceptable salts thereof, and one or more therapeutic agents.

In one aspect, the present invention provides a composition comprising Compound D16:

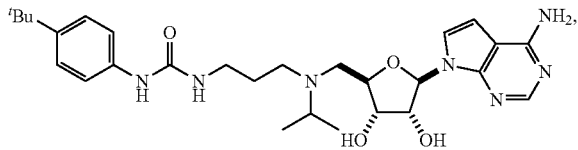 [SMILES: CC(C)N(CCCNC(=O)Nc1ccc(C(C)(C)C)cc1)C[C@H]1O[C@@H](n2ccc3c(N)ncnc32)[C@H](O)[C@@H]1O]

or pharmaceutically acceptable salts thereof, and one or more therapeutic agents.

In some embodiments, the one or more therapeutic agents are anti-cancer agents. The one or more therapeutic agents can be selected from Ara-C, Daunorubicin, Decitabine, Vidaza, Mitoxantrone, JQ1, IBET151, Panobinostat, Vorinostat, Quizartinib, Midostaurin, Tranylcypromine, LSD1 inhibitor II, Navitoclax, and analogs, derivatives, or combinations thereof. Preferably, the therapeutic agent is Ara-C or Daunorubicin, or an analog or derivative thereof.

In one aspect, the present invention provides a pharmaceutical composition comprising a therapeutically effective amount of any composition described herein and a pharmaceutically acceptable carrier.

In one aspect, the present invention provides a method of treating or alleviating a symptom of a disease by administering to a subject in need thereof a therapeutically effective amount of a composition described herein. The disease is cancer or a precancerous condition. Alternatively, the disease can be influenced by modulating the methylation status of histones or other proteins. The methylation status is mediated at least in part by the activity of DOT1L.

In one aspect, the present invention provides a method of treating or alleviating a symptom of cancer by administering to a subject in need thereof a therapeutically effective dose of a compound of Formula (I) and one or more therapeutic agents, where a compound of Formula (I) and the one or more therapeutic agents are administered simultaneously or sequentially. Alternatively, a compound of Formula (I) is administered prior to administration of the one or more therapeutic agents.

In one aspect, the present invention provides a method of treating or alleviating a symptom of cancer by administering to a subject in need thereof a therapeutically effective dose of a compound of Formula (I), or a pharmaceutically acceptable salt thereof, prior to administering a therapeutically effective dose of a composition described herein.

In some embodiments, the composition described herein is administered to the subject in need thereof at a dosage of 0.01 mg/kg per day to about 1000 mg/kg per day.

In some embodiments, the compound of Formula (I) is administered at a dosage of 0.01 mg/kg per day to about 1000 mg/kg per day.

In some embodiments, each of the one or more therapeutic agents is administered at a dosage of 0.01 mg/kg per day to about 1000 mg/kg per day.

In some embodiments, the subject has demonstrated resistance to any one of the components of the composition of claim 1 when administered as a single agent.

In one aspect, the present invention provides a method of inhibiting cancer cell proliferation by contacting a cancer cell with a composition described herein.

In one aspect, the present invention provides a method of inhibiting cancer cell proliferation by contacting a cancer cell with a compound of Formula (I) and one or more therapeutic agents, where the compound of Formula (I) and the therapeutic agents are delivered simultaneously or sequentially. Alternatively, a compound of Formula (I) is administered/delivered prior to administration of the therapeutic agents.

In one aspect, the present invention provides a method of inhibiting cancer cell proliferation by contacting a cancer cell a therapeutically effective dose of a compound of Formula (I), or a pharmaceutically acceptable salt thereof, prior to administering/contacting a therapeutically effective dose of a composition described herein.

In any methods described herein, the therapeutic agent may be Ara-C or Daunorubicin, or an analog or derivative thereof.

The subject may have leukemia. The leukemia may be characterized by a chromosomal rearrangement. The chromosomal rearrangement is chimeric fusion of mixed lineage leukemia gene (MLL) or partial tandem duplication of MLL (MLL-PTD).

The subject may have an increased level of HOXA9, Fms-like tyrosine kinase 3 (FLT3), MEIS1, and/or DOT1L.

In any methods described herein, the compound may be Compound A2 or Compound D16.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

Figure 1:
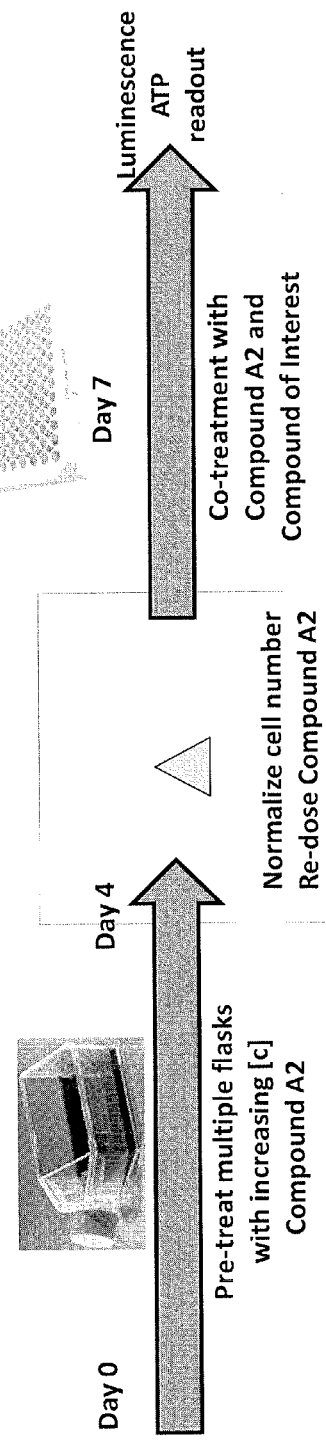
FIG. 1 is a diagram showing the overall experimental design and data analysis.
Figure 1:
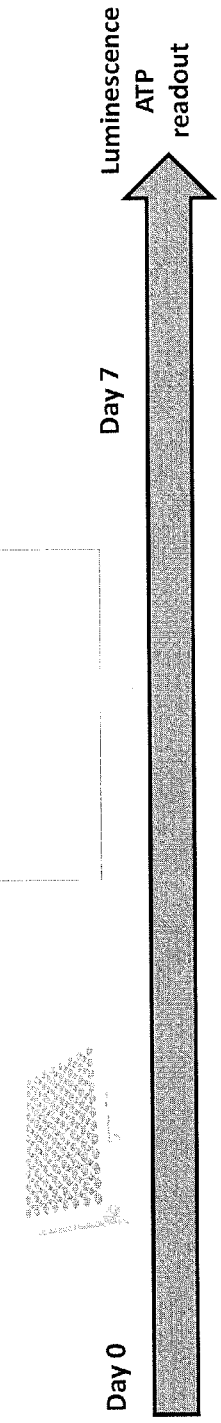

The present invention is based upon the surprising discovery that DOT1L histone methyltransferase inhibitors and anti-cancer agents can be used in combination to treat tumors with superior results than those achieved by treating tumors with DOT1L histone methyltransferase inhibitors alone or anti-cancer agents alone.

Accordingly, the present invention provides a composition comprising a DOT1L histone methyltransferase inhibitor and one or more therapeutic agents, and methods for their use to treat diseases the course of which can be influenced by modulating the methylation status of histones or other proteins, e.g., cancer. In particular, the present invention features a composition comprising Formula (I) and Ara-C or Daunorubicin.

The present invention also includes methods for combination therapies comprising DOT1L histone methyltransferase inhibitor and one or more therapeutic agents, such as a compound of Formula (I) and Ara-C or Daunorubicin, to treat cancer, e.g., leukemia. Specifically, the methods of the present invention are useful for treating or inhibiting cancer cell proliferation.

The present invention further provides uses of any composition described herein in the manufacture of medicament for treating diseases. Such diseases include, for example, cancer, a precancerous condition, or a disease influenced by modulating the methylation status of histones or other proteins.

Any compounds (e.g., DOT1L inhibitor) disclosed herein can be used for the compositions or combination therapy of the invention.

In one aspect, a composition of the invention comprises a compound of Formula (I) or a pharmaceutically acceptable salt thereof, and one or more therapeutic agents. The compounds of Formula (I) are suitable for administration as part of a combination therapy with one or more therapeutic agents or treatment modality, suitable to be administered together, sequentially, or in alternation.

The invention provides the compounds of Formula (I):

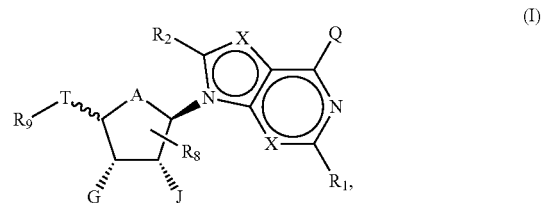

or a pharmaceutically acceptable salt or ester thereof, wherein,

T is a linker group of a 6-10 carbon atoms, in which one or more carbon atoms are optionally replaced with a heteroatom and T is optionally substituted;

$R_9$ comprises a $C_6$-$C_{10}$ aryl or 5 to 10-membered heteroaryl optionally substituted with one or more substituents selected from the group consisting of unsubstituted or substituted t-butyl, $CF_3$, cyclohexyl, $C_6$-$C_{10}$ aryl, and 5 to 10-membered heteroaryl;

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl, C(O)—$C_1$-$C_6$ alkyl, or silyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

each X independently is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_1$ and $R_2$, independently is H, halo, hydroxyl, carboxyl, cyano, or $R_{S2}$, $R_{S2}$ being amino, $C_1$-$C_6$ alkoxyl, $C_1$-$C_6$ alkyl, $C_2$-$C_6$ alkenyl, $C_2$-$C_6$ alkynyl, or $C_3$-$C_8$ cycloalkyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl; and Q is H, $NH_2$, $NHR_b$, $NR_bR_c$, $R_b$, =O, OH, or $OR_b$, in which each of $R_b$ and $R_c$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$ and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl.

For example, in Formula (I), $R_9$ is selected from the group consisting of

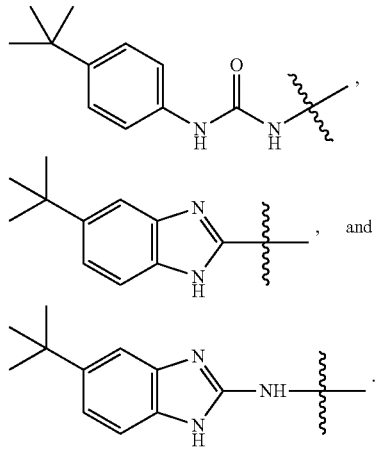

and

For example, in Formula (I), T is —$CH_2$-$L_1$-$L_2$-$L_3$-, with $L_3$ connected to $R_9$, wherein:

$L_1$ is N(Y), S, SO, or $SO_2$;

$L_2$ is CO or absent when $L_1$ is N(Y), or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, carboxyl, cyano, $C_1$-$C_6$ alkoxyl, $C_1$-$C_6$ alkylsulfonyl, $C_3$-$C_8$ cycloalkyl, $C_6$-$C_{10}$ aryl, 4 to 8-membered heterocycloalkyl, 5 to 6-membered heteroaryl, $OR_{d'}$, $OCOR_{d'}$, and $N(R_{d'})_2$, and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl; each $R_{d'}$ independently being H, $C_1$-$C_6$ alkyl, silyl, $C_1$-$C_6$ alkyl-$C_3$-$C_8$ cycloalkyl, $C_6$-$C_{10}$ aryl, 5 to 6-membered heteroaryl, aralkyl, or heteroaralkyl;

$L_3$ is —$(CR_4R_5)_n(CR_6R_7)_m$— or —$(CR_4R_5)_n$-unsubstituted or substituted $C_3$-$C_8$ cycloalkyl-$(CR_6R_7)_m$—, with $(CR_6R_7)_m$ connected to $R_9$;

each of $R_4$, $R_5$, $R_6$, and $R_7$, independently, is H, halo, hydroxyl, carboxyl, cyano, or $R_{S2}$; $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl; or two geminal $R_4$ and $R_5$ or two geminal $R_6$ and $R_7$ taken together are ethylene, propylene or butylene;

m is 0, 1, or 2; and n is 0, 1, or 2.

For example, in Formula (I) R$_9$ is

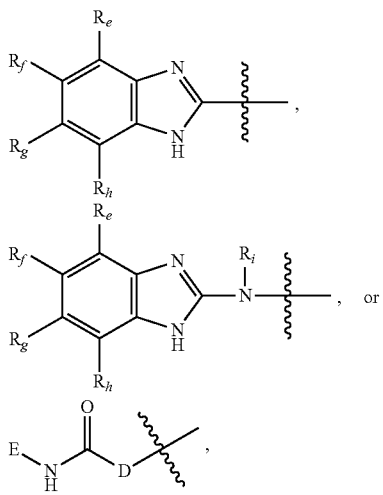

in which:
each of R$_e$, R$_f$, R$_g$, and R$_h$, independently is -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl, R$_t$ is H or C$_1$-C$_6$ alkyl optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl, D is O, NR$_j$, or CR$_j$R$_k$, each of R$_j$ and R$_k$ independently being H or C$_1$-C$_6$ alkyl, or R$_j$ and R$_k$ taken together, with the carbon atom to which they are attached, form a C$_3$-C$_{10}$ cycloalkyl ring, and E is -M$_3$ being a bond or C$_1$-C$_6$ alkyl linker optionally substituted with halo or cyano, T$_3$ being C$_3$-C$_{14}$ carbocycle or 4 to 14-membered heterocycle, and T$_3$ being optionally substituted with one or more substituents selected from the group consisting of halo, hydroxyl, thiol, carboxyl, cyano, nitro, C$_1$-C$_6$ alkyl, C$_2$-C$_6$ alkenyl, C$_2$-C$_6$ alkynyl, C$_1$-C$_6$ alkoxyl, C$_1$-C$_6$ haloalkyl, C$_1$-C$_6$ haloalkoxyl, C$_1$-C$_6$ alkylthio, C$_1$-C$_6$ alkylsulfonyl, C$_1$-C$_6$ haloalkylsulfonyl, C$_1$-C$_6$ alkylcarbonyl, C$_1$-C$_6$ alkoxycarbonyl, oxo, amino, mono-C$_1$-C$_6$ alkylamino, di-C$_1$-C$_6$ alkylamino, C$_3$-C$_8$ cycloalkyl, C$_4$-C$_{12}$ alkylcycloalkyl, C$_6$-C$_{10}$ aryl, C$_6$-C$_{10}$ aryloxyl, C$_7$-C$_{14}$ alkylaryl, C$_6$-C$_{10}$ aminoaryloxyl, C$_6$-C$_{10}$ arylthio, 4 to 6-membered heterocycloalkyl optionally substituted with halo, C$_1$-C$_4$ alkyl, C$_1$-C$_4$ haloalkyl, 5 to 6-membered heteroaryl optionally substituted with halo, C$_1$-C$_4$ alkyl, and C$_1$-C$_6$ alkyl that is substituted with hydroxy, halo, C$_1$-C$_6$ alkoxycarbonyl, C$_3$-C$_8$ cycloalkyl, C$_6$-C$_{10}$ aryl, 4 to 6-membered heterocycloalkyl, or 5 to 6-membered heteroaryl optionally further substituted with halo, hydroxyl, or C$_1$-C$_6$ alkoxyl.

For example, the compound of Formula (I) is of formula (IIa) or (IIb):

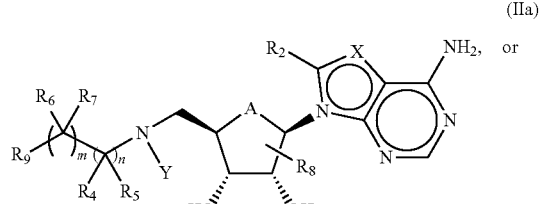

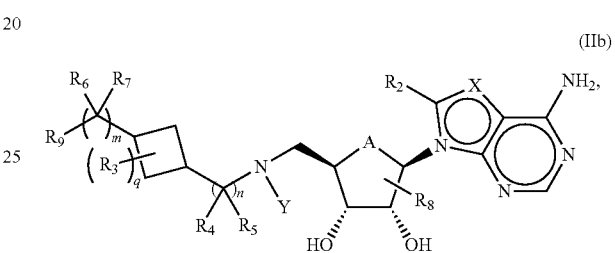

wherein R$_3$ is H, halo, hydroxyl, carboxyl, cyano, or R$_{S2}$, and q is 0, 1, 2, 3, or 4.

For example, the compound is of formula (IIa) and R$_9$ is

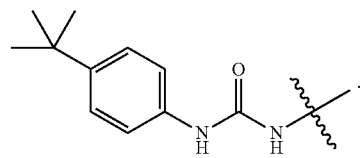 [SMILES: *NC(=O)Nc1ccc(C(C)(C)C)cc1]

For example, the compound is of formula (IIb) and R$_9$ is

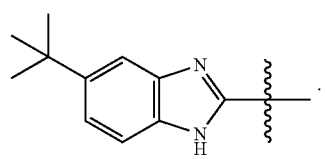 [SMILES: *c1nc2cc(C(C)(C)C)ccc2[nH]1]

Compounds of Formula (I) also include those of Formula (IIIa) or (IIIb)

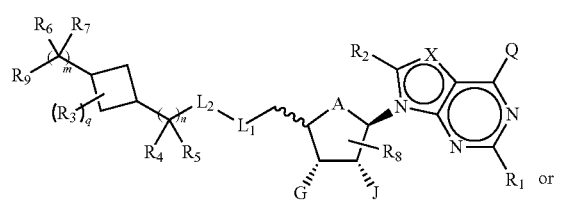

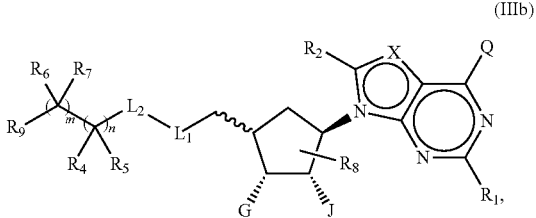

(IIIb)

or a pharmaceutically acceptable salt or ester thereof, wherein:

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

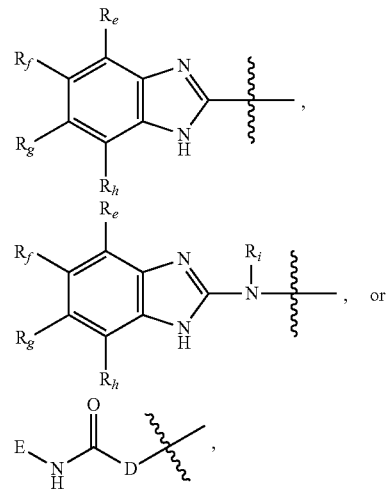

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or $N(R_t)$, $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O-$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_t$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;
m is 0, 1, or 2; and
n is 0, 1, or 2.
For example, the sum of m and n is at least 1.
For example, m is 1 or 2 and n is 0.
For example, m is 2 and n is 0
For example, A is $CH_2$.
For example, A is O.
For example, $L_1$ is N(Y).
For example, $L_1$ is SO or $SO_2$.
For example, Y is $R_d$.
For example, $R_d$ is $C_1$-$C_6$ alkyl.
For example, $L_2$ is absent.
For example, each of G and J independently is $OR_a$.
For example, $R_a$ is H.
For example, $R_9$ is

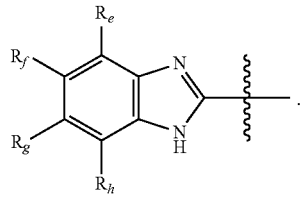

For example, $R_9$ is

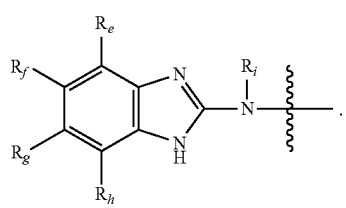

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, $R_i$ is H or $C_1$-$C_6$ alkyl (e.g., methyl, ethyl, n-propyl, i-propyl, n-butyl, s-butyl, t-butyl, n-pentyl, s-pentyl and n-hexyl).

For example,

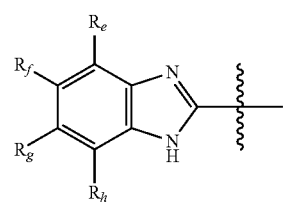

is unsubstituted benzimidazolyl or one of the following groups:

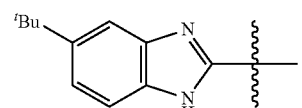

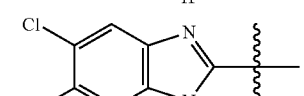

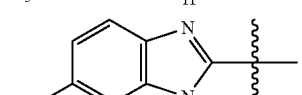

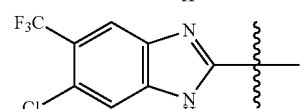

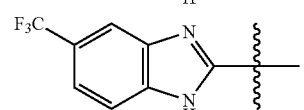

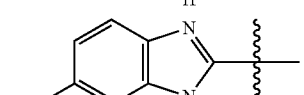

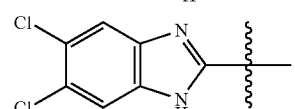

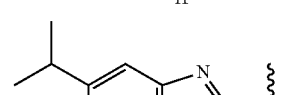

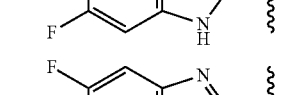

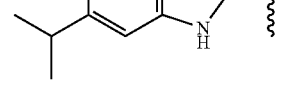

-continued

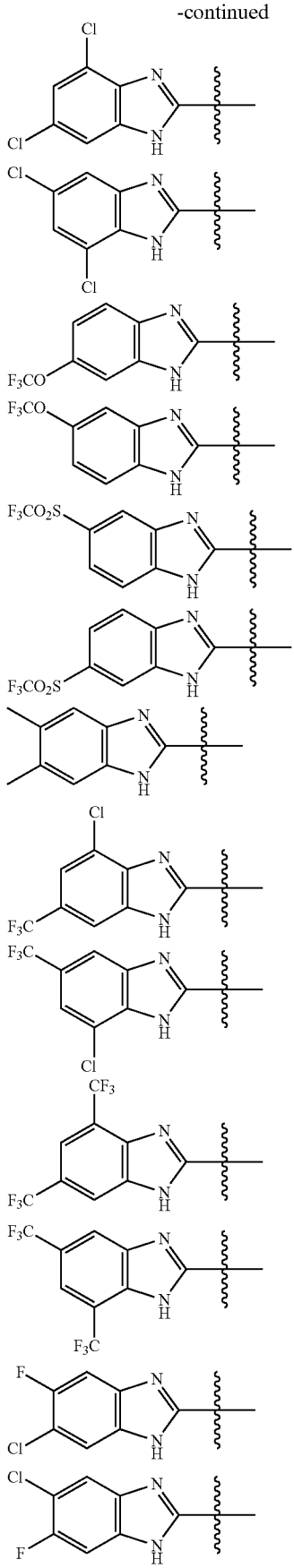

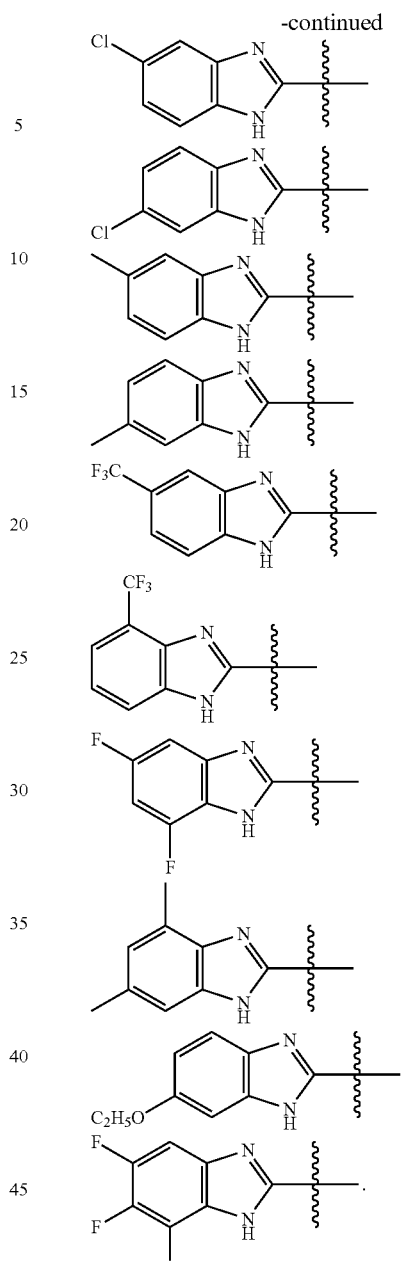

For example, $R_9$ is

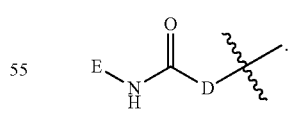

For example, D is O.
For example, D is $NR_j$.
For example, $R_j$ is H.
For example, D is $CR_jR_k$.
For example, each of $R_j$ and $R_k$ is H.
For example, E is $-M_3-T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

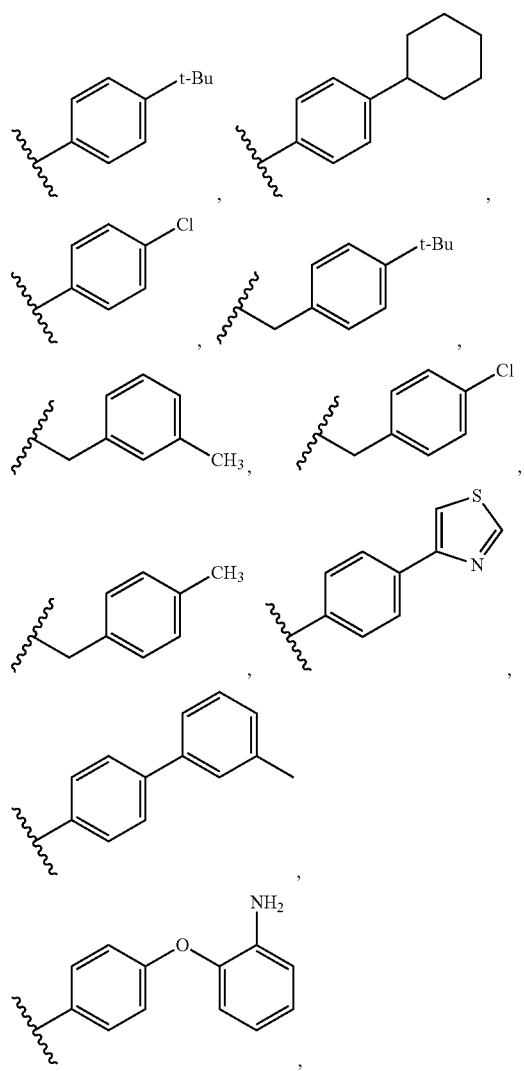

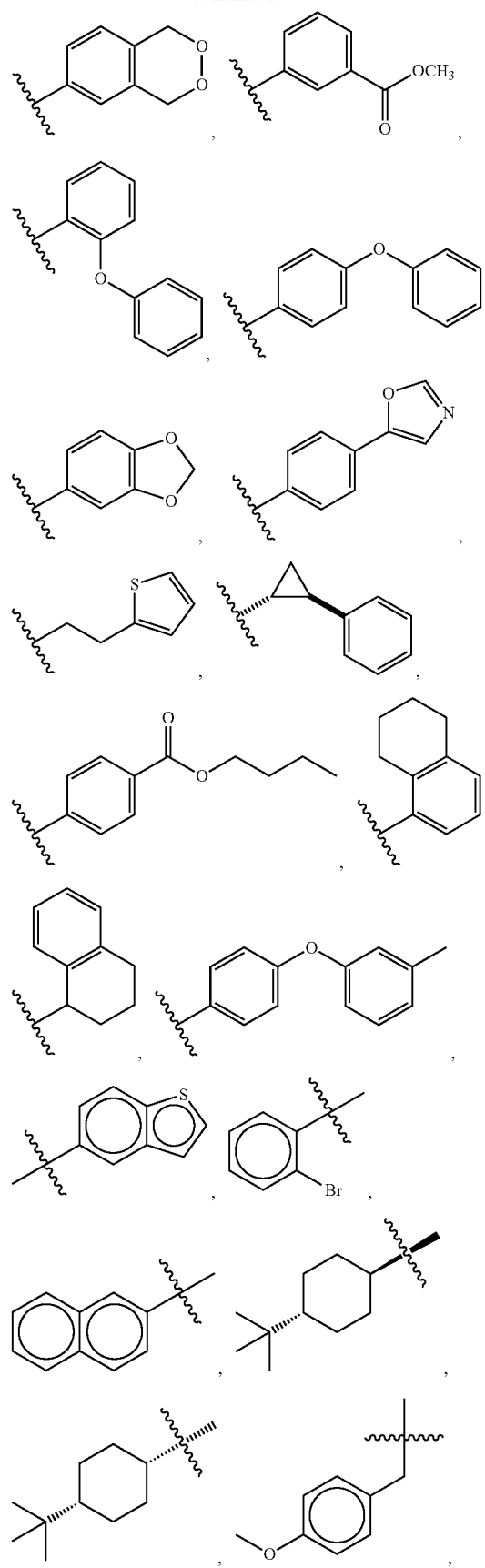

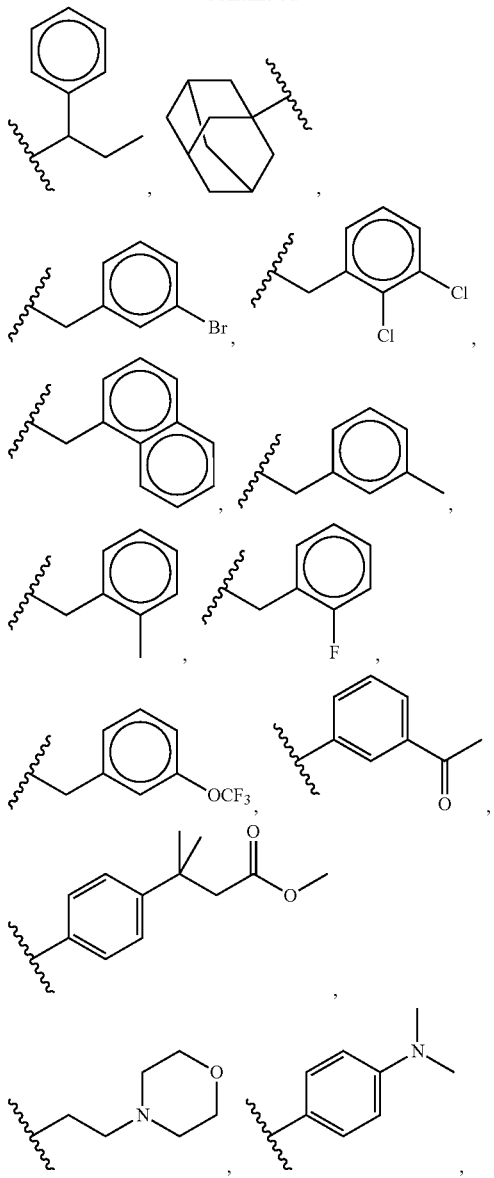

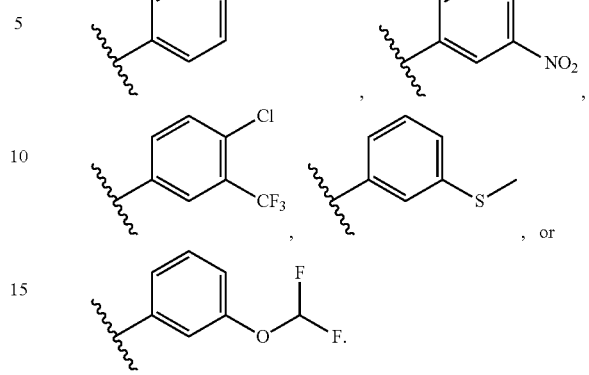

, or

For example, X is N.

For example, X is $CR_x$.

For example, X is CH.

For example, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.

For example, Q is H.

For example, $R_1$, $R_2$, $R_3$, $R_4$, $R_5$, $R_6$, $R_7$, and $R_8$ are each H.

For example, when $R_8$ is halo and is attached to the same carbon atom as J, then J is not hydroxyl.

For example, when $R_8$ is halo and is attached to the same carbon atom as G, then G is not hydroxyl.

For example, $T_2$ is not halo when $M_2$ is $SO_2$, SO, S, CO or O.

For example, $T_2$ is a 4-8 membered heterocycloalkyl which is bound to $M_2$ via a heteroatom.

For example, $T_2$ is a 4-8 membered heterocycloalkyl which is bound to $M_2$ via a N atom.

For example, $T_2$ is a 4-8 membered heterocycloalkyl which is bound to $M_2$ via a C atom.

The present invention provides the compounds of Formula (IVa), (IVb), (IVd), or (IVe):

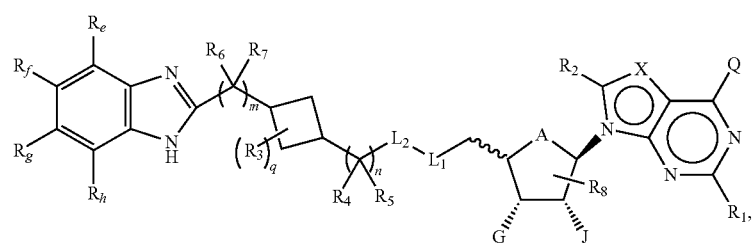

(IVa)

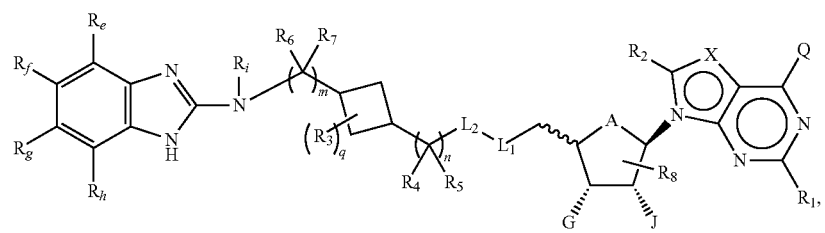

(IVb)

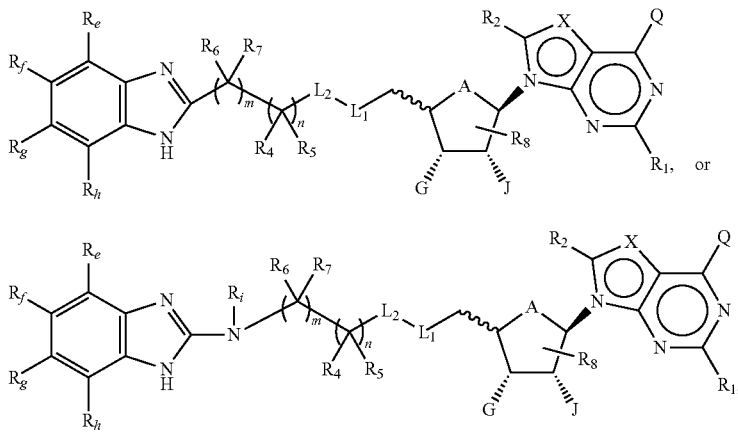

or a pharmaceutically acceptable salt or ester thereof, wherein:

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or $N(R_t)$, $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

q is 0, 1, 2, 3, or 4;
m is 0, 1, or 2; and
n is 0, 1, or 2.

For example, the sum of m and n is at least 1.
For example, m is 1 or 2 and n is 0.
For example, m is 2 and n is 0
For example, A is $CH_2$.
For example, A is O.
For example, $L_1$ is N(Y).
For example, $L_1$ is SO or $SO_2$.
For example, Y is $R_d$.
For example, $R_d$ is $C_1$-$C_6$ alkyl.
For example, $L_2$ is absent.
For example, each of G and J independently is $OR_a$.
For example, $R_a$ is H.
For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, $R_i$ is H or $C_1$-$C_6$ alkyl (e.g., methyl, ethyl, n-propyl, i-propyl, n-butyl, s-butyl, t-butyl, n-pentyl, s-pentyl and n-hexyl).

For example,

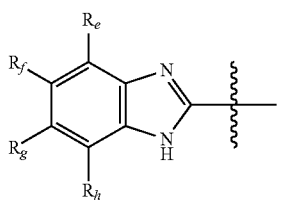

is unsubstituted benzimidazolyl or one of the following groups:

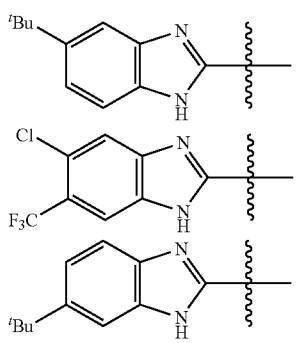

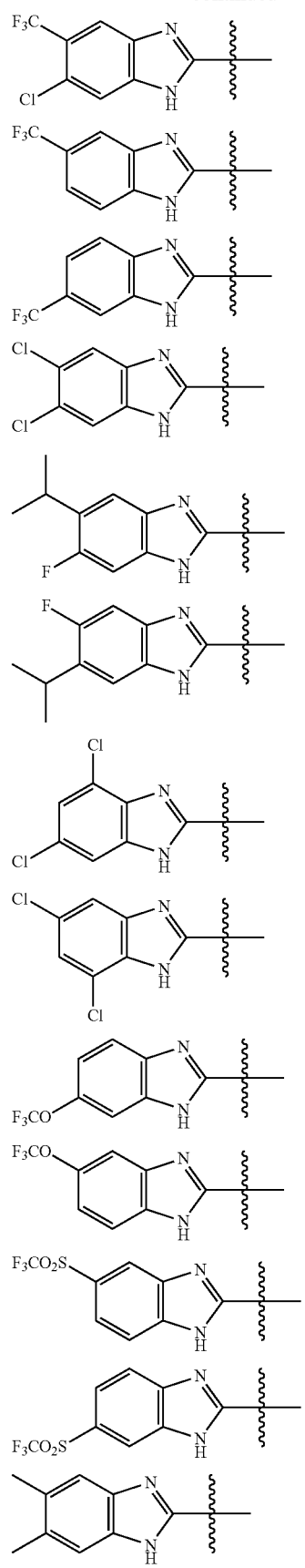

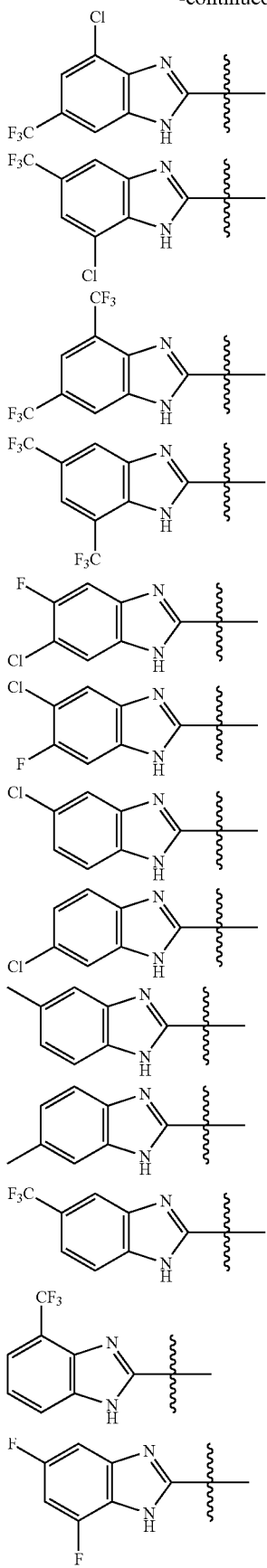

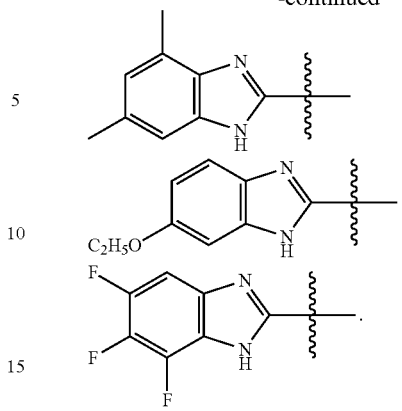

For example, X is N.
For example, X is $CR_x$.
For example, X is CH.
For example, Q is $NH_2$ or $NHR_b$, in which $R_b$ is $-M_1-T_1$, $M_1$ being a bond or $C_1$-$C_6$ alkyl linker and $T_1$ being $C_3$-$C_8$ cycloalkyl.
For example, Q is H.
For example, $R_1$, $R_2$, $R_3$, $R_4$, $R_5$, $R_6$, $R_7$, and $R_8$ are each H.
For example, when $R_8$ is halo and is attached to the same carbon atom as J, then J is not hydroxyl.
For example, when $R_8$ is halo and is attached to the same carbon atom as G, then G is not hydroxyl.
For example, $T_2$ is not halo when $M_2$ is $SO_2$, SO, S, CO or O.
For example, $T_2$ is a 4-8 membered heterocycloalkyl which is bound to $M_2$ via a heteroatom.
For example, $T_2$ is a 4-8 membered heterocycloalkyl which is bound to $M_2$ via a N atom.
For example, $T_2$ is a 4-8 membered heterocycloalkyl which is bound to $M_2$ via a C atom.
The present invention provides the DOT1L inhibitor compounds of Formula (IVc) or (IVf):

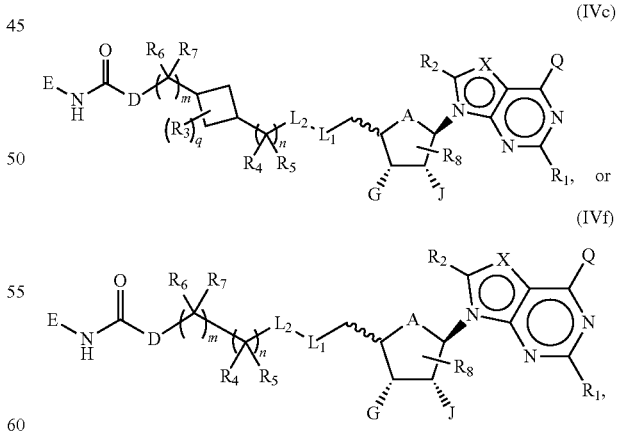

or a pharmaceutically acceptable salt or ester thereof, wherein:
A is O or $CH_2$;
each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring;

E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;

m is 0, 1, or 2; and n is 0, 1, or 2.

For example, the sum of m and n is at least 1.

For example, m is 1 or 2 and n is 0.

For example, m is 2 and n is 0

For example, A is $CH_2$.

For example, A is O.

For example, $L_1$ is N(Y).

For example, $L_1$ is SO or $SO_2$.

For example, Y is $R_d$.

For example, $R_d$ is $C_1$-$C_6$ alkyl.

For example, $L_2$ is absent.

For example, each of G and J independently is $OR_a$.

For example, $R_a$ is H.

For example, D is O.

For example, D is $NR_4$.

For example, $R_j$ is H.

For example, D is $CR_jR_k$.

For example, each of $R_j$ and $R_k$ is H.

For example, E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

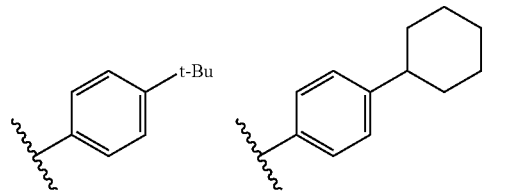

,

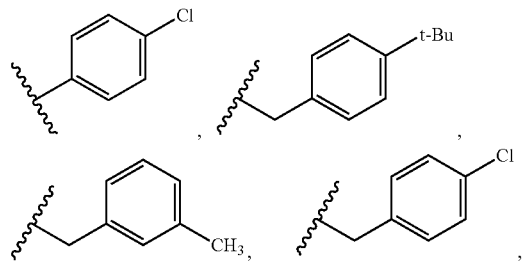

,

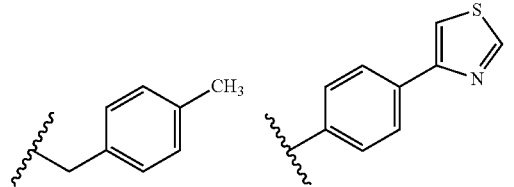

,

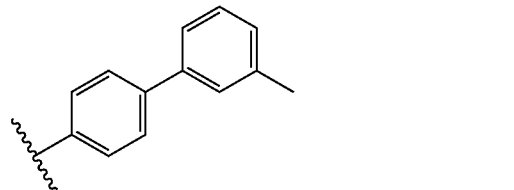

,

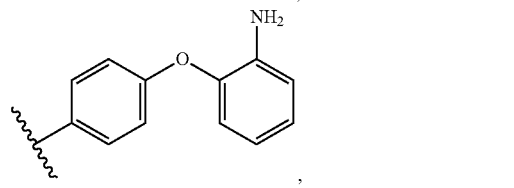

,

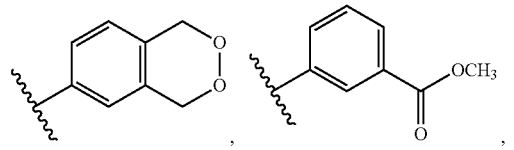

,

-continued

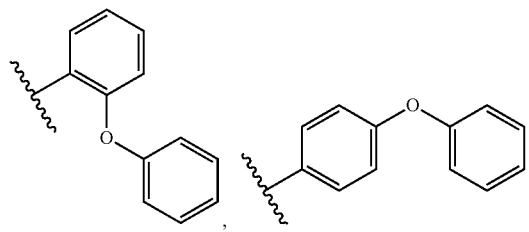

,

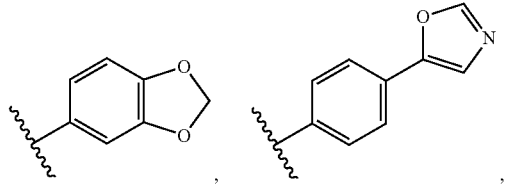

,

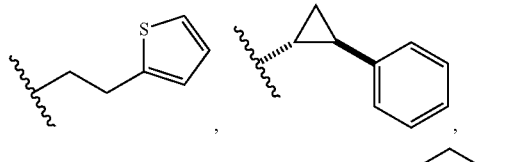

,

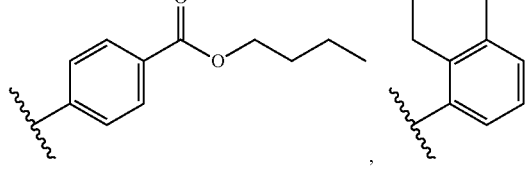

,

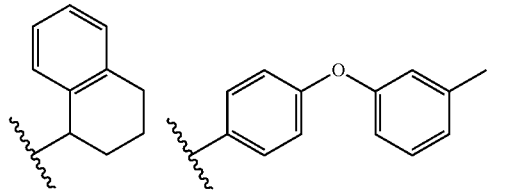

,

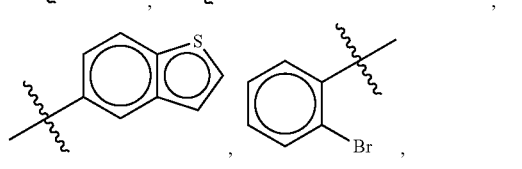

,

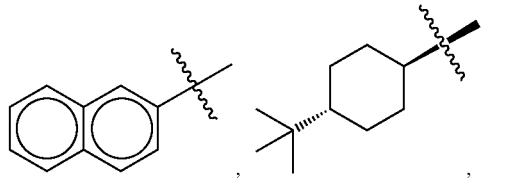

,

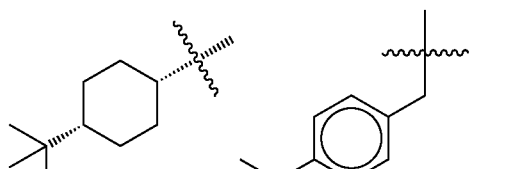

,

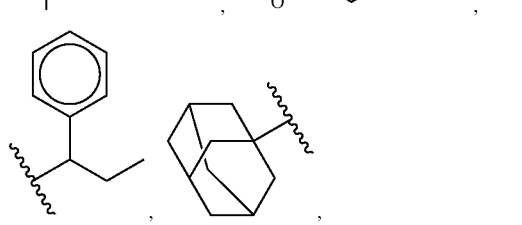

,

-continued

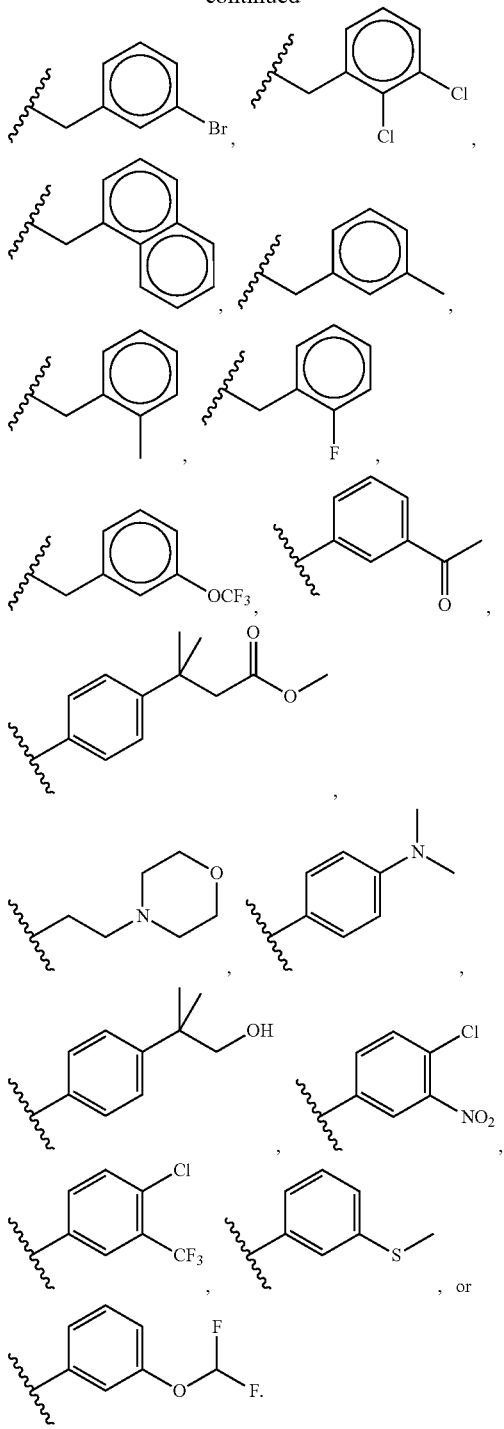

For example, X is N.
For example, X is CR$_x$.
For example, X is CH.
For example, Q is NH$_2$ or NHR$_b$, in which R$_b$ is -M$_1$-T$_1$, M$_1$ being a bond or C$_1$-C$_6$ alkyl linker and T$_1$ being C$_3$-C$_8$ cycloalkyl.
For example, Q is H.
For example, R$_1$, R$_2$, R$_3$, R$_4$, R$_5$, R$_6$, R$_7$, and R$_8$ are each H.
For example, when R$_8$ is halo and is attached to the same carbon atom as J, then J is not hydroxyl.

For example, when R$_8$ is halo and is attached to the same carbon atom as G, then G is not hydroxyl.
For example, T$_2$ is not halo when M$_2$ is SO$_2$, SO, S, CO or O.
For example, T$_2$ is a 4-8 membered heterocycloalkyl which is bound to M$_2$ via a heteroatom.
For example, T$_2$ is a 4-8 membered heterocycloalkyl which is bound to M$_2$ via a N atom.
For example, T$_2$ is a 4-8 membered heterocycloalkyl which is bound to M$_2$ via a C atom.

The invention also relates to a composition comprising one or more therapeutic agents and a compound of Formula (IV) or its N-oxide or a pharmaceutically acceptable salt thereof:

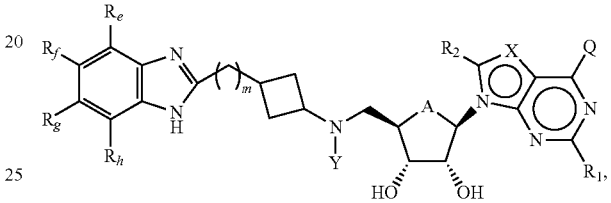

(IV)

wherein A is O or CH$_2$;
Q is H, NH$_2$, NHR$_b$, NR$_b$R$_c$, R$_b$, =O, OH, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;
X is N or CR$_x$, in which R$_x$ is H, halo, hydroxyl, carboxyl, cyano, or R$_{S1}$, R$_{S1}$ being amino, C$_1$-C$_6$ alkoxyl, C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_{S1}$ being optionally substituted with one or more substituents selected from halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;
Y is H, R$_d$, SO$_2$R$_d$, or COR$_d$, R$_d$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_d$ being optionally substituted with one or more substituents selected from C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$ and $R_2$ independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from halo, hydroxyl, carboxyl, cyano, $C_1$-$C_6$ alkoxyl, amino, mono-$C_1$-$C_6$ alkylamino, di-$C_1$-$C_6$ alkylamino, $C_{1-3}$-$C_{1-8}$ cycloalkyl, $C_6$-$C_{10}$ aryl, 4 to 6-membered heterocycloalkyl, and 5 to 6-membered heteroaryl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, and m is 0, 1, or 2.

For example, A is O. In certain compounds of Formula (IV), A is O and m is 2.

In certain compounds of Formula (IV), X is N.

For example, in certain compounds, Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl For example, in certain compounds of Formula (IV), $R_1$ and $R_2$ are each H.

In certain compounds of Formula (IV), Y is $R_d$. For example, $R_d$ is $C_1$-$C_6$ alkyl optionally substituted with $C_3$-$C_8$ cycloalkyl or halo. For example, $R_d$ is $C_3$-$C_8$ cycloalkyl optionally substituted with $C_1$-$C_6$ alkyl or halo.

The invention also relates to a compound of Formula (IV), wherein at least one of $R_e$, $R_f$, $R_g$, and $R_h$ is halo, $C_1$-$C_6$ alkoxyl optionally substituted with one or more halo; $C_1$-$C_6$ alkylsulfonyl optionally substituted with one or more halo; $C_1$-$C_6$ alkyl optionally substituted with one or more substituents selected from CN, halo, $C_3$-$C_8$ cycloalkyl, hydroxy, and $C_1$-$C_6$ alkoxyl; $C_3$-$C_8$ cycloalkyl optionally substituted with one or more $C_1$-$C_6$ alkyl or CN; or 4 to 8-membered heterocycloalkyl optionally substituted with one or more substituents selected from CN, halo, hydroxy, $C_1$-$C_6$ alkyl and $C_1$-$C_6$ alkoxyl. For example, the compound of Formula (IV) has at least one of $R_e$, $R_f$, $R_g$, and $R_h$ selected from F; Cl; Br; $CF_3$; $OCF_3$; $SO_2CF_3$; oxetanyl optionally substituted with one or more substituents selected from CN, halo, hydroxy, $C_1$-$C_6$ alkyl and $C_1$-$C_6$ alkoxyl; $C_3$-$C_8$ cycloalkyl optionally substituted with one or more substituents selected from $C_1$-$C_4$ alkyl; and $C_1$-$C_4$ alkyl optionally substituted with one or more substituents selected from halo, $C_3$-$C_8$ cycloalkyl, hydroxy and $C_1$-$C_6$ alkoxyl.

For example, the invention relates to DOT1L inhibitor compounds of Formula (IV) where at least one of $R_f$ and $R_g$ is alkyl, optionally substituted with hydroxyl. For example, the invention relates to compounds where at least one of $R_f$ and $R_g$ is t-butyl substituted with hydroxyl.

The invention relates to a composition comprising one or more therapeutic agents and i) a compound selected from Tables 1-4; ii) a salt of a compound selected from Tables 1-4; iii) an N-oxide of compound selected from Tables 1-4; or iv) a salt of an N-oxide of compound selected from Tables 1-4. For example, the invention relates to a composition comprising one or more therapeutic agents and a compound selected from Compounds A1-A7, A9-A109, and A111-A140.

In one embodiment, a composition comprises one or more therapeutic agents and Compound A2 (also called "Cpd A2" or "5676") having the formula:

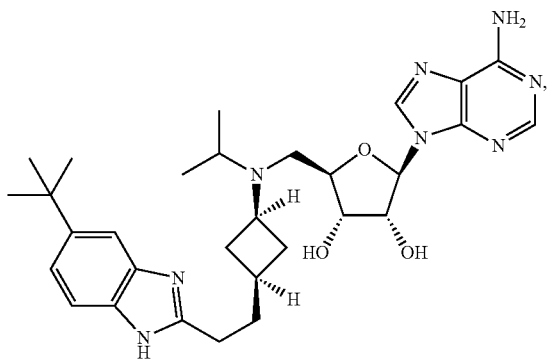 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

or pharmaceutically acceptable salts thereof.

In one embodiment, a composition comprises one or more therapeutic agents and Compound T (i.e., Compound D16) having the formula:

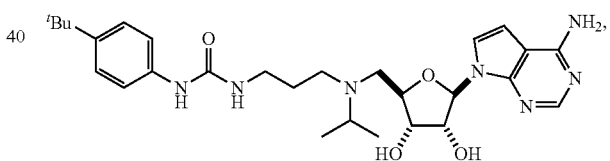

or pharmaceutically acceptable salts thereof.

Other DOT1L inhibitor compounds suitable for this invention are described in WO2012/075381, WO2012/075492, WO2012/082436, and WO2012/75500 the contents of which are hereby incorporated by reference in their entireties.

The invention also relates to a pharmaceutical composition of a therapeutically effective amount of any composition described herein and a pharmaceutically acceptable carrier.

The invention also relates to a pharmaceutical composition of a therapeutically effective amount of one or more therapeutic agents and a compound of any of the Formulae disclosed herein and a pharmaceutically acceptable carrier.

The invention also relates to a pharmaceutical composition of a therapeutically effective amount of one or more therapeutic agents and a salt of a compound of any of the Formulae disclosed herein and a pharmaceutically acceptable carrier.

The invention also relates to a pharmaceutical composition of a therapeutically effective amount of one or more therapeutic agents and a hydrate of a compound of any of the Formulae disclosed herein and a pharmaceutically acceptable carrier.

The invention also relates to a pharmaceutical composition of a therapeutically effective amount of one or more therapeutic agents and a compound selected from Tables 1-4 and a pharmaceutically acceptable carrier. The invention also relates to a pharmaceutical composition of a therapeutically effective amount of one or more therapeutic agents and a salt of a compound selected from Tables 1-4 and a pharmaceutically acceptable carrier. The invention also relates to a pharmaceutical composition of a therapeutically effective amount of one or more therapeutic agents and an N-oxide of a compound selected from Tables 1-4 and a pharmaceutically acceptable carrier. The invention also relates to a pharmaceutical composition of a therapeutically effective amount of one or more therapeutic agents and an N-oxide of salt of a compound selected from Tables 1-4 and a pharmaceutically acceptable carrier. The invention also relates to a pharmaceutical composition of a therapeutically effective amount of one or more therapeutic agents and a hydrate of a compound selected from Tables 1-4 and a pharmaceutically acceptable carrier.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Representative compounds of the present invention include compounds listed in Tables 1-4.

TABLE 1

| Cmpd No. | Structure | Chemical Name | Data (MS or NMR) |
|---|---|---|---|
| A1 | 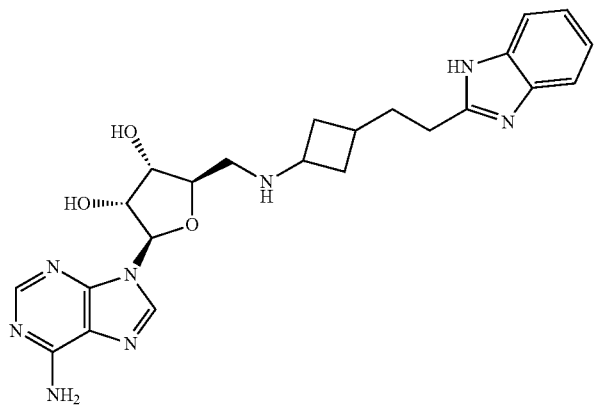 [SMILES: Nc1ncnc2c1ncn2[C@@H]1O[C@H](CNC2CC(CCc3nc4ccccc4[nH]3)C2)[C@@H](O)[C@H]1O] | (2R,3S,4R,5R)-2-(((3-(2-(1H-benzo[d]imidazol-2-yl)ethyl)cyclobutyl)amino)methyl)-5-(6-amino-9H-purin-9-yl)tetrahydrofuran-3,4-diol | |
| A2 | 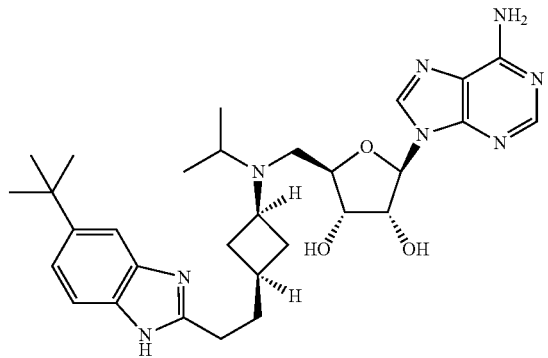 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol | 563.4 (M + H)+ |

TABLE 1-continued

| Cmpd No. | Structure | Chemical Name | Data (MS or NMR) |
|---|---|---|---|
| A3 | 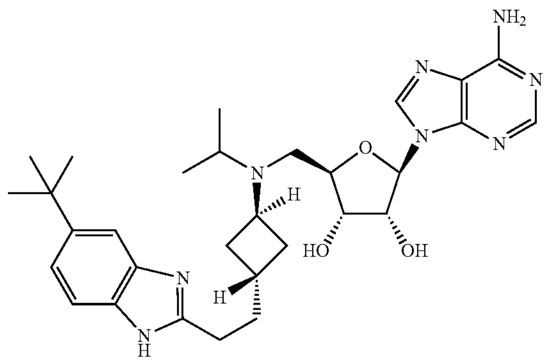 [SMILES: CC(C)N(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(isopropyl)amino)methyl)tetrahydrofuran-3,4-diol | 563.5 (M + H)+ |
| A4 | 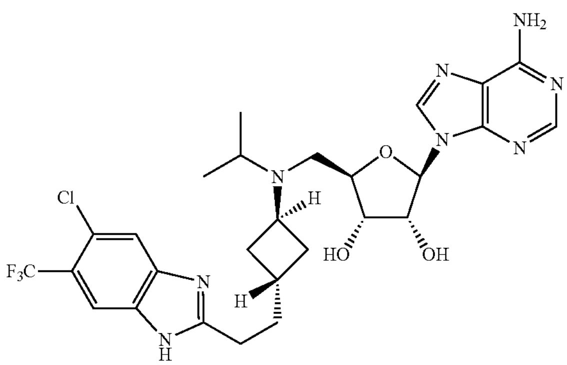 [SMILES: CC(C)N(C[C@H]1O[C@@H](n2cnc3c(N)ncnc32)[C@H](O)[C@@H]1O)[C@H]1C[C@H](CCc2nc3cc(Cl)c(C(F)(F)F)cc3[nH]2)C1] | (2R,3R,4S,5R)-2-(6-amino-9H-purin-9-yl)-5-((((1s,3R)-3-(2-(5-chloro-6-(trifluoromethyl)-1H-benzo[d]imidazol-2-yl)ethyl)cyclobutyl)(isopropyl)amino)methyl)tetrahydrofuran-3,4-diol | 609.2 (M + H)+ |
| A5 | 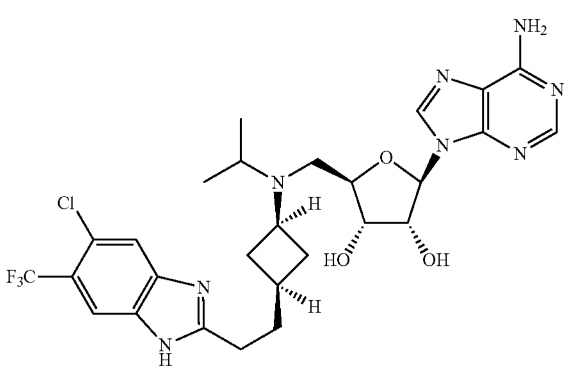 [SMILES: CC(C)N(C[C@H]1O[C@@H](n2cnc3c(N)ncnc32)[C@H](O)[C@@H]1O)[C@H]1C[C@@H](CCc2nc3cc(Cl)c(C(F)(F)F)cc3[nH]2)C1] | (2R,3R,4S,5R)-2-(6-amino-9H-purin-9-yl)-5-((((1r,3S)-3-(2-(5-chloro-6-(trifluoromethyl)-1H-benzo[d]imidazol-2-yl)ethyl)cyclobutyl)(isopropyl)amino)methyl)tetrahydrofuran-3,4-diol | 609.2 (M + H)+ |

TABLE 1-continued

| Cmpd No. | Structure | Chemical Name | Data (MS or NMR) |
|---|---|---|---|
| A6 | 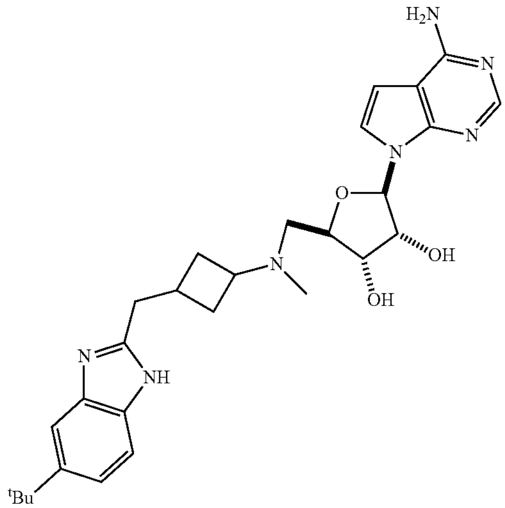 | (2R,3R,4S,5R)-2-(4-amino-7H-pyrrolo[2,3-d]pyrimidin-7-yl)-5-(((3-((5-(tert-butyl)-1H-benzo[d]imidazol-2-yl)methyl)cyclobutyl)(methyl)amino)methyl)tetrahydrofuran-3,4-diol | 520.4 (M + H)+ |
| A7 | 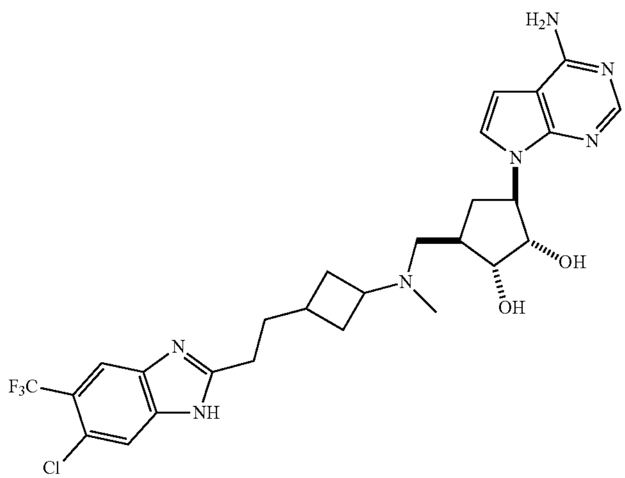 [SMILES: CN(C[C@H]1C[C@@H](n2ccc3c(N)ncnc32)[C@H](O)[C@@H]1O)C1CC(CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(methyl)amino)methyl)cyclopentane-1,2-diol | 579.7 (M + H)+ |
| A8 | 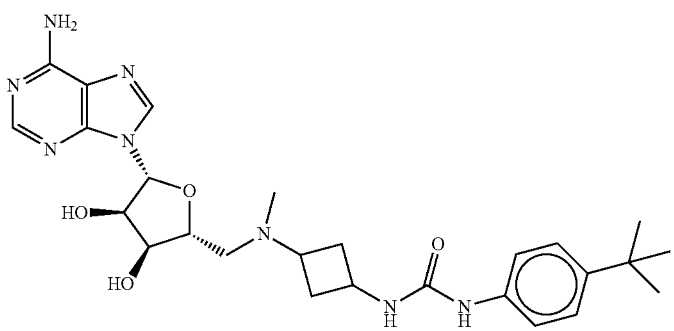 | 1-(3-((((2R,3S,4R,5R)-5-(6-amino-9H-purin-9-yl)-3,4-dihydroxytetrahydrofuran-2-yl)methyl)(methyl)amino)cyclobutyl)-3-(4-tert-butylphenyl)urea | 525.5 (M + H)+ |
| A9 | 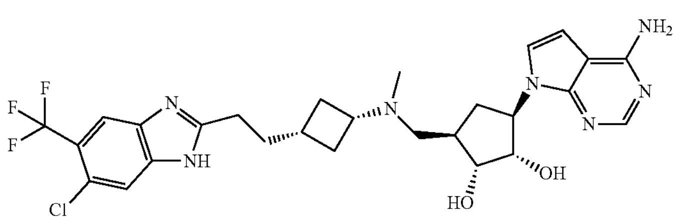 [SMILES: CN(C[C@H]1C[C@@H](n2ccc3c(N)ncnc32)[C@H](O)[C@@H]1O)[C@H]1C[C@@H](CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-((((1r,3S)-3-(2-(6-chloro-5-(trifluoromethyl)-1H-benzo[d]imidazol-2-yl)ethyl)cyclobutyl)(methyl)amino)methyl)cyclopentane-1,2-diol | 578.3 (M + H)+ |

TABLE 1-continued

| Cmpd No. | Structure | Chemical Name | Data (MS or NMR) |
|---|---|---|---|
| A10 | 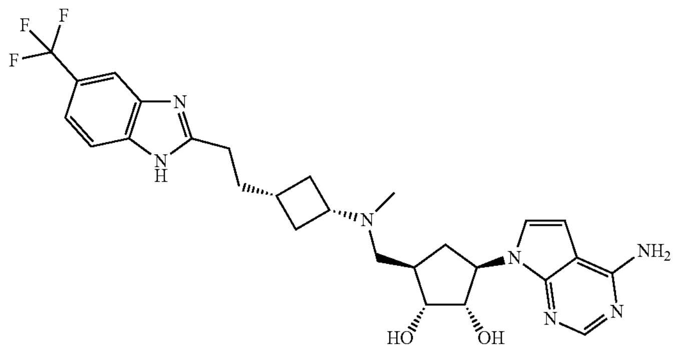 [SMILES: CN(C[C@H]1C[C@@H](n2ccc3c(N)ncnc32)[C@H](O)[C@@H]1O)[C@H]1C[C@@H](CCc2nc3cc(C(F)(F)F)ccc3[nH]2)C1] | (1R,2S,3R,5R)-3-(4-amino-7H-pyrrolo[2,3-d]pyrimidin-7-yl)-5-((methyl((1r,3S)-3-(2-(5-(trifluoromethyl)-1H-benzo[d]imidazol-2-yl)ethyl)cyclobutyl)amino)methyl)cyclopentane-1,2-diol | 544.3 (M + H)+ |
| A11 | 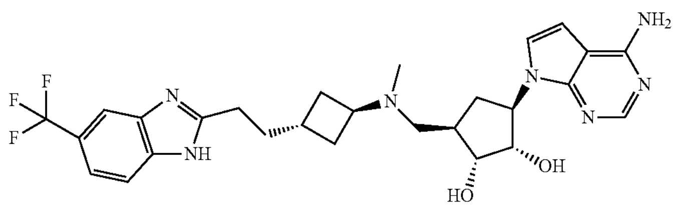 [SMILES: CN(C[C@H]1C[C@@H](n2ccc3c(N)ncnc32)[C@H](O)[C@@H]1O)[C@H]1C[C@H](CCc2nc3cc(C(F)(F)F)ccc3[nH]2)C1] | (1R,2S,3R,5R)-3-(4-amino-7H-pyrrolo[2,3-d]pyrimidin-7-yl)-5-((methyl((1s,3R)-3-(2-(5-(trifluoromethyl)-1H-benzo[d]imidazol-2-yl)ethyl)cyclobutyl)amino)methyl)cyclopentane-1,2-diol | 544.3 (M + H)+ |
| A12 | 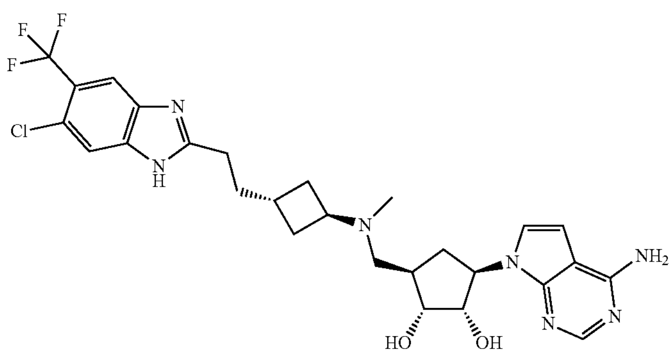 [SMILES: CN(C[C@H]1C[C@@H](n2ccc3c(N)ncnc32)[C@H](O)[C@@H]1O)[C@H]1C[C@H](CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-((((1s,3R)-3-(2-(6-chloro-5-(trifluoromethyl)-1H-benzo[d]imidazol-2-yl)ethyl)cyclobutyl)(methyl)amino)methyl)cyclopentane-1,2-diol | 578.3 (M + H)+ |
| A13 | 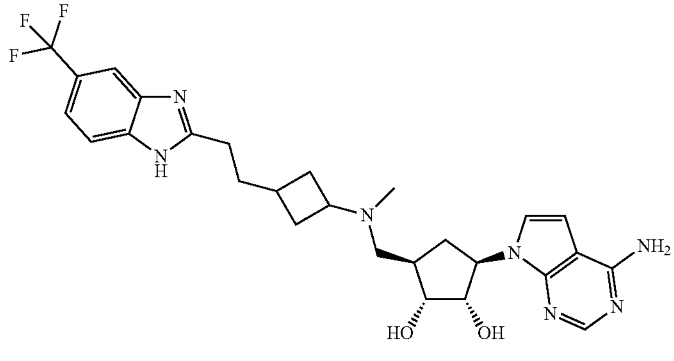 [SMILES: CN(C[C@H]1C[C@@H](n2ccc3c(N)ncnc32)[C@H](O)[C@@H]1O)C1CC(CCc2nc3cc(C(F)(F)F)ccc3[nH]2)C1] | (1R,2S,3R,5R)-3-(4-amino-7H-pyrrolo[2,3-d]pyrimidin-7-yl)-5-((methyl(3-(2-(5-(trifluoromethyl)-1H-benzo[d]imidazol-2-yl)ethyl)cyclobutyl)amino)methyl)cyclopentane-1,2-diol | 544.5 (M + H)+ |

TABLE 1-continued

| Cmpd No. | Structure | Chemical Name | Data (MS or NMR) |
|---|---|---|---|
| A14 | 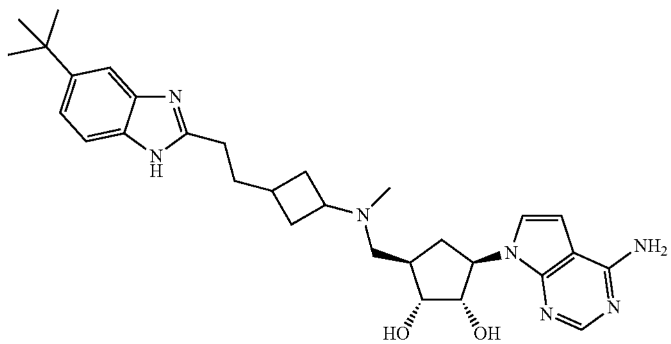 [SMILES: CN(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(methyl)amino)methyl)cyclopentane-1,2-diol | 532.3 (M + H)+ |
| A15 | 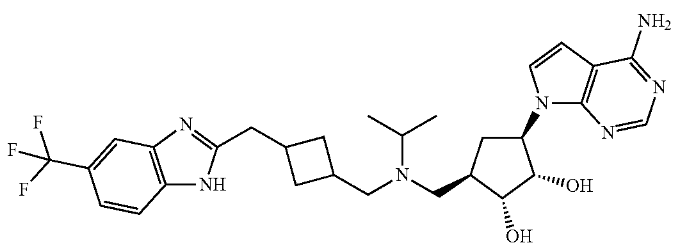 [SMILES: CC(C)N(CC1CC(Cc2nc3cc(C(F)(F)F)ccc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((isopropyl((3-((5-(trifluoromethyl)-1H-benzo[d]imidazol-2-yl)methyl)cyclobutyl)methyl)amino)methyl)cyclopentane-1,2-diol | 572.4 (M + H)+ |
| A16 | 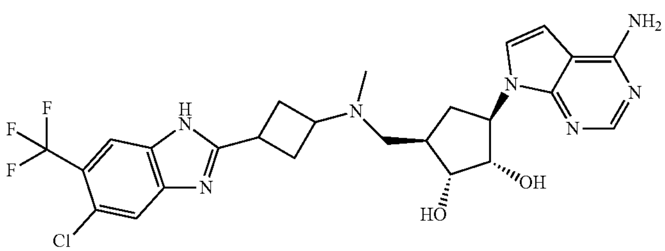 [SMILES: CN(C[C@H]1C[C@@H](n2ccc3c(N)ncnc32)[C@H](O)[C@@H]1O)C1CC(c2nc3cc(Cl)c(C(F)(F)F)cc3[nH]2)C1] | (1R,2S,3R,5R)-3-(4-amino-7H-pyrrolo[2,3-d]pyrimidin-7-yl)-5-(((3-(5-chloro-6-(trifluoromethyl)-1H-benzo[d]imidazol-2-yl)cyclobutyl)(methyl)amino)methyl)cyclopentane-1,2-diol | 550.3 (M + H)+ |
| A17 | 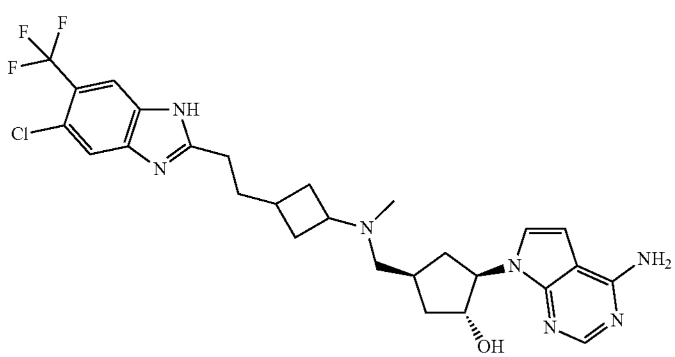 [SMILES: CN(C[C@@H]1C[C@@H](O)[C@H](n2ccc3c(N)ncnc32)C1)C1CC(CCc2nc3cc(Cl)c(C(F)(F)F)cc3[nH]2)C1] | (1R,2R,4S)-2-(4-amino-7H-pyrrolo[2,3-d]pyrimidin-7-yl)-4-(((3-(2-(5-chloro-6-(trifluoromethyl)-1H-benzo[d]imidazol-2-yl)ethyl)cyclobutyl)(methyl)amino)methyl)cyclopentanol | 562.3 (M + H)+ |
| A18 | 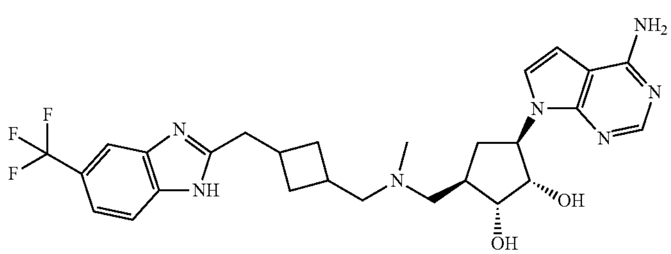 [SMILES: CN(CC1CC(Cc2nc3cc(C(F)(F)F)ccc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((methyl((3-((5-(trifluoromethyl)-1H-benzo[d]imidazol-2-yl)methyl)cyclobutyl)methyl)amino)methyl)cyclopentane-1,2-diol | 544 (M + H)+ |

TABLE 1-continued

| Cmpd No. | Structure | Chemical Name | Data (MS or NMR) |
|---|---|---|---|
| A19 | 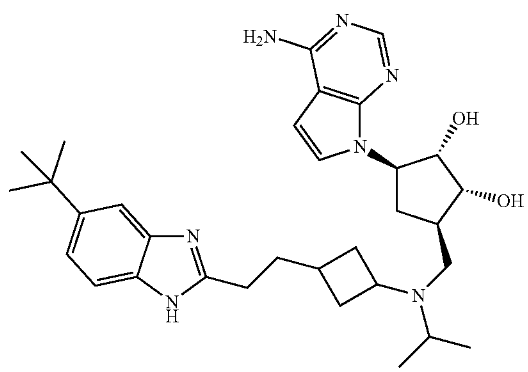 [SMILES: CC(C)N(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isopropyl)amino)methyl)cyclopentane-1,2-diol | NMR data |
| A20 | 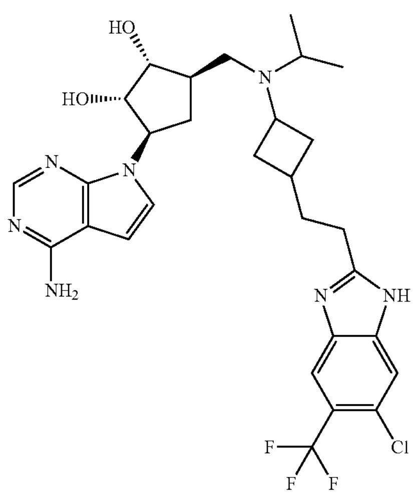 [SMILES: CC(C)N(C[C@H]1C[C@@H](n2ccc3c(N)ncnc32)[C@H](O)[C@@H]1O)C1CC(CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(isopropyl)amino)methyl)cyclopentane-1,2-diol | NMR data |
| A21 | 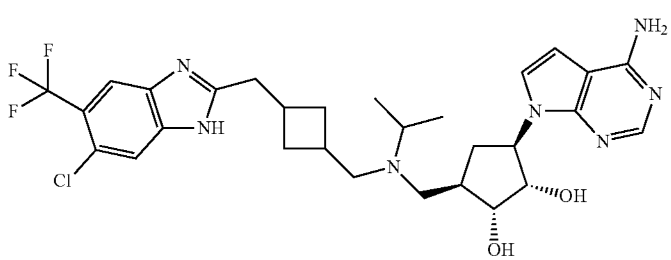 [SMILES: CC(C)N(CC1CC(Cc2nc3cc(C(F)(F)F)c(Cl)cc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((((3-((6-chloro-5-(trifluoromethyl)-1H-benzo[d]imidazol-2-yl)methyl)cyclobutyl)methyl)(isopropyl)amino)methyl)cyclopentane-1,2-diol | 606.3 (M + H)+ |
| A22 | 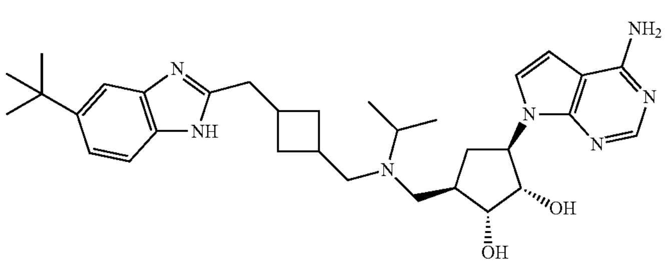 [SMILES: CC(C)N(CC1CC(Cc2nc3cc(C(C)(C)C)ccc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((((3-((5-(tert-butyl)-1H-benzo[d]imidazol-2-yl)methyl)cyclobutyl)methyl)(isopropyl)amino)methyl)cyclopentane-1,2-diol | 560.4 (M + H)+ |

TABLE 1-continued

| Cmpd No. | Structure | Chemical Name | Data (MS or NMR) |
|---|---|---|---|
| A23 | 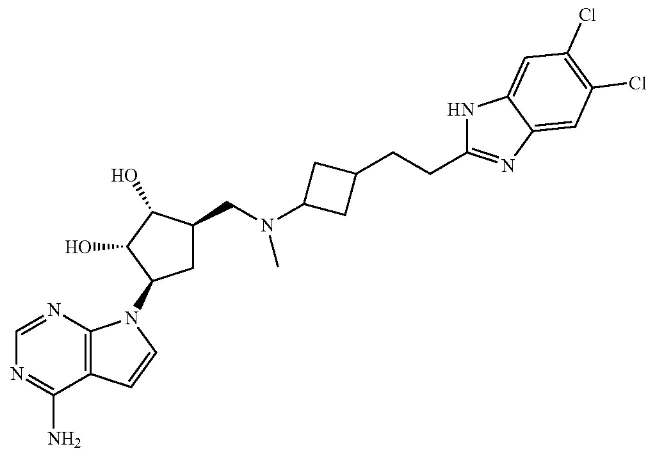 [SMILES: CN(C[C@H]1C[C@@H](n2ccc3c(N)ncnc32)[C@H](O)[C@@H]1O)C1CC(CCc2nc3cc(Cl)c(Cl)cc3[nH]2)C1] | (1R,2S,3R,5R)-3-(4-amino-7H-pyrrolo[2,3-d]pyrimidin-7-yl)-5-(((3-(2-(5,6-dichloro-1H-benzo[d]imidazol-2-yl)ethyl)cyclobutyl)(methyl)amino)methyl)cyclopentane-1,2-diol | NMR data |
| A24 | 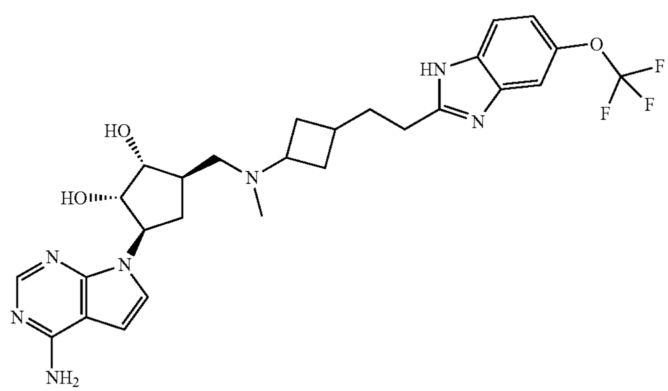 [SMILES: CN(C[C@H]1C[C@@H](n2ccc3c(N)ncnc32)[C@H](O)[C@@H]1O)C1CC(CCc2nc3cc(OC(F)(F)F)ccc3[nH]2)C1] | (1R,2S,3R,5R)-3-(4-amino-7H-pyrrolo[2,3-d]pyrimidin-7-yl)-5-((methyl(3-(2-(5-(trifluoromethoxy)-1H-benzo[d]imidazol-2-yl)ethyl)cyclobutyl)amino)methyl)cyclopentane-1,2-diol | 558.2 (M − H)+ |
| A25 | 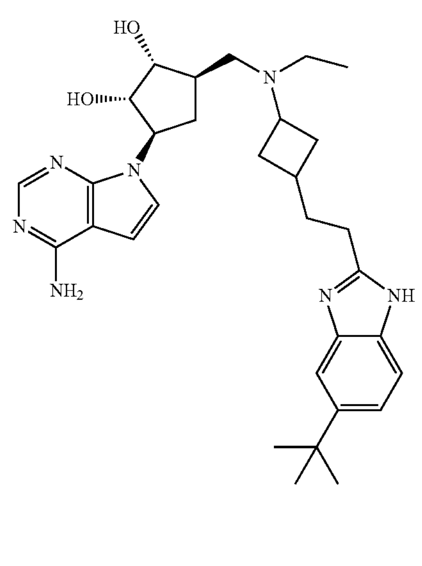 [SMILES: CCN(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(ethyl)amino)methyl)cyclopentane-1,2-diol | 546.3 (M + H)+ |

TABLE 1-continued

| Cmpd No. | Structure | Chemical Name | Data (MS or NMR) |
|---|---|---|---|
| A26 | 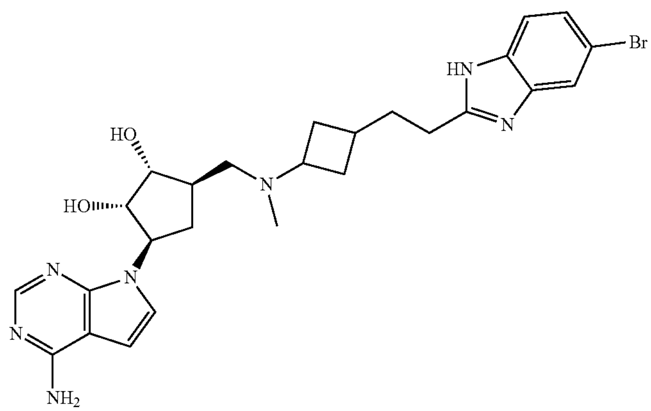 [SMILES: CN(C[C@H]1C[C@@H](n2ccc3c(N)ncnc32)[C@H](O)[C@@H]1O)C1CC(CCc2nc3cc(Br)ccc3[nH]2)C1] | (1R,2S,3R,5R)-3-(4-amino-7H-pyrrolo[2,3-d]pyrimidin-7-yl)-5-(((3-(2-(5-bromo-1H-benzo[d]imidazol-2-yl)ethyl)cyclobutyl)(methyl)amino)methyl)cyclopentane-1,2-diol | 554.1 (M + H)$^+$ |
| A27 | 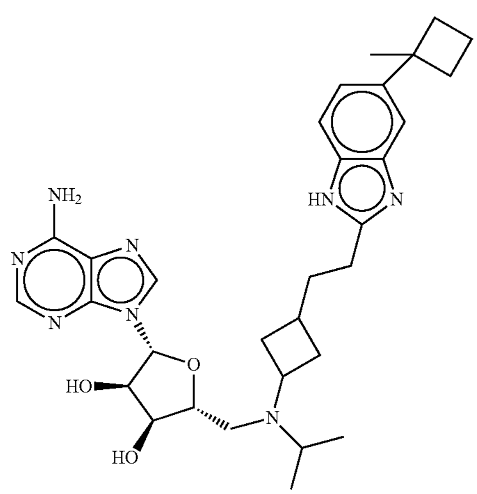 | (2R,3R,4S,5R)-2-(6-amino-9H-purin-9-yl)-5-((isopropyl(3-(2-(5-(1-methylcyclobutyl)-1H-benzo[d]imidazol-2-yl)ethyl)cyclobutyl)amino)methyl)tetrahydrofuran-3,4-diol | 575.5 (M + H)$^+$ |
| A28 | 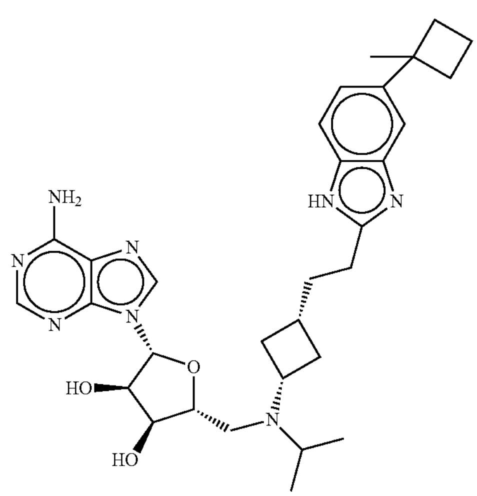 | (2R,3R,4S,5R)-2-(6-amino-9H-purin-9-yl)-5-((isopropyl((1r,3S)-3-(2-(5-(1-methylcyclobutyl)-1H-benzo[d]imidazol-2-yl)ethyl)cyclobutyl)amino)methyl)tetrahydrofuran-3,4-diol | 575.5 (M + H)$^+$ |

TABLE 1-continued

| Cmpd No. | Structure | Chemical Name | Data (MS or NMR) |
|---|---|---|---|
| A29 | 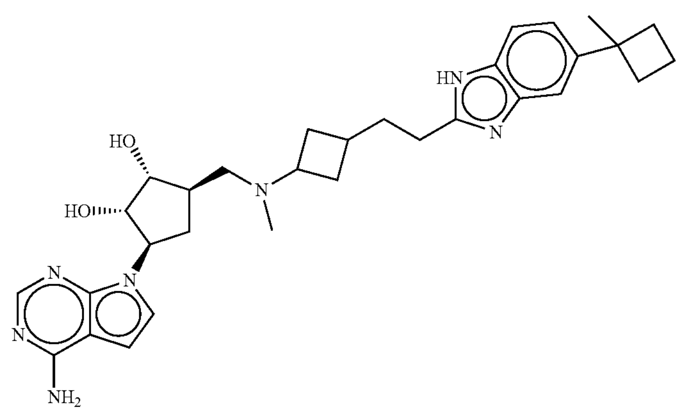 | (1R,2S,3R,5R)-3-(4-amino-7H-pyrrolo[2,3-d]pyrimidin-7-yl)-5-((methyl(3-(2-(5-(1-methylcyclobutyl)-1H-benzo[d]imidazol-2-yl)ethyl)cyclobutyl)amino)methyl)cyclopentane-1,2-diol | 544.4 (M + H)+ |
| A30 | 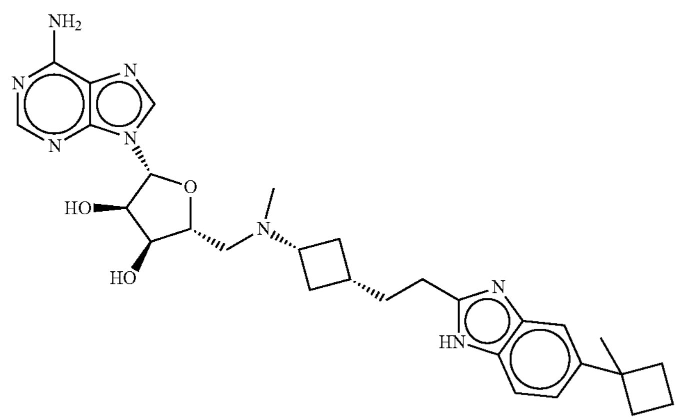 | (2R,3R,4S,5R)-2-(6-amino-9H-purin-9-yl)-5-((methyl((1r,3S)-3-(2-(5-(1-methylcyclobutyl)-1H-benzo[d]imidazol-2-yl)ethyl)cyclobutyl)amino)methyl)tetrahydrofuran-3,4-diol | 547.6 (M + H)+ |
| A31 | 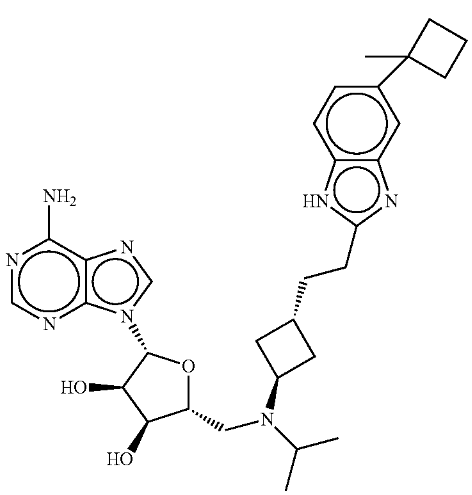 | (2R,3R,4S,5R)-2-(6-amino-9H-purin-9-yl)-5-((isopropyl((1s,3R)-3-(2-(5-(1-methylcyclobutyl)-1H-benzo[d]imidazol-2-yl)ethyl)cyclobutyl)amino)methyl)tetrahydrofuran-3,4-diol | 575.6 (M + H)+ |

TABLE 1-continued

| Cmpd No. | Structure | Chemical Name | Data (MS or NMR) |
|---|---|---|---|
| A32 | 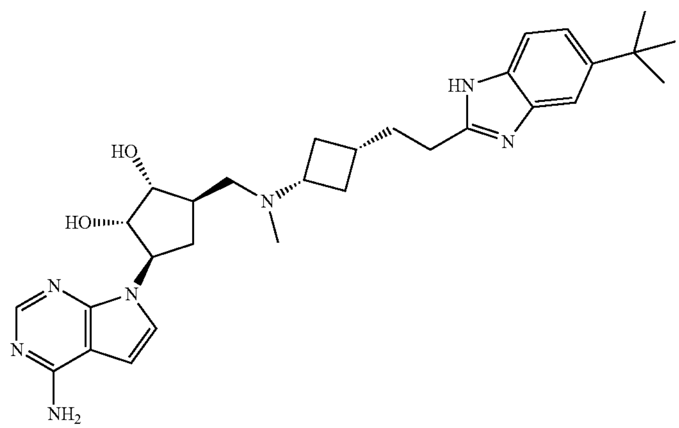 [SMILES: CN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(methyl)amino)methyl)cyclopentane-1,2-diol | 532.4 (M + H)+ |
| A33 | 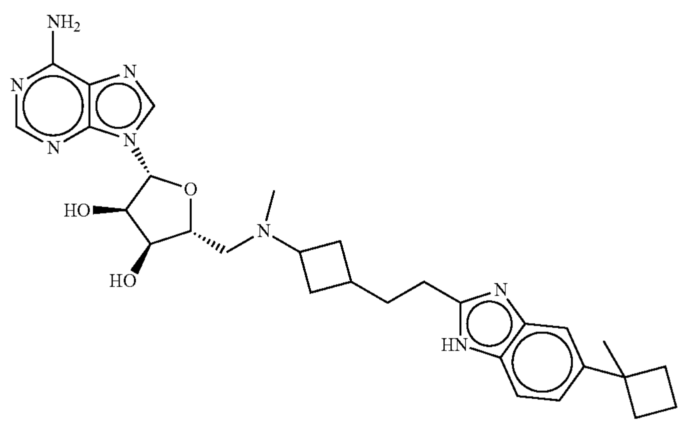 | (2R,3R,4S,5R)-2-(6-amino-9H-purin-9-yl)-5-((methyl(3-(2-(5-(1-methylcyclobutyl)-1H-benzo[d]imidazol-2-yl)ethyl)cyclobutyl)amino)methyl)tetrahydrofuran-3,4-diol | 547.3 (M + H)+ |
| A34 | 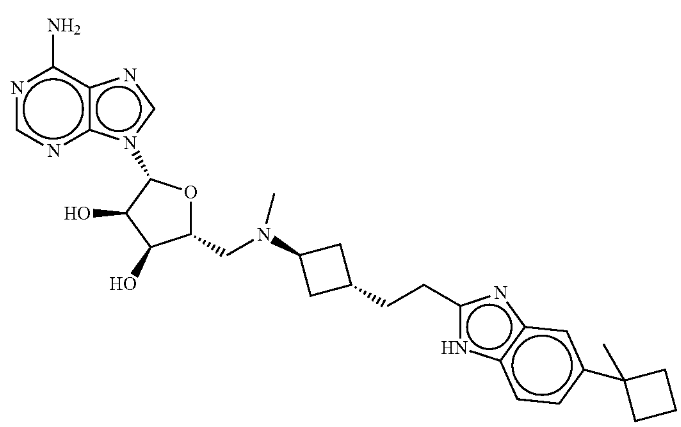 | (2R,3R,4S,5R)-2-(6-amino-9H-purin-9-yl)-5-((methyl((1s,3R)-3-(2-(5-(1-methylcyclobutyl)-1H-benzo[d]imidazol-2-yl)ethyl)cyclobutyl)amino)methyl)tetrahydrofuran-3,4-diol | 547.5 (M + H)+ |

TABLE 1-continued

| Cmpd No. | Structure | Chemical Name | Data (MS or NMR) |
|---|---|---|---|
| A35 | 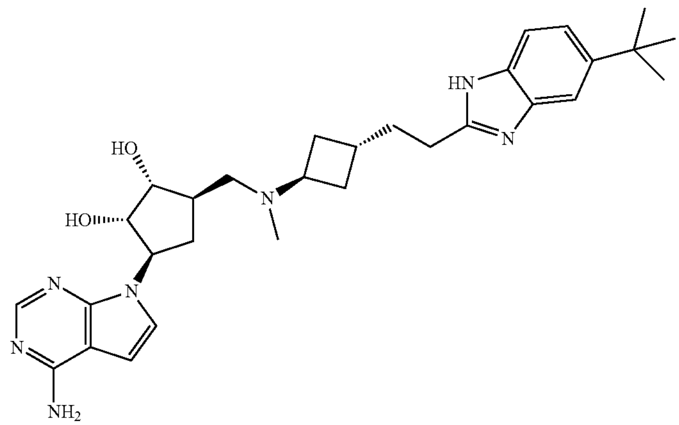 [SMILES: CN(C[C@H]1C[C@@H](n2ccc3c(N)ncnc32)[C@H](O)[C@@H]1O)[C@H]1C[C@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)cyclopentane-1,2-diol | NMR data |
| A36 | 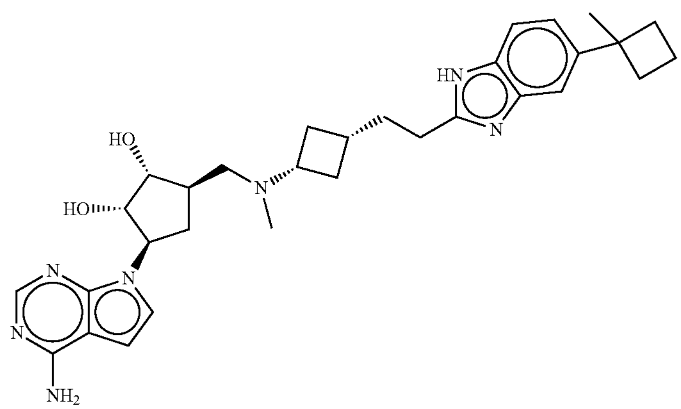 | (1R,2S,3R,5R)-3-(4-amino-7H-pyrrolo[2,3-d]pyrimidin-7-yl)-5-((methyl((1r,3S)-3-(2-(5-(1-methylcyclobutyl)-1H-benzo[d]imidazol-2-yl)ethyl)cyclobutyl)amino)methyl)cyclopentane-1,2-diol | 544.4 (M + H)+ |
| A37 | 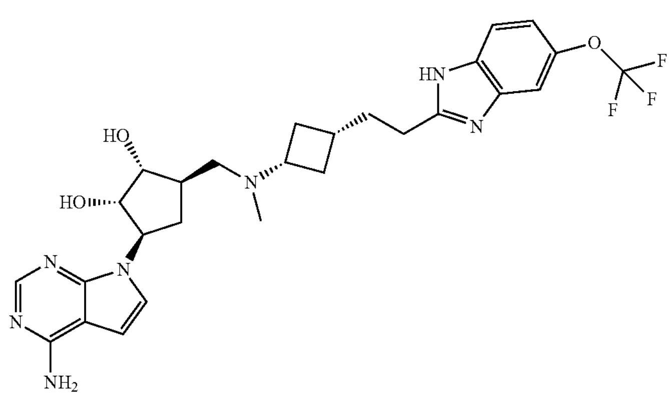 [SMILES: CN(C[C@H]1C[C@@H](n2ccc3c(N)ncnc32)[C@H](O)[C@@H]1O)[C@H]1C[C@@H](CCc2nc3cc(OC(F)(F)F)ccc3[nH]2)C1] | (1R,2S,3R,5R)-3-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)cyclopentane-1,2-diol | 558.3 (M − H)− |

TABLE 1-continued

| Cmpd No. | Structure | Chemical Name | Data (MS or NMR) |
|---|---|---|---|
| A38 | 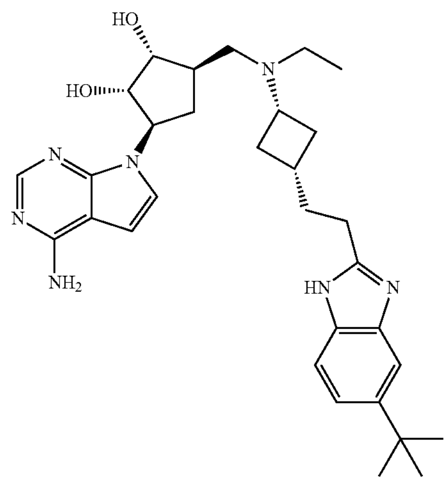 [SMILES: CCN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(ethyl)amino)methyl)cyclopentane-1,2-diol | 546.3 (M + H)+ |
| A39 | 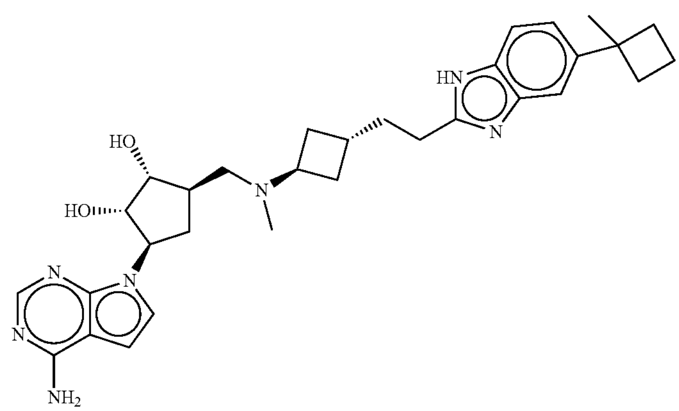 | (1R,2S,3R,5R)-3-(4-amino-7H-pyrrolo[2,3-d]pyrimidin-7-yl)-5-((methyl((1s,3R)-3-(2-(5-(1-methylcyclobutyl)-1H-benzo[d]imidazol-2-yl)ethyl)cyclobutyl)amino)methyl)cyclopentane-1,2-diol | 544.3 (M + H)+ |
| A40 | 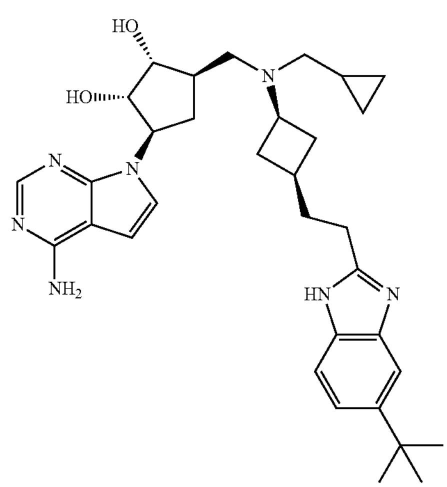 [SMILES: CC(C)(C)c1ccc2[nH]c(CC[C@H]3C[C@@H](N(CC4CC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclopropylmethyl)amino)methyl)cyclopentane-1,2-diol | NMR data |

TABLE 1-continued

| Cmpd No. | Structure | Chemical Name | Data (MS or NMR) |
|---|---|---|---|
| A41 | 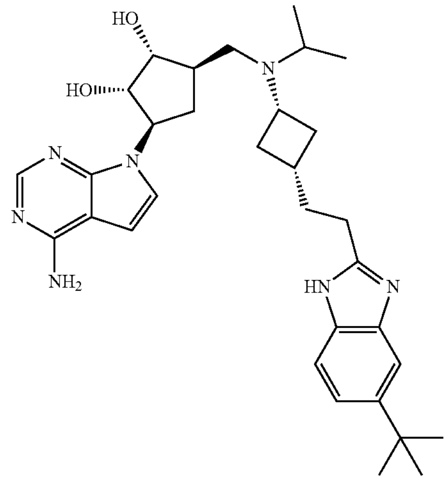 [SMILES: CC(C)N(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isopropyl)amino)methyl)cyclopentane-1,2-diol | NMR data |
| A42 | 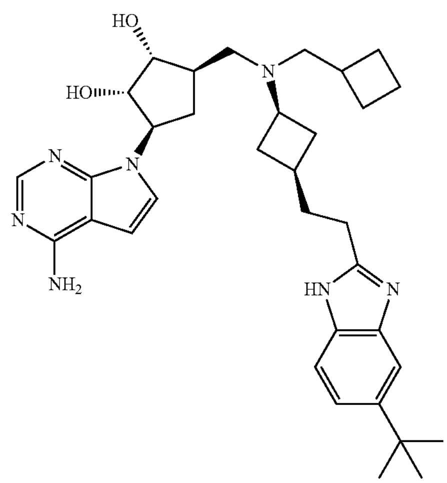 [SMILES: CC(C)(C)c1ccc2[nH]c(CC[C@H]3C[C@@H](N(CC4CCC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclobutylmethyl)amino)methyl)cyclopentane-1,2-diol | 586.3 (M + H)+ |
| A43 | 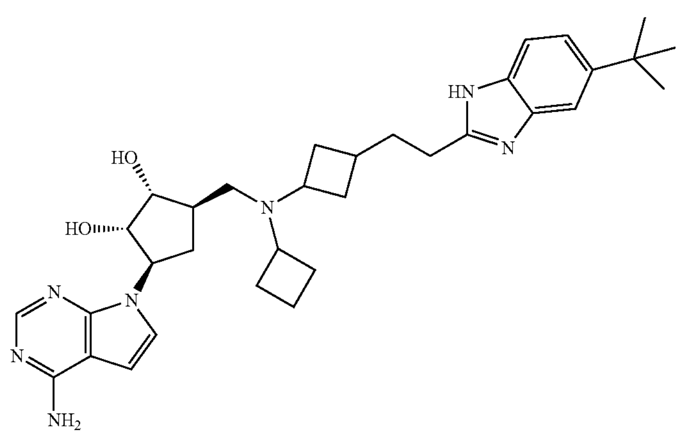 [SMILES: CC(C)(C)c1ccc2[nH]c(CCC3CC(N(C[C@H]4C[C@@H](n5ccc6c(N)ncnc65)[C@H](O)[C@@H]4O)C4CCC4)C3)nc2c1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclobutyl)amino)methyl)cyclopentane-1,2-diol | 572.2 (M + H)+ |

TABLE 1-continued

| Cmpd No. | Structure | Chemical Name | Data (MS or NMR) |
|---|---|---|---|
| A44 | 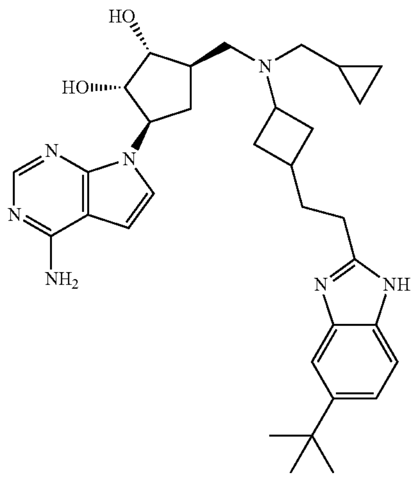 [SMILES: CC(C)(C)c1ccc2[nH]c(CCC3CC(N(CC4CC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclopropylmethyl)amino)methyl)cyclopentane-1,2-diol | 572.6 (M + H)+ |
| A45 | 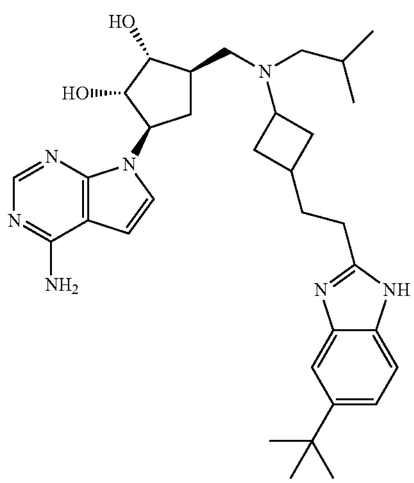 [SMILES: CC(C)CN(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isobutyl)amino)methyl)cyclopentane-1,2-diol | 574.6 (M + H)+ |
| A46 | 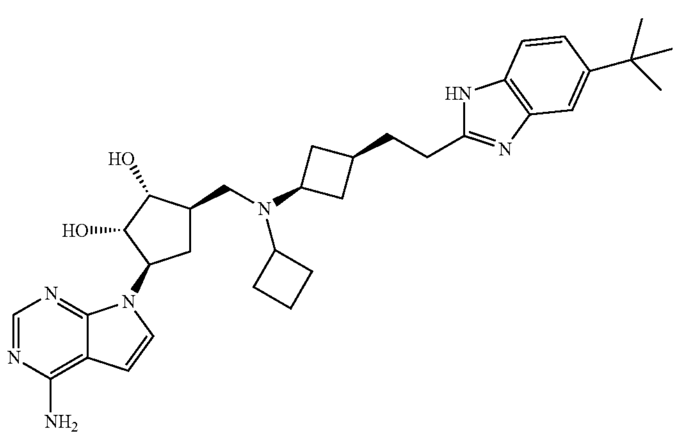 [SMILES: CC(C)(C)c1ccc2[nH]c(CC[C@H]3C[C@@H](N(C[C@H]4C[C@@H](n5ccc6c(N)ncnc65)[C@H](O)[C@@H]4O)C4CCC4)C3)nc2c1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclobutyl)amino)methyl)cyclopentane-1,2-diol | 572.6 (M + H)+ |

TABLE 1-continued

| Cmpd No. | Structure | Chemical Name | Data (MS or NMR) |
|---|---|---|---|
| A47 | 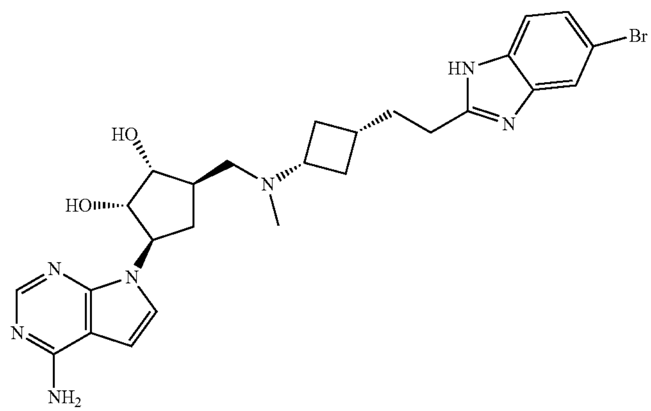 [SMILES: CN(C[C@H]1C[C@@H](n2ccc3c(N)ncnc32)[C@H](O)[C@@H]1O)[C@H]1C[C@@H](CCc2nc3cc(Br)ccc3[nH]2)C1] | (1R,2S,3R,5R)-3-(4-amino-7H-pyrrolo[2,3-d]pyrimidin-7-yl)-5-((((1r,3S)-3-(2-(5-bromo-1H-benzo[d]imidazol-2-yl)ethyl)cyclobutyl)(methyl)amino)methyl)cyclopentane-1,2-diol | 556.0 (M + H)+ |
| A48 | 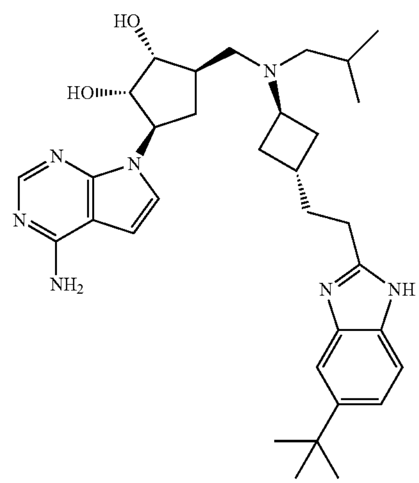 [SMILES: CC(C)CN(C[C@H]1C[C@@H](n2ccc3c(N)ncnc32)[C@H](O)[C@@H]1O)[C@H]1C[C@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(isobutyl)amino)methyl)cyclopentane-1,2-diol | 572.3 (M − H)− |
| A49 | 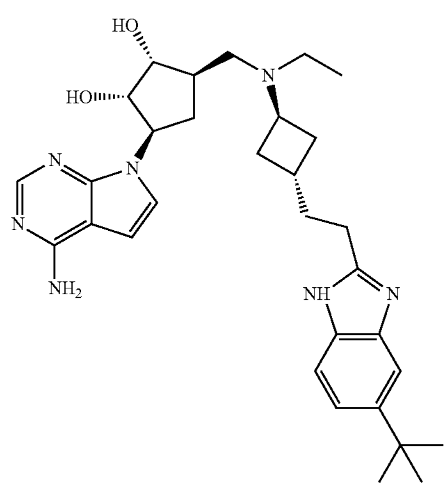 | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(ethyl)amino)methyl)cyclopentane-1,2-diol | 546.3 (M + H)+ |

TABLE 1-continued

| Cmpd No. | Structure | Chemical Name | Data (MS or NMR) |
|---|---|---|---|
| A50 | 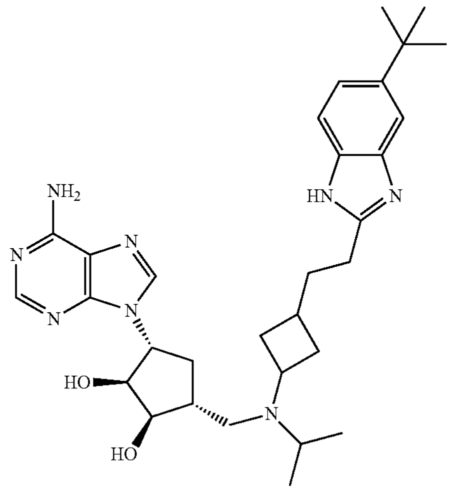 [SMILES: CC(C)N(C[C@H]1C[C@@H](n2cnc3c(N)ncnc32)[C@H](O)[C@@H]1O)C1CC(CCc2nc3cc(C(C)(C)C)ccc3[nH]2)C1] | (1R,2S,3R,5R)-3-(6-amino-9H-purin-9-yl)-5-(((3-(2-(5-(tert-butyl)-1H-benzo[d]imidazol-2-yl)ethyl)cyclobutyl)(isopropyl)amino)methyl)cyclopentane-1,2-diol | 561.4 (M + H)+ |
| A51 | 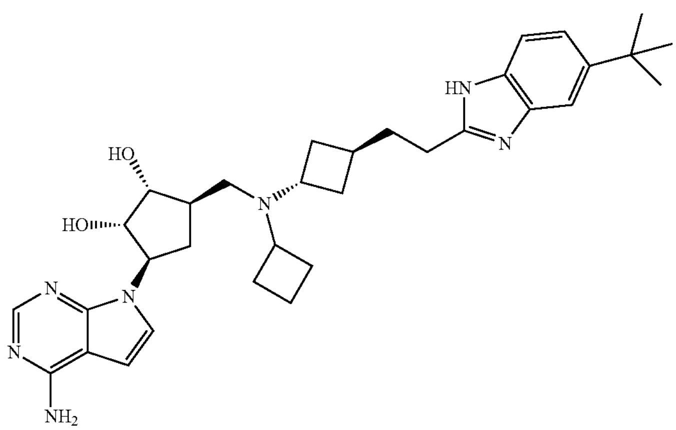 [SMILES: CC(C)(C)c1ccc2[nH]c(CC[C@H]3C[C@H](N(C[C@H]4C[C@@H](n5ccc6c(N)ncnc65)[C@H](O)[C@@H]4O)C4CCC4)C3)nc2c1] | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(cyclobutyl)amino)methyl)cyclopentane-1,2-diol | 572.7 (M + H)+ |
| A52 | 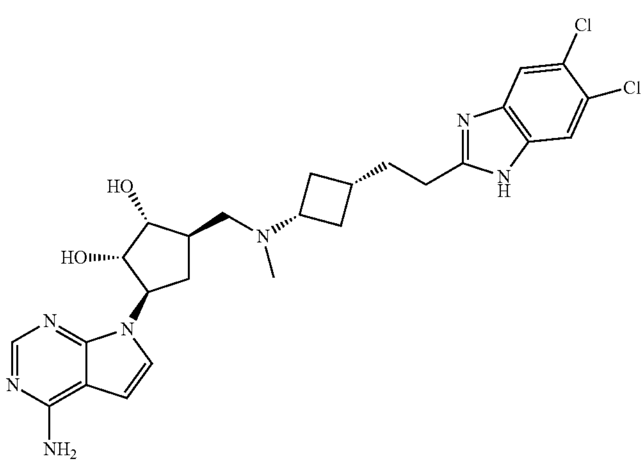 [SMILES: CN(C[C@H]1C[C@@H](n2ccc3c(N)ncnc32)[C@H](O)[C@@H]1O)[C@H]1C[C@@H](CCc2nc3cc(Cl)c(Cl)cc3[nH]2)C1] | (1R,2S,3R,5R)-3-(4-amino-7H-pyrrolo[2,3-d]pyrimidin-7-yl)-5-(((((1r,3S)-3-(2-(5,6-dichloro-1H-benzo[d]imidazol-2-yl)ethyl)cyclobutyl)(methyl)amino)methyl)cyclopentane-1,2-diol | NMR data |

TABLE 1-continued

| Cmpd No. | Structure | Chemical Name | Data (MS or NMR) |
|---|---|---|---|
| A53 | 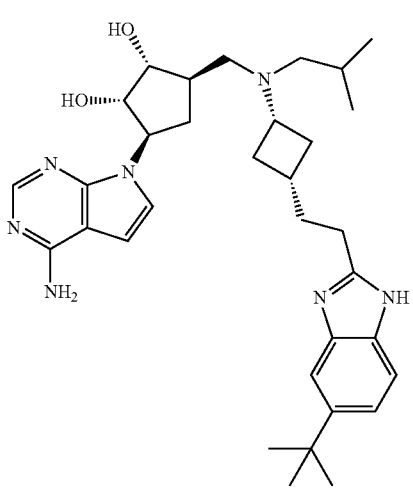 [SMILES: CC(C)CN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isobutyl)amino)methyl)cyclopentane-1,2-diol | 572.3 (M − H)⁻ |
| A54 | 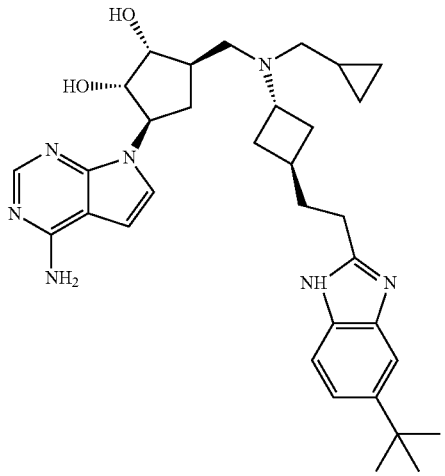 [SMILES: CC(C)(C)c1ccc2[nH]c(CC[C@H]3C[C@H](N(CC4CC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(cyclopropylmethyl)amino)methyl)cyclopentane-1,2-diol | NMR data |
| A55 | 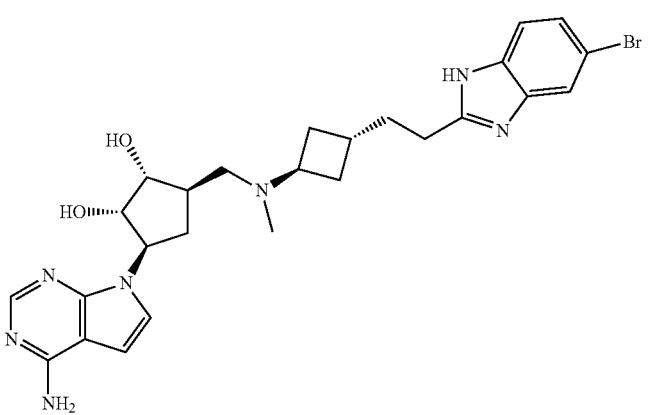 [SMILES: CN(C[C@H]1C[C@@H](n2ccc3c(N)ncnc32)[C@H](O)[C@@H]1O)[C@H]1C[C@H](CCc2nc3cc(Br)ccc3[nH]2)C1] | (1R,2S,3R,5R)-3-(4-amino-7H-pyrrolo[2,3-d]pyrimidin-7-yl)-5-((((1s,3R)-3-(2-(5-bromo-1H-benzo[d]imidazol-2-yl)ethyl)cyclobutyl)(methyl)amino)methyl)cyclopentane-1,2-diol | NMR data |

TABLE 1-continued

| Cmpd No. | Structure | Chemical Name | Data (MS or NMR) |
|---|---|---|---|
| A56 | 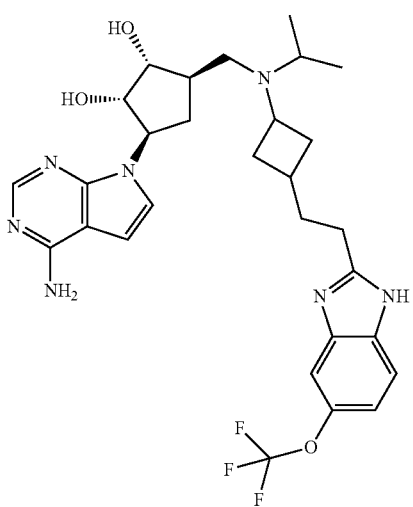 [SMILES: CC(C)N(C[C@H]1C[C@@H](n2ccc3c(N)ncnc32)[C@H](O)[C@@H]1O)C1CC(CCc2nc3cc(OC(F)(F)F)ccc3[nH]2)C1] | (1R,2S,3R,5R)-3-(4-amino-7H-pyrrolo[2,3-d]pyrimidin-7-yl)-5-((isopropyl(3-(2-(5-(trifluoromethoxy)-1H-benzo[d]imidazol-2-yl)ethyl)cyclobutyl)amino)methyl)cyclopentane-1,2-diol | 588.2 (M + H)+ |
| A57 | 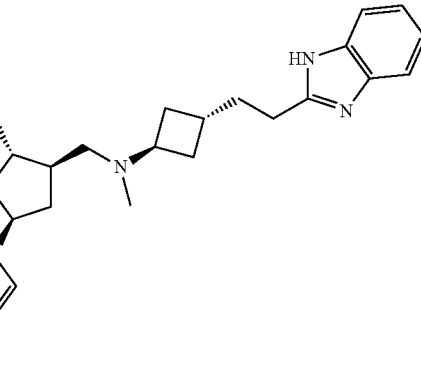 | (1R,2S,3R,5R)-3-(4-amino-7H-pyrrolo[2,3-d]pyrimidin-7-yl)-5-((methyl((1s,3R)-3-(2-(5-(trifluoromethoxy)-1H-benzo[d]imidazol-2-yl)ethyl)cyclobutyl)amino)methyl)cyclopentane-1,2-diol | 560.1 (M + H)+ |
| A58 | 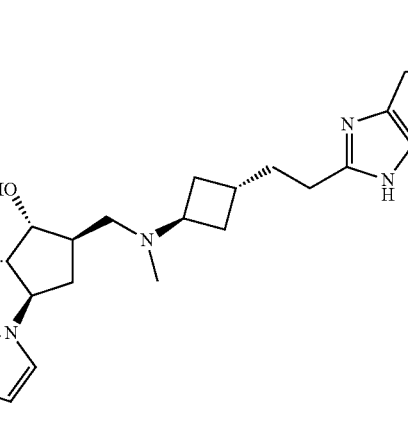 | (1R,2S,3R,5R)-3-(4-amino-7H-pyrrolo[2,3-d]pyrimidin-7-yl)-5-((((1s,3R)-3-(2-(5,6-dichloro-1H-benzo[d]imidazol-2-yl)ethyl)cyclobutyl)(methyl)amino)methyl)cyclopentane-1,2-diol | NMR data |

TABLE 1-continued

| Cmpd No. | Structure | Chemical Name | Data (MS or NMR) |
|---|---|---|---|
| A59 | 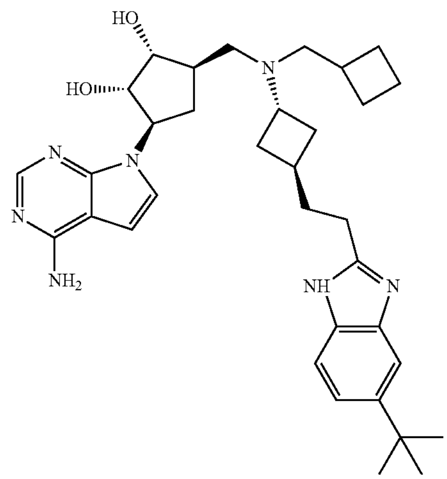 [SMILES: CC(C)(C)c1ccc2[nH]c(CC[C@H]3C[C@H](N(CC4CCC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(cyclobutylmethyl)amino)methyl)cyclopentane-1,2-diol | 586.4 (M + H)+ |
| A60 | 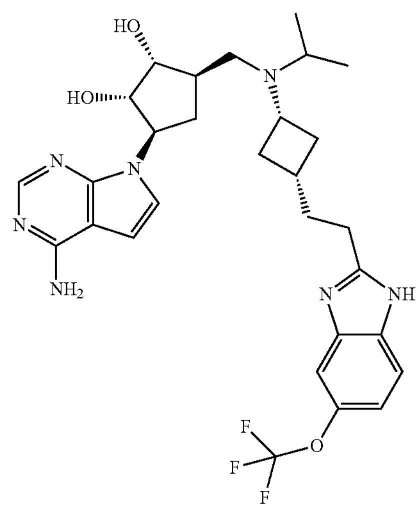 [SMILES: CC(C)N(C[C@H]1C[C@@H](n2ccc3c(N)ncnc32)[C@H](O)[C@@H]1O)[C@H]1C[C@@H](CCc2nc3cc(OC(F)(F)F)ccc3[nH]2)C1] | (1R,2S,3R,5R)-3-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)cyclopentane-1,2-diol | 588.2 (M + H)+ |
| A61 | 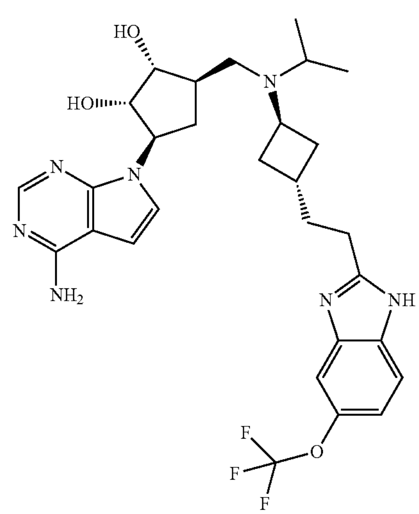 [SMILES: CC(C)N(C[C@H]1C[C@@H](n2ccc3c(N)ncnc32)[C@H](O)[C@@H]1O)[C@H]1C[C@H](CCc2nc3cc(OC(F)(F)F)ccc3[nH]2)C1] | (1R,2S,3R,5R)-3-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)cyclopentane-1,2-diol | 588.7 (M + H)+ |

TABLE 1-continued

| Cmpd No. | Structure | Chemical Name | Data (MS or NMR) |
|---|---|---|---|
| A62 | 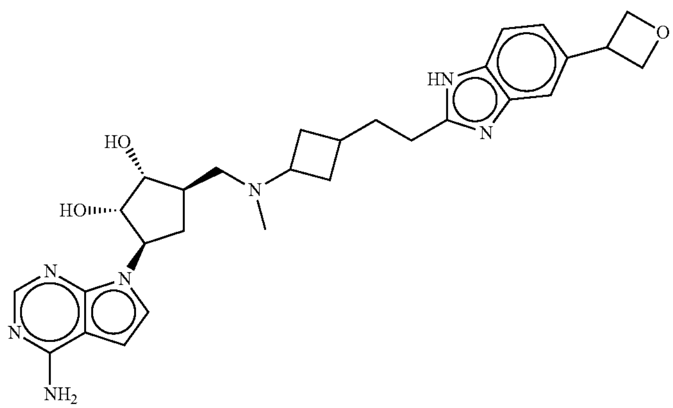 | (1R,2S,3R,5R)-3-(4-amino-7H-pyrrolo[2,3-d]pyrimidin-7-yl)-5-((methyl(3-(2-(5-(oxetan-3-yl)-1H-benzo[d]imidazol-2-yl)ethyl)cyclobutyl)amino)methyl)cyclopentane-1,2-diol | NMR data |
| A63 | 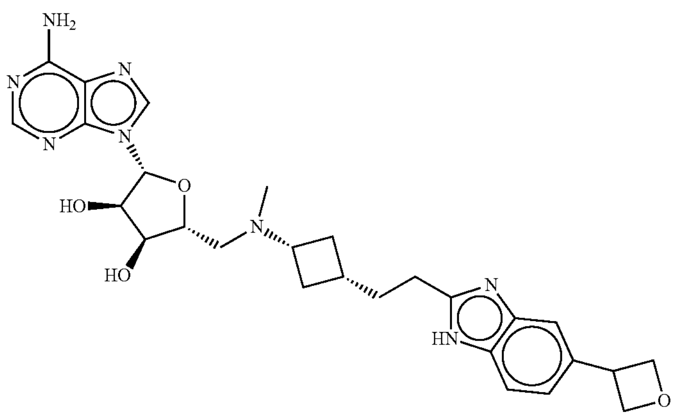 | (2R,3R,4S,5R)-2-(6-amino-9H-purin-9-yl)-5-((methyl((1r,3S)-3-(2-(5-(oxetan-3-yl)-1H-benzo[d]imidazol-2-yl)ethyl)cyclobutyl)amino)methyl)tetrahydrofuran-3,4-diol | 535.4 (M + H)+ |
| A64 | 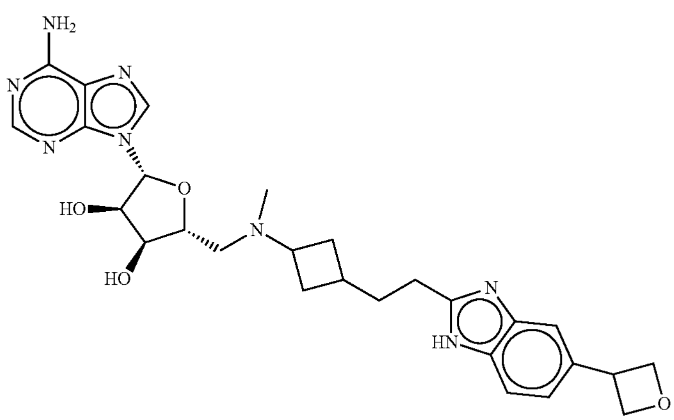 | (2R,3R,4S,5R)-2-(6-amino-9H-purin-9-yl)-5-((methyl(3-(2-(5-(oxetan-3-yl)-1H-benzo[d]imidazol-2-yl)ethyl)cyclobutyl)amino)methyl)tetrahydrofuran-3,4-diol | 535.3 (M + H)+ |

TABLE 1-continued

| Cmpd No. | Structure | Chemical Name | Data (MS or NMR) |
|---|---|---|---|
| A65 | 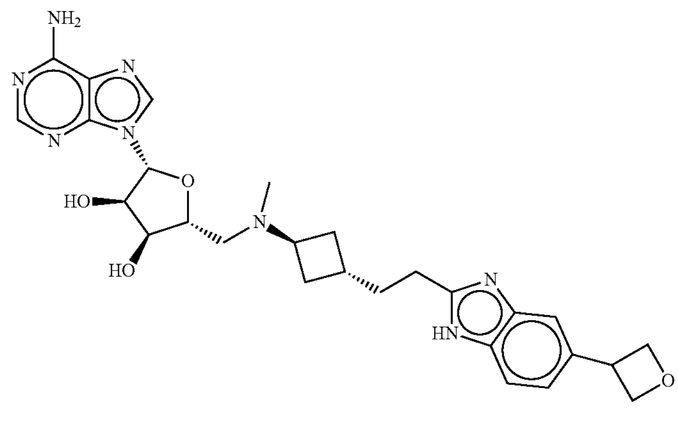 | (2R,3R,4S,5R)-2-(6-amino-9H-purin-9-yl)-5-((methyl((1s,3R)-3-(2-(5-(oxetan-3-yl)-1H-benzo[d]imidazol-2-yl)ethyl)cyclobutyl)amino)methyl)tetrahydrofuran-3,4-diol | 535.4 (M + H)+ |
| A66 | 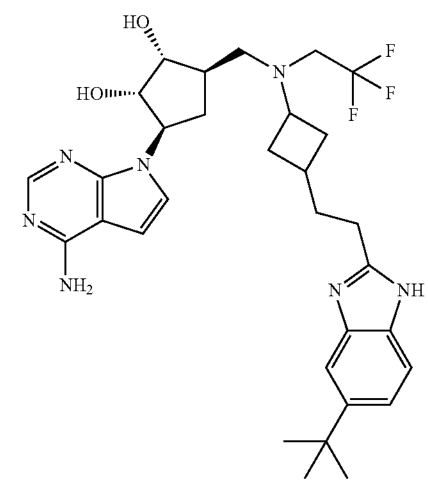 [SMILES: CC(C)(C)c1ccc2[nH]c(CCC3CC(N(C[C@H]4C[C@@H](n5ccc6c(N)ncnc65)[C@H](O)[C@@H]4O)CC(F)(F)F)C3)nc2c1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(2,2,2-trifluoroethyl)amino)methyl)cyclopentane-1,2-diol | 600.2 (M + H)+ |
| A67 | 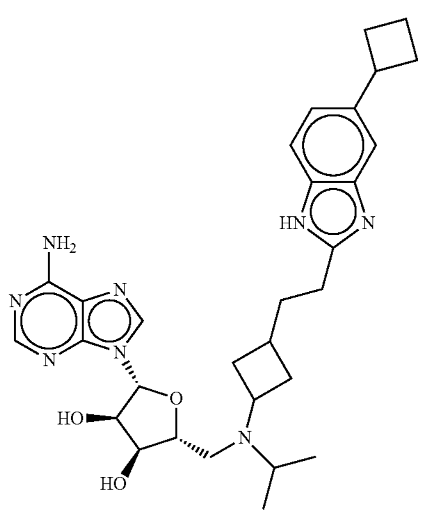 | (2R,3R,4S,5R)-2-(6-amino-9H-purin-9-yl)-5-(((3-(2-(5-cyclobutyl-1H-benzo[d]imidazol-2-yl)ethyl)cyclobutyl)(isopropyl)amino)methyl)tetrahydrofuran-3,4-diol | 561.5 (M + H)+ |

TABLE 1-continued

| Cmpd No. | Structure | Chemical Name | Data (MS or NMR) |
|---|---|---|---|
| A68 | 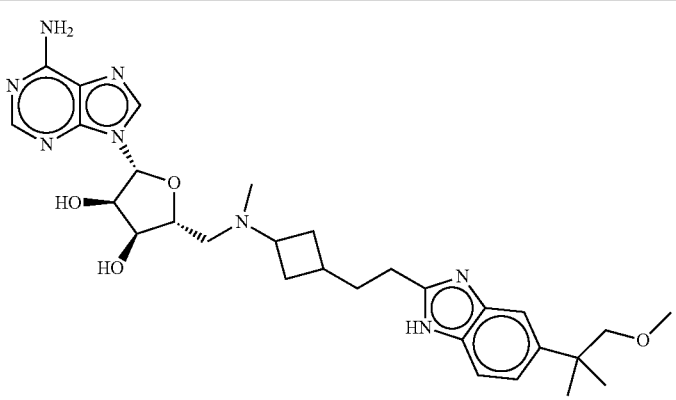 | (2R,3R,4S,5R)-2-(6-amino-9H-purin-9-yl)-5-(((3-(2-(5-(1-methoxy-2-methylpropan-2-yl)-1H-benzo[d]imidazol-2-yl)ethyl)cyclobutyl)(methyl)amino)methyl)tetrahydrofuran-3,4-diol | 565.4 (M + H)+ |
| A69 | 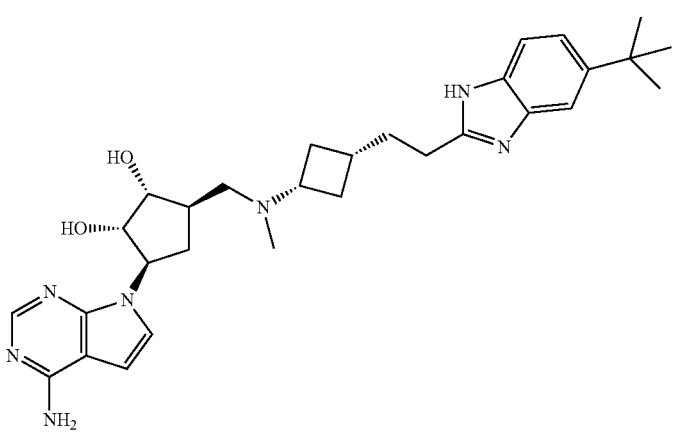 [SMILES: CN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(methyl)amino)methyl)cyclopentane-1,2-diol | 532.3 (M + H)+ |
| A70 | 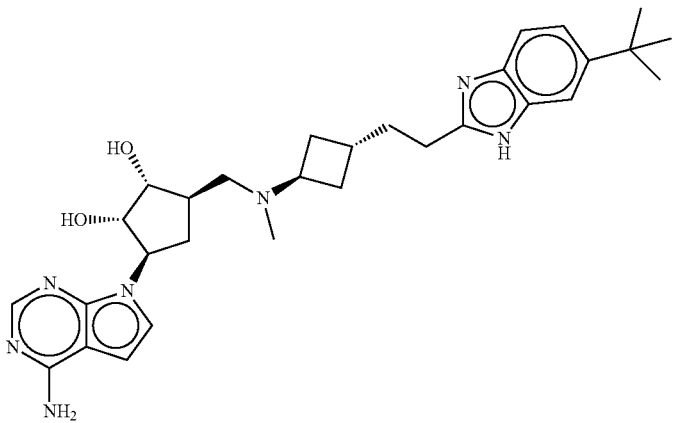 | (1R,2S,3R,5R)-3-(4-amino-7H-pyrrolo[2,3-d]pyrimidin-7-yl)-5-((((1s,3R)-3-(2-(6-tert-butyl)-1H-benzo[d]imidazol-2-yl)ethyl)cyclobutyl)(methyl)amino)methyl)cyclopentane-1,2-diol | 532.3 (M + H)+ |

TABLE 1-continued

| Cmpd No. | Structure | Chemical Name | Data (MS or NMR) |
|---|---|---|---|
| A71 | 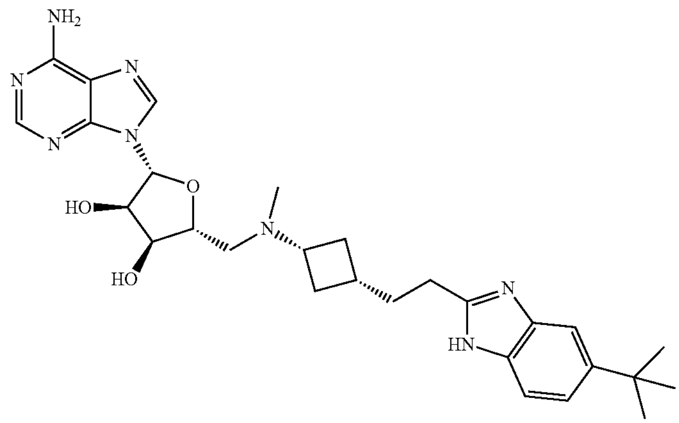 [SMILES: CN(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(methyl)amino)methyl)tetrahydrofuran-3,4-diol | 535.3 (M + H)+ |
| A72 | 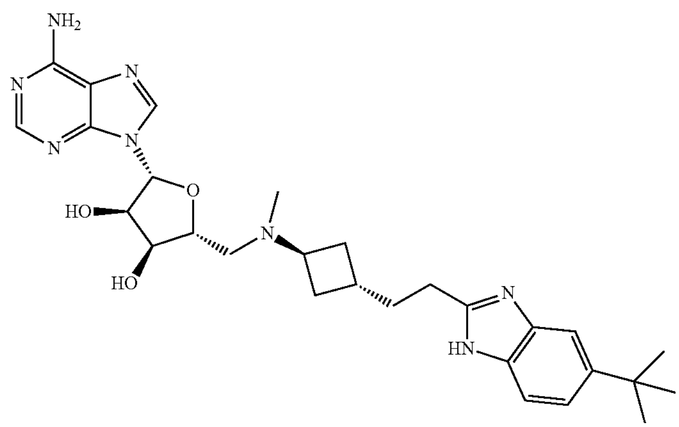 [SMILES: CN(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(methyl)amino)methyl)tetrahydrofuran-3,4-diol | 535.3 (M + H)+ |
| A73 | 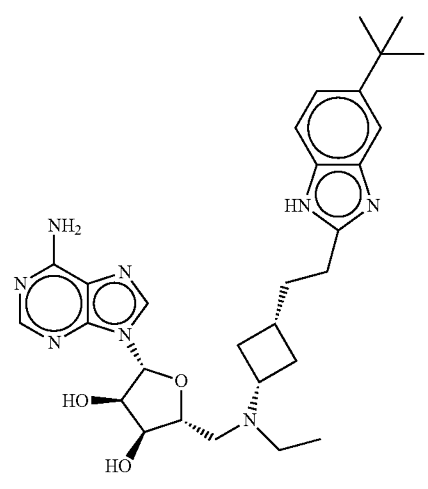 | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(ethyl)amino)methyl)tetrahydrofuran-3,4-diol | 549.3 (M + H)+ |

TABLE 1-continued

| Cmpd No. | Structure | Chemical Name | Data (MS or NMR) |
|---|---|---|---|
| A74 | 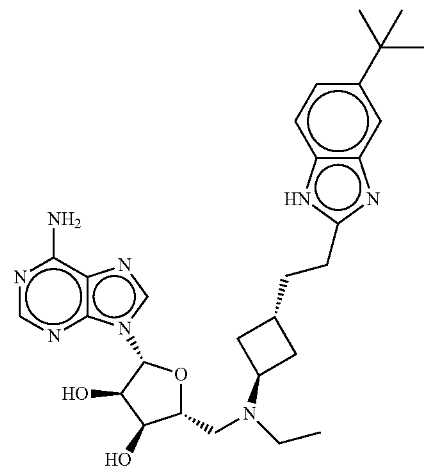 | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(ethyl)amino)methyl)tetrahydrofuran-3,4-diol | 549.3 (M + H)+ |
| A75 | 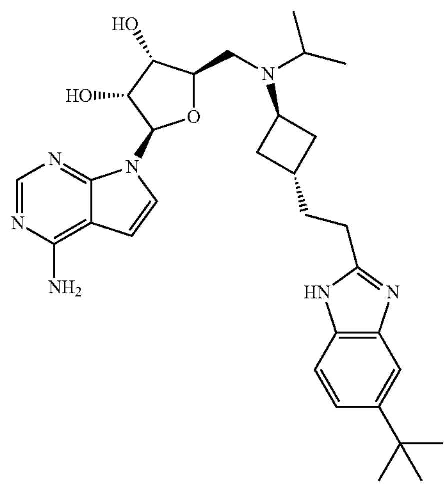 [SMILES: CC(C)N(C[C@H]1O[C@@H](n2ccc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(isopropyl)amino)methyl)tetrahydrofuran-3,4-diol | 562.5 (M + H)+ |
| A76 | 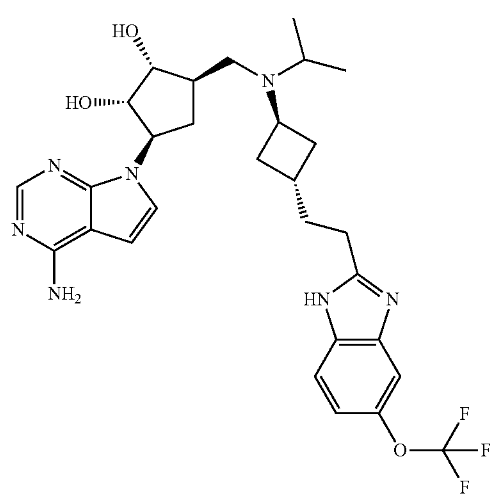 [SMILES: CC(C)N(C[C@H]1C[C@@H](n2ccc3c(N)ncnc32)[C@H](O)[C@@H]1O)[C@H]1C[C@H](CCc2nc3cc(OC(F)(F)F)ccc3[nH]2)C1] | (2R,3R,4S,5R)-2-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol | 590.3 (M + H)+ |

TABLE 1-continued

| Cmpd No. | Structure | Chemical Name | Data (MS or NMR) |
|---|---|---|---|
| A77 | 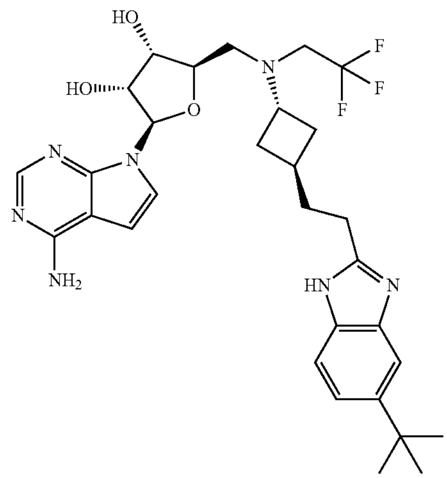 [SMILES: CC(C)(C)c1ccc2[nH]c(CC[C@H]3C[C@H](N(C[C@H]4O[C@@H](n5ccc6c(N)ncnc65)[C@H](O)[C@@H]4O)CC(F)(F)F)C3)nc2c1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 602.3 (M + H)+ |
| A78 | 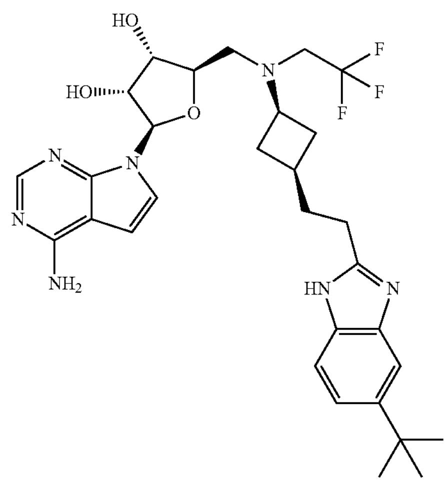 [SMILES: CC(C)(C)c1ccc2[nH]c(CC[C@H]3C[C@@H](N(C[C@H]4O[C@@H](n5ccc6c(N)ncnc65)[C@H](O)[C@@H]4O)CC(F)(F)F)C3)nc2c1] | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 602.3 (M + H)+ |
| A79 | 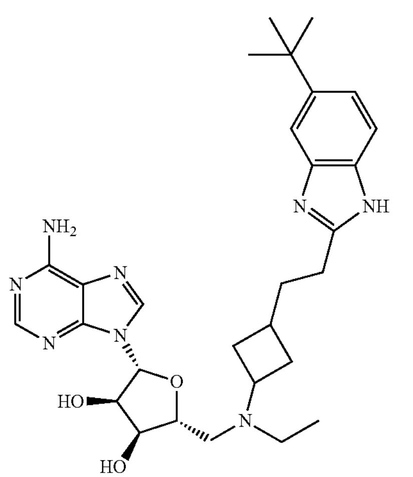 [SMILES: CCN(C[C@H]1O[C@@H](n2cnc3c(N)ncnc32)[C@H](O)[C@@H]1O)C1CC(CCc2nc3cc(C(C)(C)C)ccc3[nH]2)C1] | (2R,3R,4S,5R)-2-(6-amino-9H-purin-9-yl)-5-(((3-(2-(5-(tert-butyl)-1H-benzo[d]imidazol-2-yl)ethyl)cyclobutyl)(ethyl)amino)methyl)tetrahydrofuran-3,4-diol | 549.3 (M + H)+ |

TABLE 1-continued

| Cmpd No. | Structure | Chemical Name | Data (MS or NMR) |
|---|---|---|---|
| A80 | 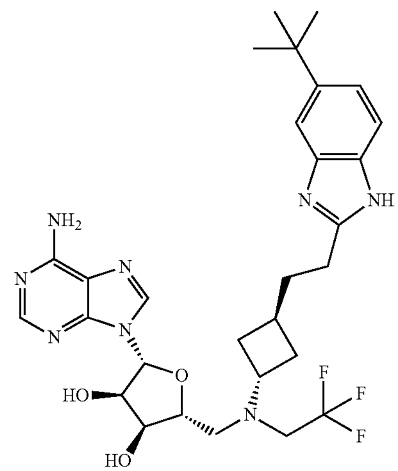 [SMILES: CC(C)(C)c1ccc2[nH]c(CC[C@H]3C[C@H](N(C[C@H]4O[C@@H](n5cnc6c(N)ncnc65)[C@H](O)[C@@H]4O)CC(F)(F)F)C3)nc2c1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 603.3 (M + H)+ |
| A81 | 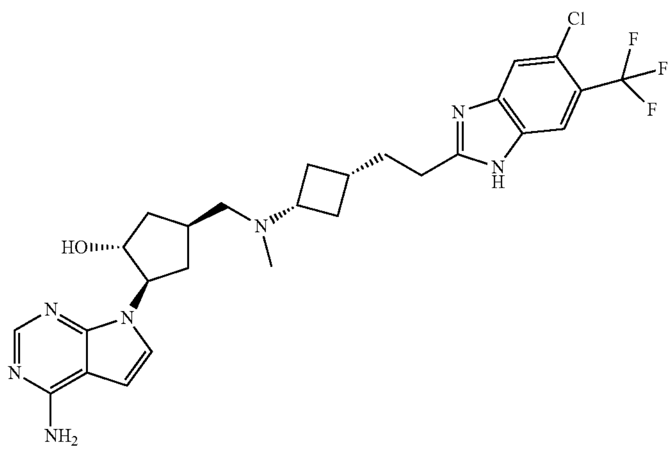 [SMILES: CN(C[C@@H]1C[C@@H](O)[C@H](n2ccc3c(N)ncnc32)C1)[C@H]1C[C@@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1r,3R)-3-(2-(5-chloro-6-(trifluoromethyl)-1H-benzo[d]imidazol-2-yl)ethyl)cyclobutyl)(methyl)amino)methyl)cyclopentanol | 562.3 (M + H)+ |
| A82 | 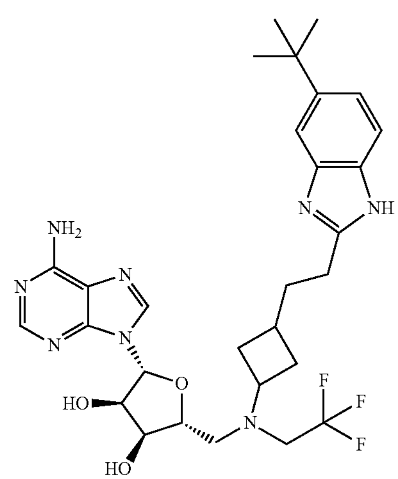 [SMILES: CC(C)(C)c1ccc2[nH]c(CCC3CC(N(C[C@H]4O[C@@H](n5cnc6c(N)ncnc65)[C@H](O)[C@@H]4O)CC(F)(F)F)C3)nc2c1] | (2R,3R,4S,5R)-2-(6-amino-9H-purin-9-yl)-5-(((3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 603.3 (M + H)+ |

TABLE 1-continued

| Cmpd No. | Structure | Chemical Name | Data (MS or NMR) |
|---|---|---|---|
| A83 | 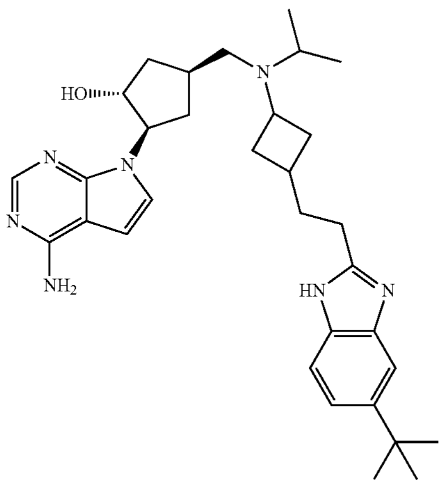 [SMILES: CC(C)N(C[C@@H]1C[C@@H](O)[C@H](n2ccc3c(N)ncnc32)C1)C1CC(CCc2nc3cc(C(C)(C)C)ccc3[nH]2)C1] | (1R,2R,4S)-2-(4-amino-7H-pyrrolo[2,3-d]pyrimidin-7-yl)-4-(((3-(2-(5-(tert-butyl)-1H-benzo[d]imidazol-2-yl)ethyl)cyclobutyl)(isopropyl)amino)methyl)cyclopentanol | 544.5 (M + H)+ |
| A84 | 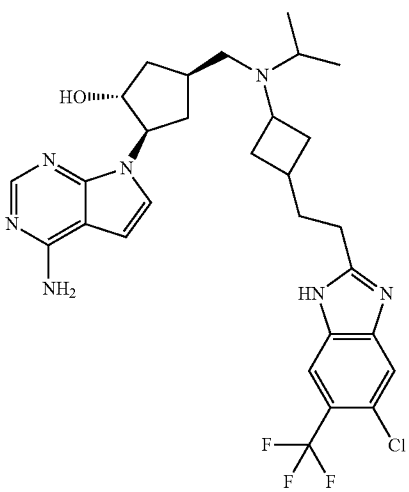 [SMILES: CC(C)N(C[C@@H]1C[C@@H](O)[C@H](n2ccc3c(N)ncnc32)C1)C1CC(CCc2nc3cc(Cl)c(C(F)(F)F)cc3[nH]2)C1] | (1R,2R,4S)-2-(4-amino-7H-pyrrolo[2,3-d]pyrimidin-7-yl)-4-(((3-(2-(5-chloro-6-(trifluoromethyl)-1H-benzo[d]imidazol-2-yl)ethyl)cyclobutyl)(isopropyl)amino)methyl)cyclopentanol | 590.3 (M + H)+ |
| A85 | 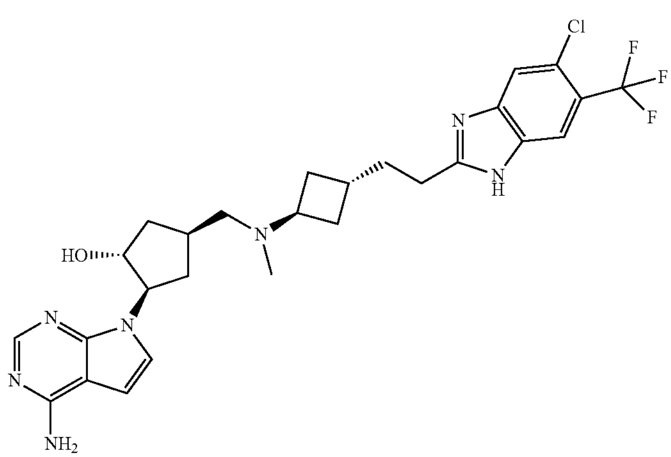 [SMILES: CN(C[C@@H]1C[C@@H](O)[C@H](n2ccc3c(N)ncnc32)C1)[C@H]1C[C@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-(((((1s,3S)-3-(2-(5-chloro-6-(trifluoromethyl)-1H-benzo[d]imidazol-2-yl)ethyl)cyclobutyl)(methyl)amino)methyl)cyclopentanol | 562.3 (M + H)+ |

TABLE 1-continued

| Cmpd No. | Structure | Chemical Name | Data (MS or NMR) |
|---|---|---|---|
| A86 | 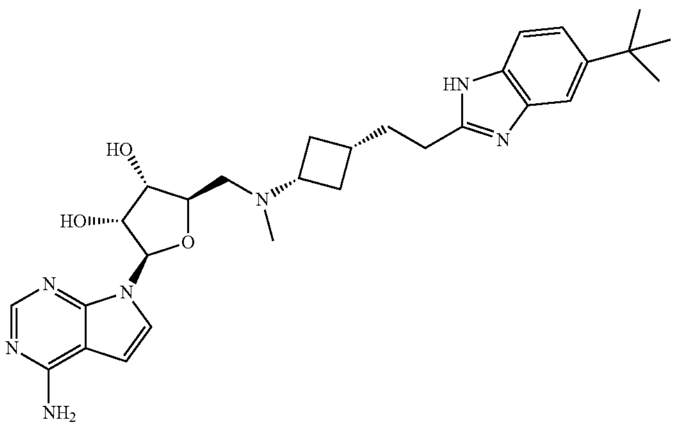 [SMILES: CN(C[C@H]1O[C@@H](n2ccc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(methyl)amino)methyl)tetrahydrofuran-3,4-diol | 534.3 (M + H)+ |
| A87 | 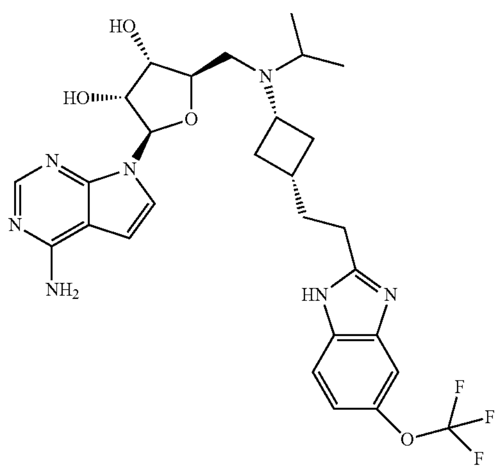 [SMILES: CC(C)N(C[C@H]1O[C@@H](n2ccc3c(N)ncnc32)[C@H](O)[C@@H]1O)[C@H]1C[C@@H](CCc2nc3cc(OC(F)(F)F)ccc3[nH]2)C1] | (2R,3R,4S,5R)-2-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol | 590.3 (M + H)+ |
| A88 | 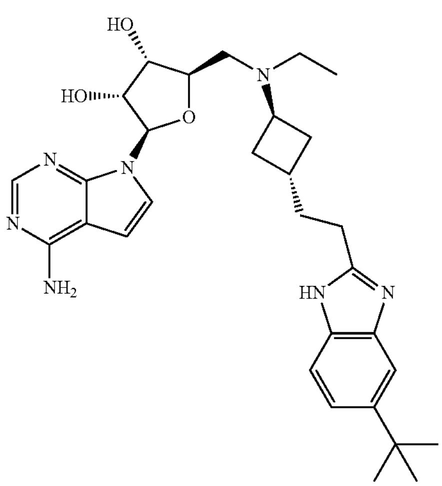 [SMILES: CCN(C[C@H]1O[C@@H](n2ccc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(ethyl)amino)methyl)tetrahydrofuran-3,4-diol | 548.3 (M + H)+ |

TABLE 1-continued

| Cmpd No. | Structure | Chemical Name | Data (MS or NMR) |
|---|---|---|---|
| A89 | 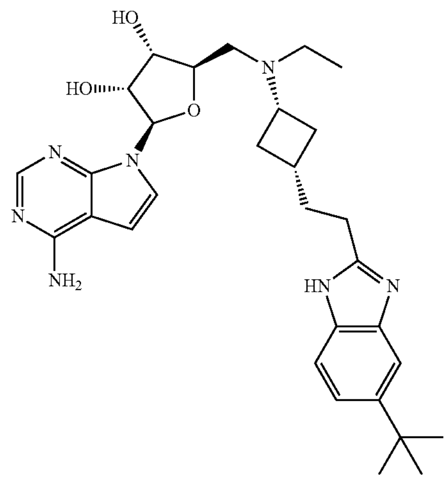 [SMILES: CCN(C[C@H]1O[C@@H](n2ccc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(ethyl)amino)methyl)tetrahydrofuran-3,4-diol | 548.3 (M + H)+ |
| A90 | 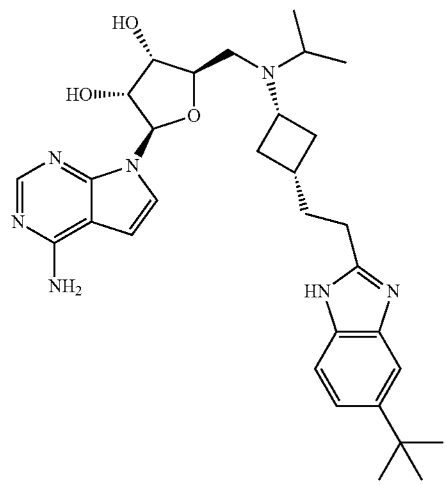 [SMILES: CC(C)N(C[C@H]1O[C@@H](n2ccc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol | 562.5 (M + H)+ |
| A91 | 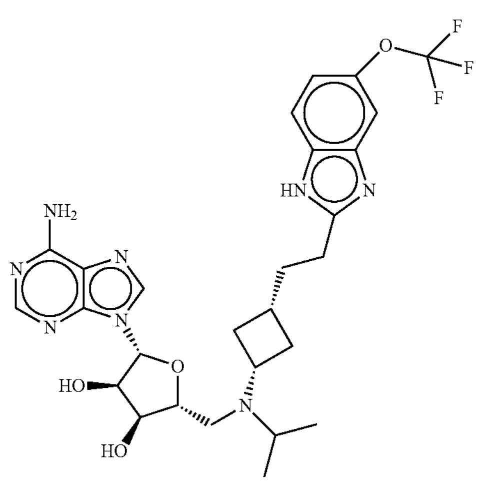 | (2R,3R,4S,5R)-2-(6-amino-9H-purin-9-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol | 591.2 (M + H)+ |

TABLE 1-continued

| Cmpd No. | Structure | Chemical Name | Data (MS or NMR) |
|---|---|---|---|
| A92 | 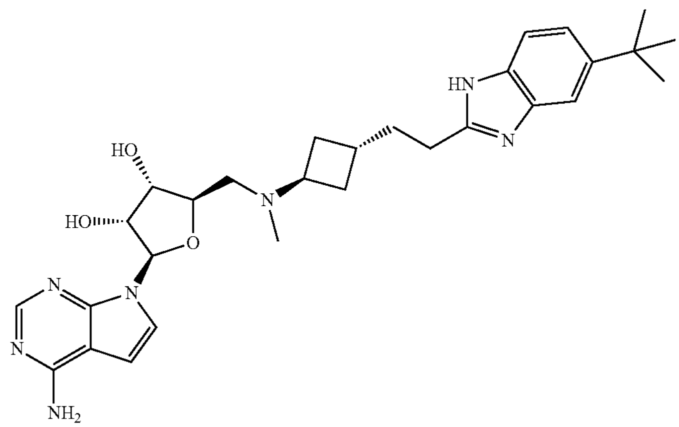 [SMILES: CN(C[C@H]1O[C@@H](n2ccc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)tetrahydrofuran-3,4-diol | 534.3 (M + H)+ |
| A93 | 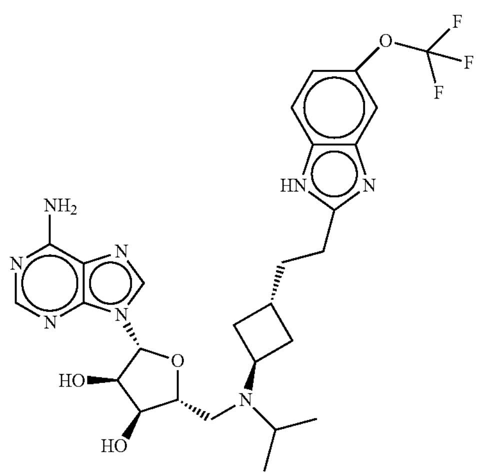 | (2R,3R,4S,5R)-2-(6-amino-9H-purin-9-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol | 591.3 (M + H)+ |
| A94 | 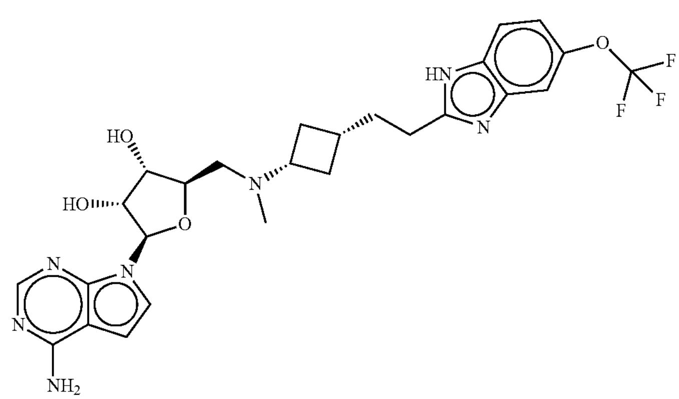 | (2R,3R,4S,5R)-2-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol | 562.2 (M + H)+ |

TABLE 1-continued

| Cmpd No. | Structure | Chemical Name | Data (MS or NMR) |
|---|---|---|---|
| A95 | 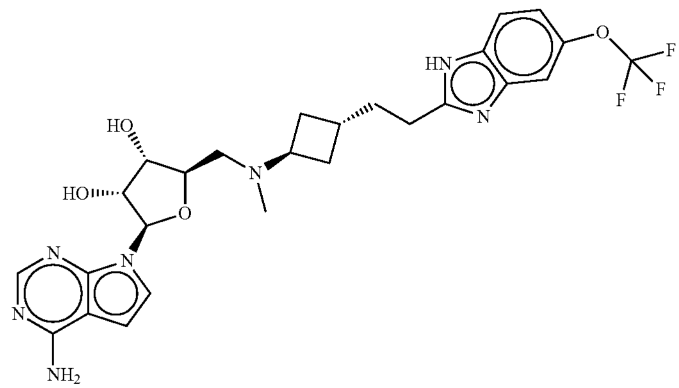 | (2R,3R,4S,5R)-2-(4-amino-7H-pyrrolo[2,3-d]pyrimidin-7-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol | 562.3 (M + H)+ |
| A96 | 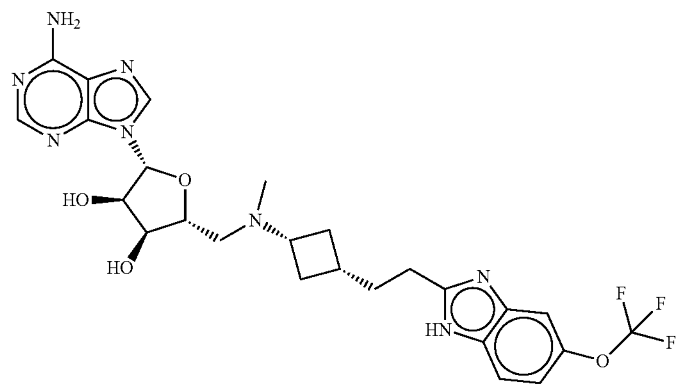 | (2R,3R,4S,5R)-2-(6-amino-9H-purin-9-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol | 563.3 (M + H)+ |
| A97 | 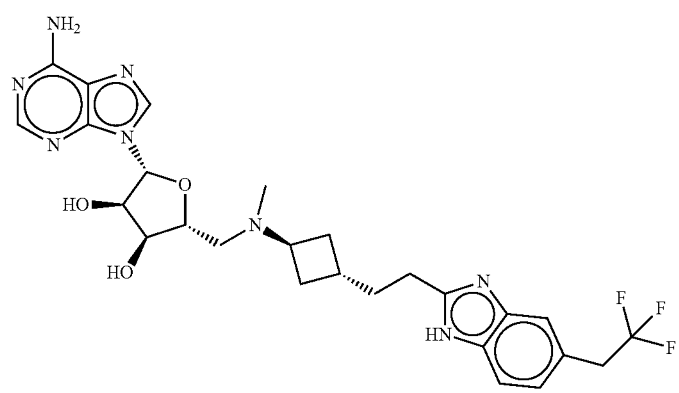 | (2R,3R,4S,5R)-2-(6-amino-9H-purin-9-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol | 563.3 (M + H)+ |
| A98 | 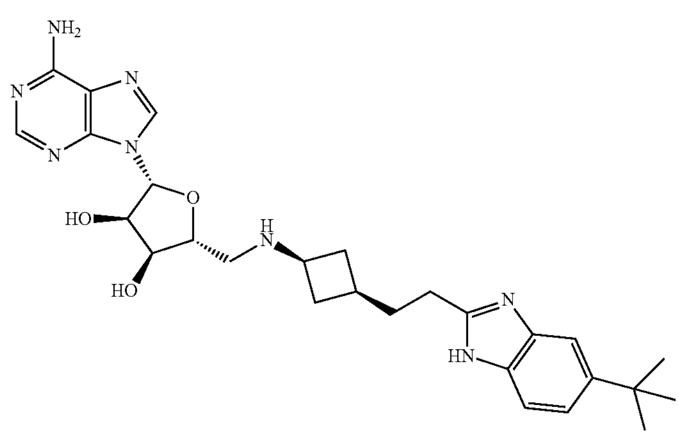 [SMILES: CC(C)(C)c1ccc2[nH]c(CC[C@H]3C[C@@H](NC[C@H]4O[C@@H](n5cnc6c(N)ncnc65)[C@H](O)[C@@H]4O)C3)nc2c1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)amino)methyl)tetrahydrofuran-3,4-diol | 521.3 (M + H)+ |

TABLE 1-continued

| Cmpd No. | Structure | Chemical Name | Data (MS or NMR) |
|---|---|---|---|
| A99 | 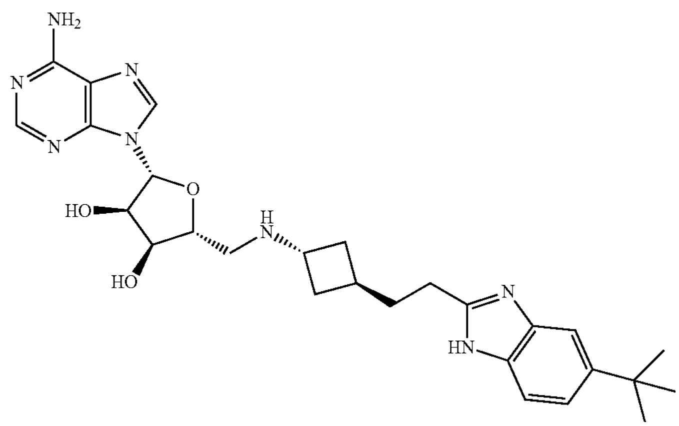 [SMILES: CC(C)(C)c1ccc2[nH]c(CC[C@H]3C[C@H](NC[C@H]4O[C@@H](n5cnc6c(N)ncnc65)[C@H](O)[C@@H]4O)C3)nc2c1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)amino)methyl)tetrahydrofuran-3,4-diol | 521.3 (M + H)+ |
| 1A00 | 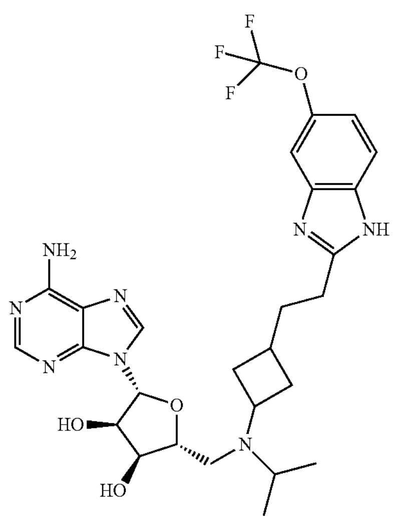 [SMILES: CC(C)N(C[C@H]1O[C@@H](n2cnc3c(N)ncnc32)[C@H](O)[C@@H]1O)C1CC(CCc2nc3cc(OC(F)(F)F)ccc3[nH]2)C1] | (2R,3R,4S,5R)-2-(6-amino-9H-purin-9-yl)-5-((isopropyl(3-(2-(5-(trifluoromethoxy)-1H-benzo[d]imidazol-2-yl)ethyl)cyclobutyl)amino)methyl)tetrahydrofuran-3,4-diol | 591.3 (M + H)+ |
| A101 | 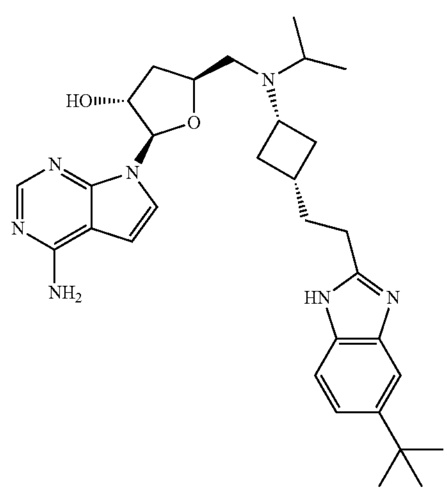 [SMILES: CC(C)N(C[C@@H]1C[C@@H](O)[C@H](n2ccc3c(N)ncnc32)O1)[C@H]1C[C@@H](CCc2nc3cc(C(C)(C)C)ccc3[nH]2)C1] | (1R,2R,4S)-2-(4-amino-7H-pyrrolo[2,3-d]pyrimidin-7-yl)-4-(((((1r,3R)-3-(2-(5-(tert-butyl)-1H-benzo[d]imidazol-2-yl)ethyl)cyclobutyl)(isopropyl)amino)methyl)cyclopentanol | 544.1 (M + H)+ |

TABLE 1-continued

| Cmpd No. | Structure | Chemical Name | Data (MS or NMR) |
|---|---|---|---|
| A102 | 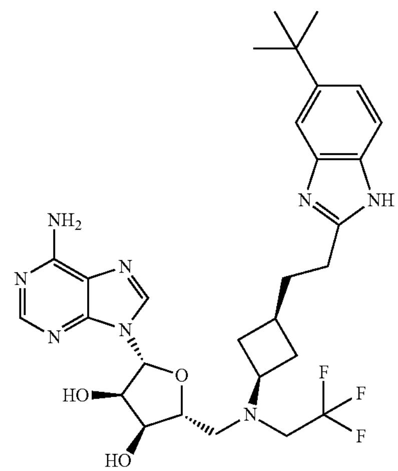 [SMILES: CC(C)(C)c1ccc2[nH]c(CC[C@H]3C[C@@H](N(C[C@H]4O[C@@H](n5cnc6c(N)ncnc65)[C@H](O)[C@@H]4O)CC(F)(F)F)C3)nc2c1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 603.3 (M + H)+ |
| A103 | 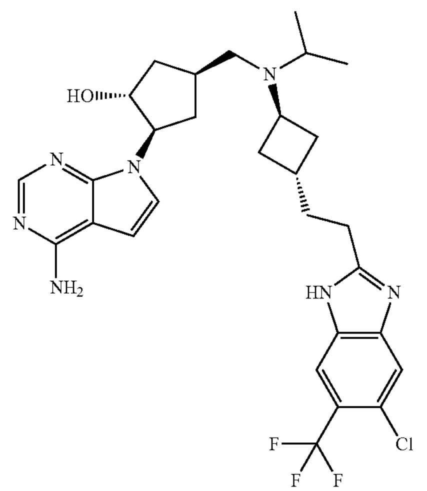 [SMILES: CC(C)N(C[C@@H]1C[C@@H](O)[C@H](n2ccc3c(N)ncnc32)C1)[C@H]1C[C@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1s,3S)-3-(2-(5-chloro-6-(trifluoromethyl)-1H-benzo[d]imidazol-2-yl)ethyl)cyclobutyl)(isopropyl)amino)methyl)cyclopentanol | 589.9 (M + H)+ |
| A104 | 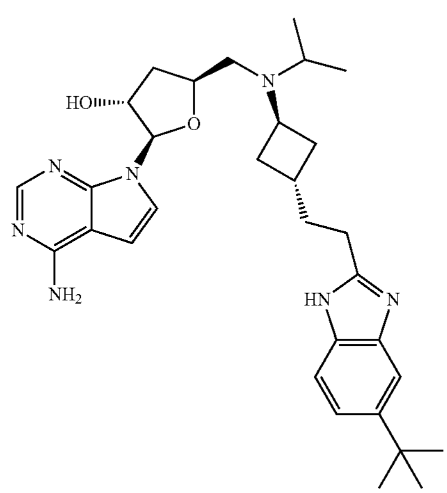 [SMILES: CC(C)N(C[C@@H]1C[C@@H](O)[C@H](n2ccc3c(N)ncnc32)O1)[C@H]1C[C@H](CCc2nc3cc(C(C)(C)C)ccc3[nH]2)C1] | (1R,2R,4S)-2-(4-amino-7H-pyrrolo[2,3-d]pyrimidin-7-yl)-4-((((1s,3S)-3-(2-(5-(tert-butyl)-1H-benzo[d]imidazol-2-yl)ethyl)cyclobutyl)(isopropyl)amino)methyl)cyclopentanol | 544.1 (M + H)+ |

| Cmpd No. | Structure | Chemical Name | Data (MS or NMR) |
|---|---|---|---|
| A105 | 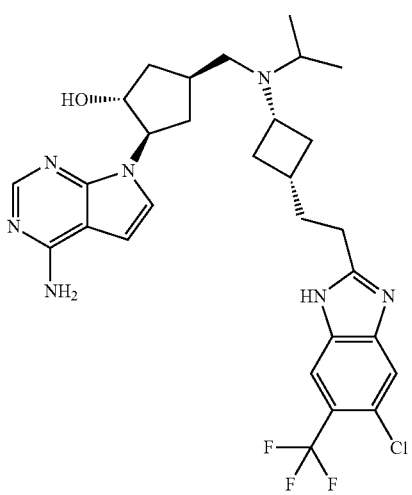 [SMILES: CC(C)N(C[C@@H]1C[C@@H](O)[C@H](n2ccc3c(N)ncnc32)C1)[C@H]1C[C@@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1r,3R)-3-(2-(5-chloro-6-(trifluoromethyl)-1H-benzo[d]imidazol-2-yl)ethyl)cyclobutyl)(isopropyl)amino)methyl)cyclopentanol | 589.9 (M + H)+ |
| A106 | 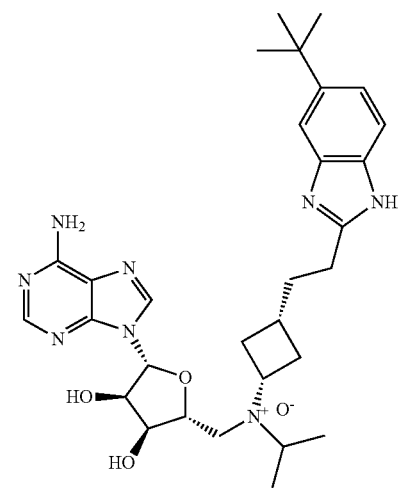 | (1r,3S)-N-(((2R,3S,4R,5R)-5-(6-amino-9H-purin-9-yl)-3,4-dihydroxytetrahydrofuran-2-yl)methyl)-3-(2-(5-(tert-butyl)-1H-benzo[d]imidazol-2-yl)ethyl)-N-isopropylcyclobutanamine oxide | 579.4 (M + H)+ |
| A107 | 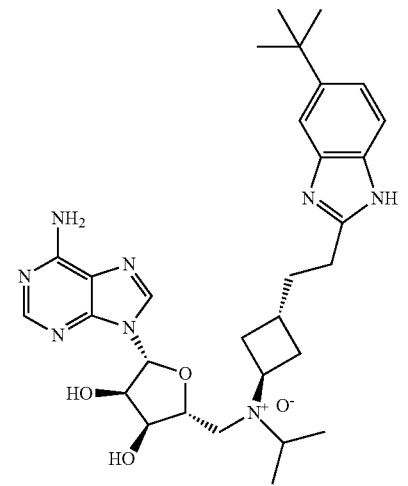 | (R,1s,3R)-N-(((2R,3S,4R,5R)-5-(6-amino-9H-purin-9-yl)-3,4-dihydroxytetrahydrofuran-2-yl)methyl)-3-(2-(5-(tert-butyl)-1H-benzo[d]imidazol-2-yl)ethyl)-N-isopropylcyclobutanamine oxide | 579.4 (M + H)+ |

TABLE 1-continued

| Cmpd No. | Structure | Chemical Name | Data (MS or NMR) |
|---|---|---|---|
| A108 | 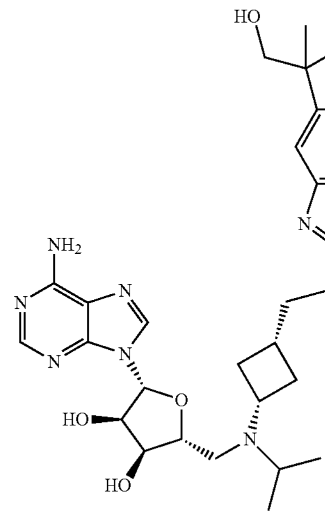 | (2R,3R,4S,5R)-2-(6-amino-9H-purin-9-yl)-5-((((1r,3S)-3-(2-(5-(1-hydroxy-2-methylpropan-2-yl)-1H-benzo[d]imidazol-2-yl)ethyl)cyclobutyl)(isopropyl)amino)methyl)tetrahydrofuran-3,4-diol | 579.4 (M + H)+ |
| A109 | 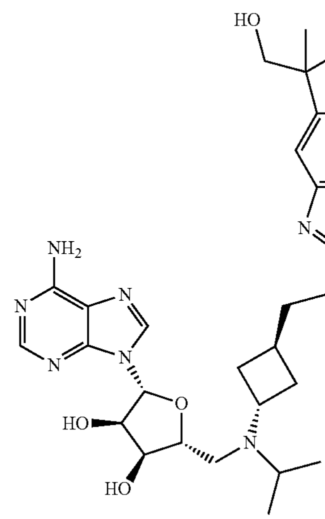 | (2R,3R,4S,5R)-2-(6-amino-9H-purin-9-yl)-5-((((1s,3R)-3-(2-(5-(1-hydroxy-2-methylpropan-2-yl)-1H-benzo[d]imidazol-2-yl)ethyl)cyclobutyl)(isopropyl)amino)methyl)tetrahydrofuran-3,4-diol | 579.4 (M + H)+ |
| A110 | 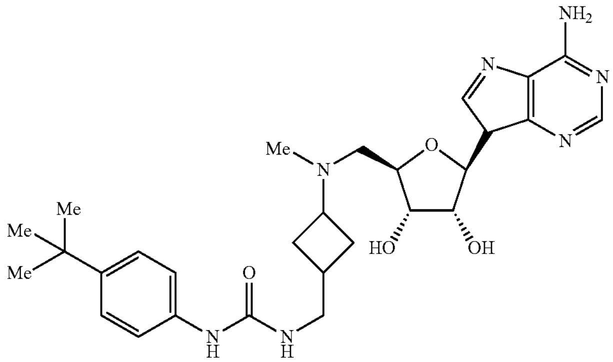 [SMILES: CN(C[C@H]1O[C@@H](C2C=Nc3c(N)ncnc32)[C@H](O)[C@@H]1O)C1CC(CNC(=O)Nc2ccc(C(C)(C)C)cc2)C1] | 1-((3-((((2R,3S,4R,5R)-5-(6-amino-9H-purin-9-yl)-3,4-dihydroxytetrahydrofuran-2-yl)methyl)(methyl)amino)cyclobutyl)methyl)-3-(4-(tert-butyl)phenyl)urea | 539.3 (M + H)+ |

TABLE 1-continued

| Cmpd No. | Structure | Chemical Name | Data (MS or NMR) |
|---|---|---|---|
| A111 | 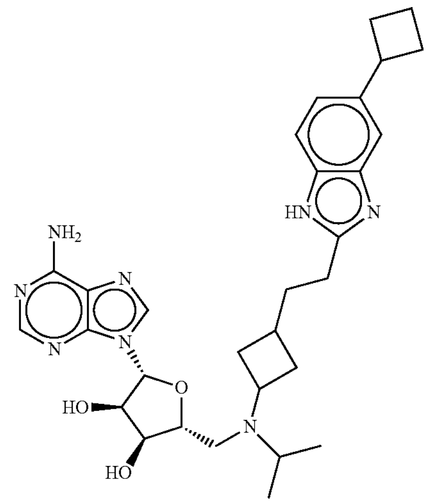 | (2R,3R,4S,5R)-2-(6-amino-9H-purin-9-yl)-5-(((3-(2-(5-cyclobutyl-1H-benzo[d]imidazol-2-yl)ethyl)cyclobutyl)(isopropyl)amino)methyl)tetrahydrofuran-3,4-diol | 561 (M + H)+ |
| A112 | 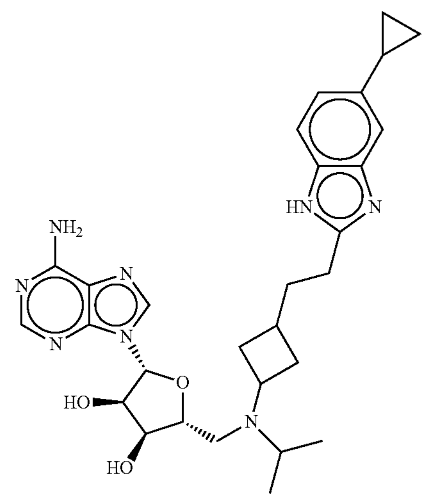 | (2R,3R,4S,5R)-2-(6-amino-9H-purin-9-yl)-5-(((3-(2-(5-cyclopropyl-1H-benzo[d]imidazol-2-yl)ethyl)cyclobutyl)(isopropyl)amino)methyl)tetrahydrofuran-3,4-diol | 547 (M + H)+ |
| A113 | 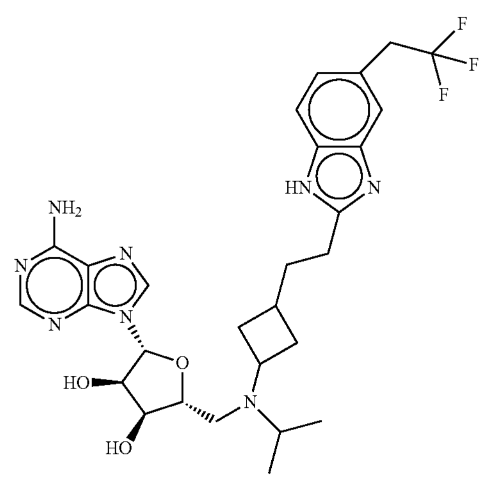 | (2R,3R,4S,5R)-2-(6-amino-9H-purin-9-yl)-5-((isopropyl(3-(2-(5-(2,2,2-trifluoroethyl)-1H-benzo[d]imidazol-2-yl)ethyl)cyclobutyl)amino)methyl)tetrahydrofuran-3,4-diol | 589 (M + H)+ |

TABLE 1-continued

| Cmpd No. | Structure | Chemical Name | Data (MS or NMR) |
|---|---|---|---|
| A114 | 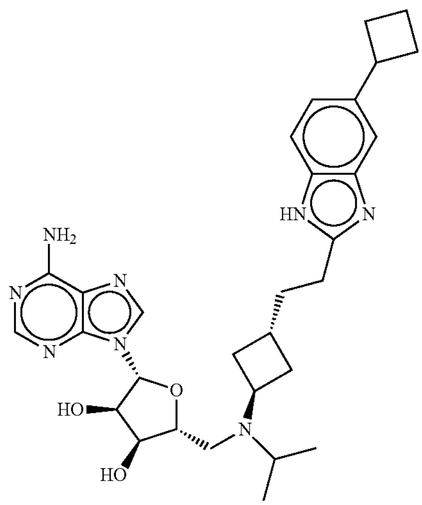 | (2R,3R,4S,5R)-2-(6-amino-9H-purin-9-yl)-5-((((1s,3R)-3-(2-(5-cyclobutyl-1H-benzo[d]imidazol-2-yl)ethyl)cyclobutyl)(isopropyl)amino)methyl)tetrahydrofuran-3,4-diol | 561 (M + H)+ |
| A115 | 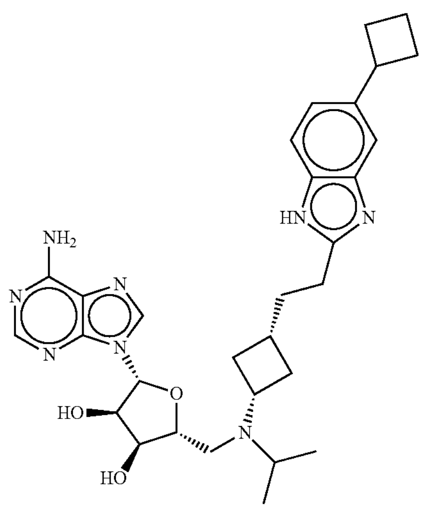 | (2R,3R,4S,5R)-2-(6-amino-9H-purin-9-yl)-5-((((1r,3S)-3-(2-(5-cyclobutyl-1H-benzo[d]imidazol-2-yl)ethyl)cyclobutyl)(isopropyl)amino)methyl)tetrahydrofuran-3,4-diol | 561 (M + H)+ |
| A116 | 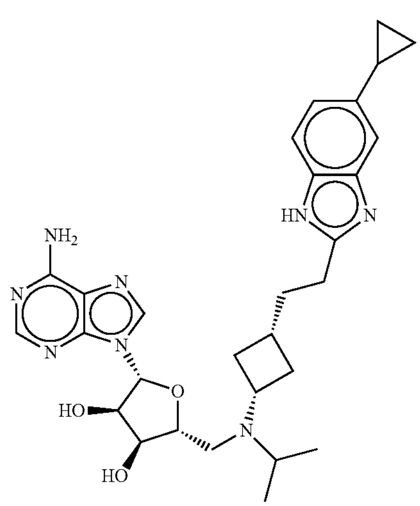 | (2R,3R,4S,5R)-2-(6-amino-9H-purin-9-yl)-5-((((1r,3S)-3-(2-(5-cyclopropyl-1H-benzo[d]imidazol-2-yl)ethyl)cyclobutyl)(isopropyl)amino)methyl)tetrahydrofuran-3,4-diol | 547 (M + H)+ |

TABLE 1-continued

| Cmpd No. | Structure | Chemical Name | Data (MS or NMR) |
|---|---|---|---|
| A117 | 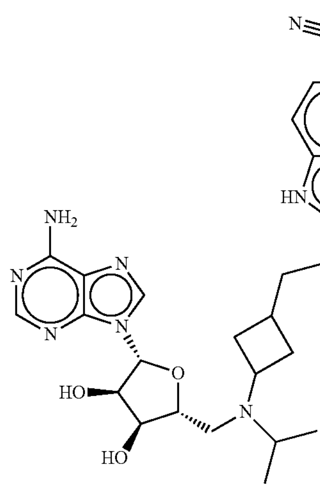 | 1-(2-(2-(3-((((2R,3S,4R,5R)-5-(6-amino-9H-purin-9-yl)-3,4-dihydroxytetrahydrofuran-2-yl)methyl)(isopropyl) amino)cyclobutyl) ethyl)-1H-benzo[d]imidazol-5-yl)cyclobutanecarbonitrile | 586 (M + H)+ |
| A118 | 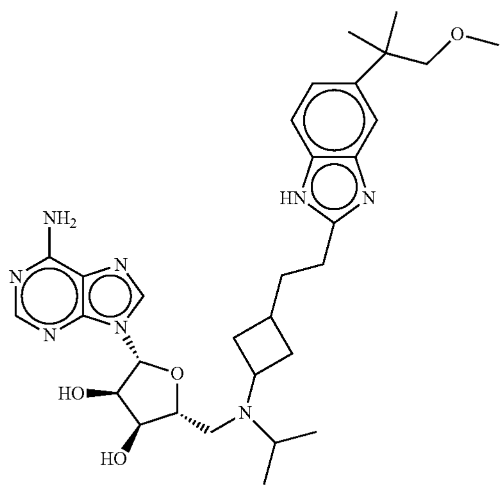 | (2R,3R,4S,5R)-2-(6-amino-9H-purin-9-yl)-5-((isopropyl(3-(2-(5-(1-methoxy-2-methylpropan-2-yl)-1H-benzo[d]imidazol-2-yl)ethyl)cyclobutyl) amino)methyl) tetrahydrofuran-3,4-diol | 593 (M + H)+ |
| A119 | 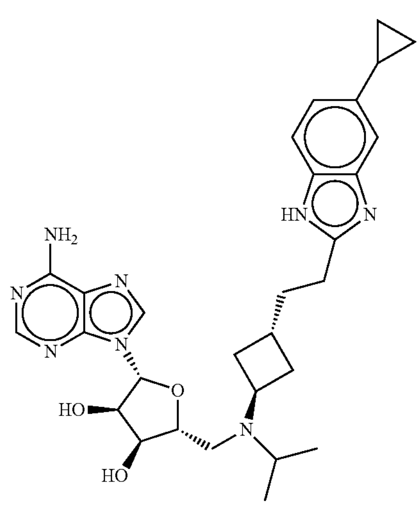 | (2R,3R,4S,5R)-2-(6-amino-9H-purin-9-yl)-5-((((1s,3R)-3-(2-(5-cyclopropyl-1H-benzo[d]imidazol-2-yl)ethyl)cyclobutyl) (isopropyl)amino) methyl)tetrahydrofuran-3,4-diol | 547 (M + H)+ |

| Cmpd No. | Structure | Chemical Name | Data (MS or NMR) |
|---|---|---|---|
| A120 | 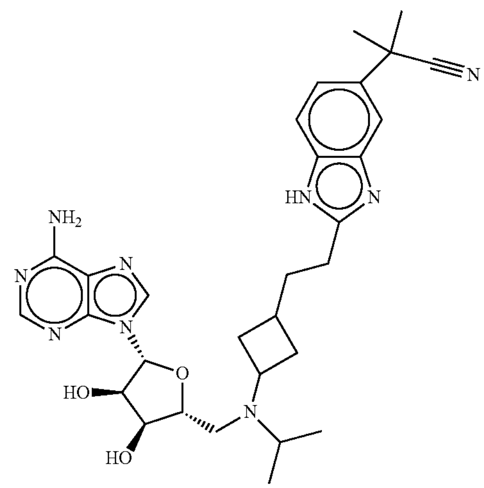 | 2-(2-(2-(3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile | 574 (M + H)+ |
| A121 | 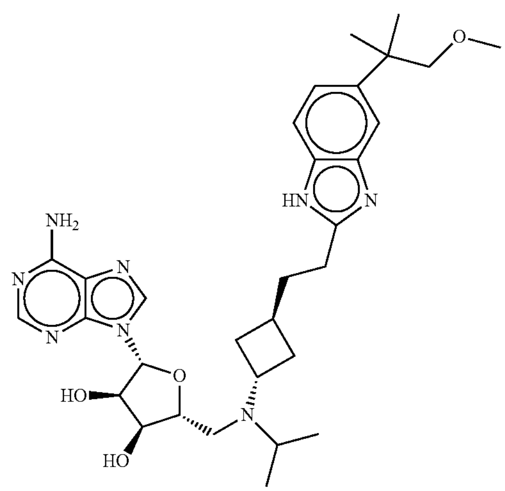 | (2R,3R,4S,5R)-2-(6-amino-9H-purin-9-yl)-5-((isopropyl((1s,3R)-3-(2-(5-(1-methoxy-2-methylpropan-2-yl)-1H-benzo[d]imidazol-2-yl)ethyl)cyclobutyl)amino)methyl)tetrahydrofuran-3,4-diol | 593 (M + H)+ |
| A122 | 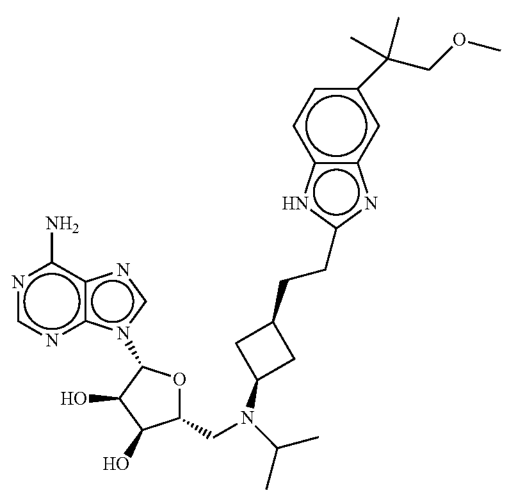 | (2R,3R,4S,5R)-2-(6-amino-9H-purin-9-yl)-5-((isopropyl((1r,3S)-3-(2-(5-(1-methoxy-2-methylpropan-2-yl)-1H-benzo[d]imidazol-2-yl)ethyl)cyclobutyl)amino)methyl)tetrahydrofuran-3,4-diol | 593 (M + H)+ |

TABLE 1-continued

| Cmpd No. | Structure | Chemical Name | Data (MS or NMR) |
|---|---|---|---|
| A123 | 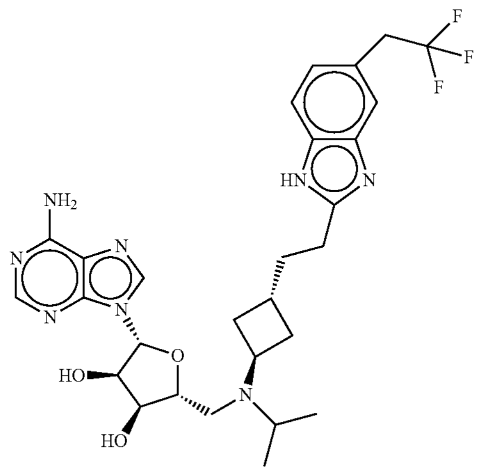 | (2R,3R,4S,5R)-2-(6-amino-9H-purin-9-yl)-5-((isopropyl((1S,3R)-3-(2-(5-(2,2,2-trifluoroethyl)-1H-benzo[d]imidazol-2-yl)ethyl)cyclobutyl)amino)methyl)tetrahydrofuran-3,4-diol | 589 (M + H)+ |
| A124 | 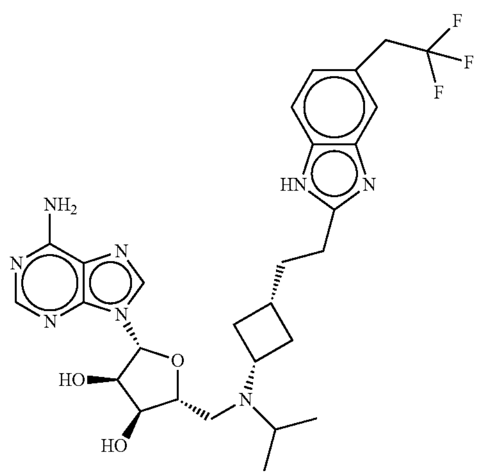 | (2R,3R,4S,5R)-2-(6-amino-9H-purin-9-yl)-5-((isopropyl((1r,3S)-3-(2-(5-(2,2,2-trifluoroethyl)-1H-benzo[d]imidazol-2-yl)ethyl)cyclobutyl)amino)methyl)tetrahydrofuran-3,4-diol | 589 (M + H)+ |
| A125 | 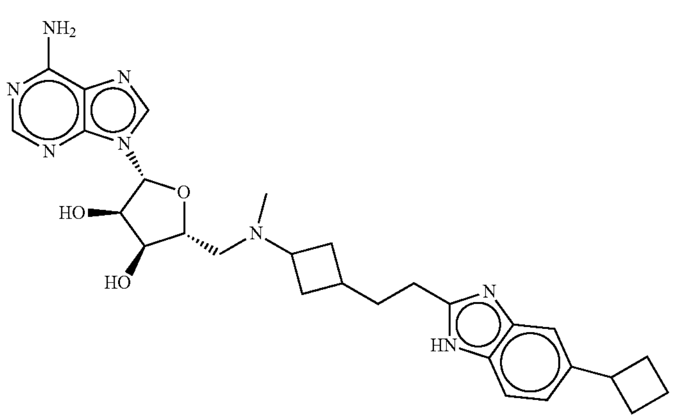 | (2R,3R,4S,5R)-2-(6-amino-9H-purin-9-yl)-5-(((3-(2-(5-cyclobutyl-1H-benzo[d]imidazol-2-yl)ethyl)cyclobutyl)(methyl)amino)methyl)tetrahydrofuran-3,4-diol | 533 (M + H)+ |

TABLE 1-continued

| Cmpd No. | Structure | Chemical Name | Data (MS or NMR) |
|---|---|---|---|
| A126 | 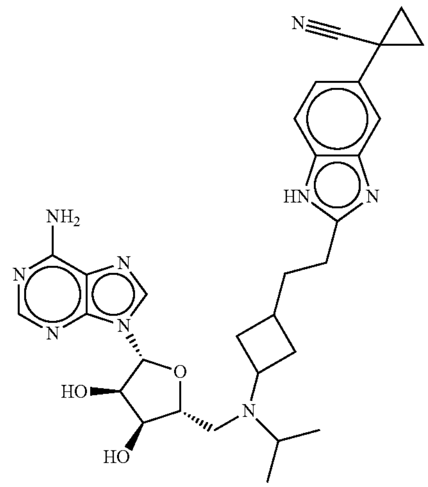 | 1-(2-(2-(3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile | 572 (M + H)+ |
| A127 | 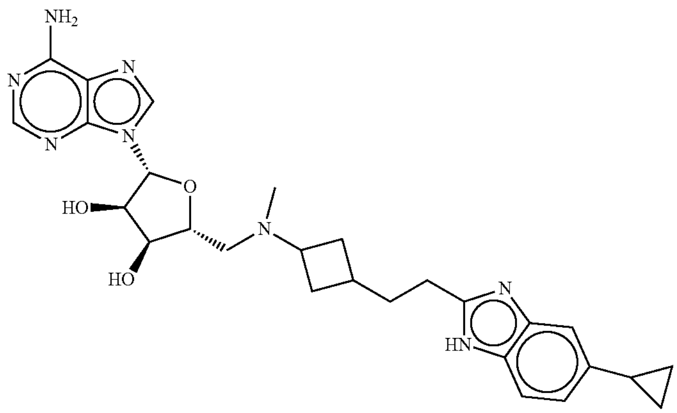 | (2R,3R,4S,5R)-2-(6-amino-9H-purin-9-yl)-5-(((3-(2-(5-cyclopropyl-1H-benzo[d]imidazol-2-yl)ethyl)cyclobutyl)(methyl)amino)methyl)tetrahydrofuran-3,4-diol | 519 (M + H)+ |
| A128 | 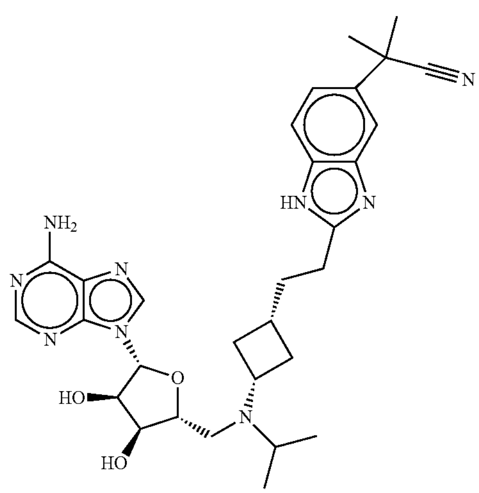 | 2-(2-(2-((1S,3r)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile | 574 (M + H)+ |

TABLE 1-continued

| Cmpd No. | Structure | Chemical Name | Data (MS or NMR) |
|---|---|---|---|
| A129 | 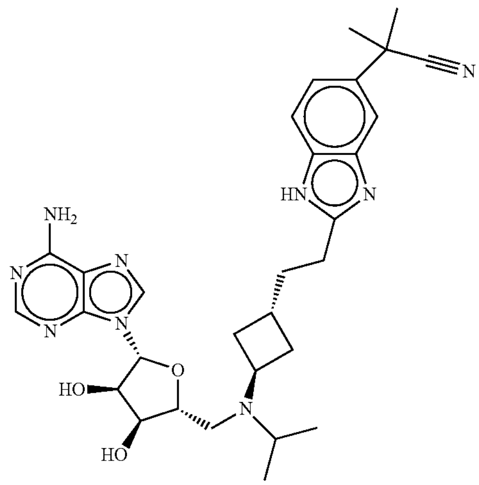 | 2-(2-(2-((1R,3s)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile | 574 (M + H)+ |
| A130 | 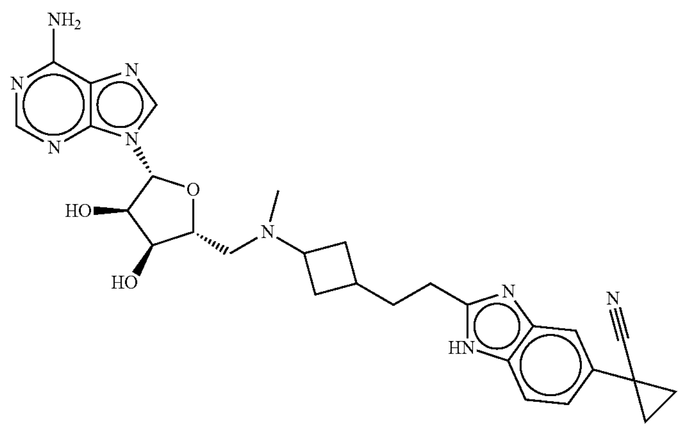 | 1-(2-(2-(3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile | 544 (M + H)+ |
| A131 | 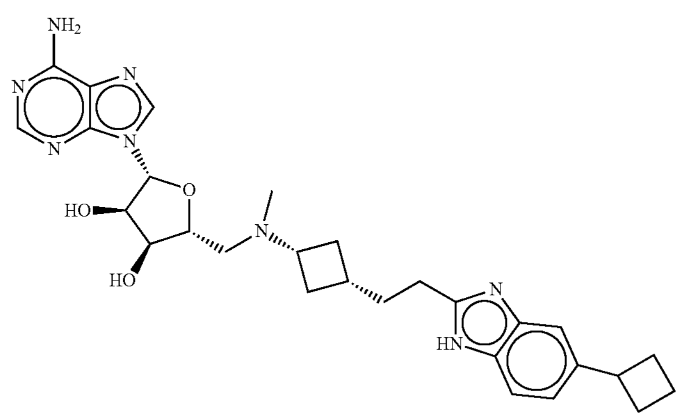 | (2R,3R,4S,5R)-2-(6-amino-9H-purin-9-yl)-5-((((1r,3S)-3-(2-(5-cyclobutyl-1H-benzo[d]imidazol-2-yl)ethyl)cyclobutyl)(methyl)amino)methyl)tetrahydrofuran-3,4-diol | 533 (M + H)+ |

TABLE 1-continued

| Cmpd No. | Structure | Chemical Name | Data (MS or NMR) |
|---|---|---|---|
| A132 | 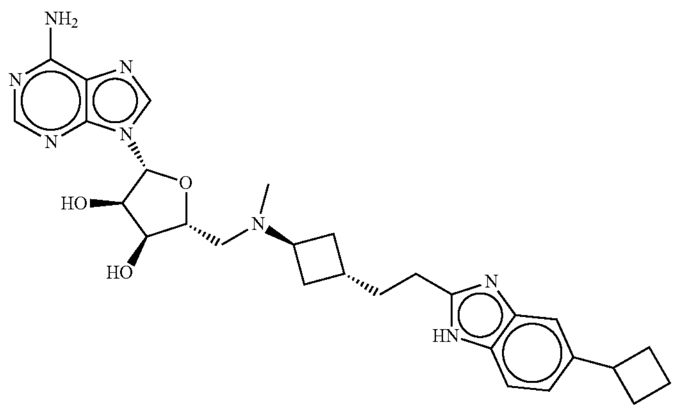 | (2R,3R,4S,5R)-2-(6-amino-9H-purin-9-yl)-5-((((1s,3R)-3-(2-(5-cyclobutyl-1H-benzo[d]imidazol-2-yl)ethyl)cyclobutyl)(methyl)amino)methyl)tetrahydrofuran-3,4-diol | 533 (M + H)+ |
| A133 | 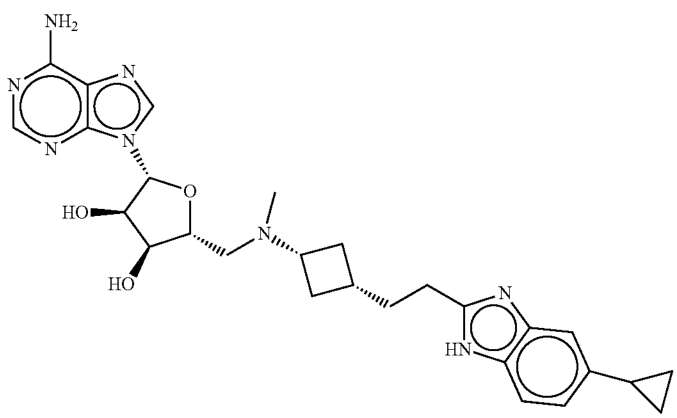 | (2R,3R,4S,5R)-2-(6-amino-9H-purin-9-yl)-5-((((1r,3S)-3-(2-(5-cyclopropyl-1H-benzo[d]imidazol-2-yl)ethyl)cyclobutyl)(methyl)amino)methyl)tetrahydrofuran-3,4-diol | 519 (M + H)+ |
| A134 | 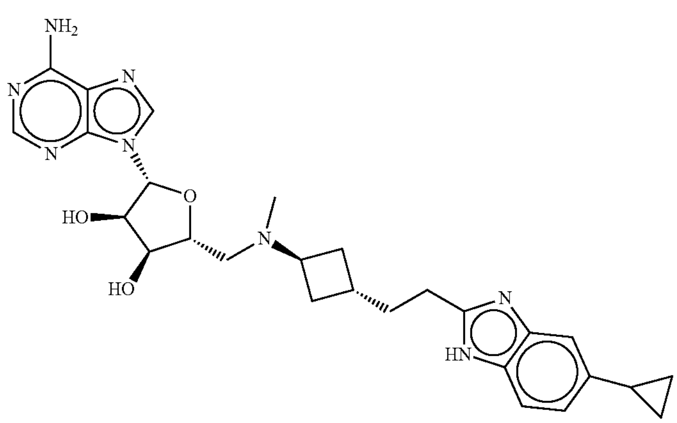 | (2R,3R,4S,5R)-2-(6-amino-9H-purin-9-yl)-5-((((1s,3R)-3-(2-(5-cyclopropyl-1H-benzo[d]imidazol-2-yl)ethyl)cyclobutyl)(methyl)amino)methyl)tetrahydrofuran-3,4-diol | 519 (M + H)+ |

TABLE 1-continued

| Cmpd No. | Structure | Chemical Name | Data (MS or NMR) |
|---|---|---|---|
| A135 | 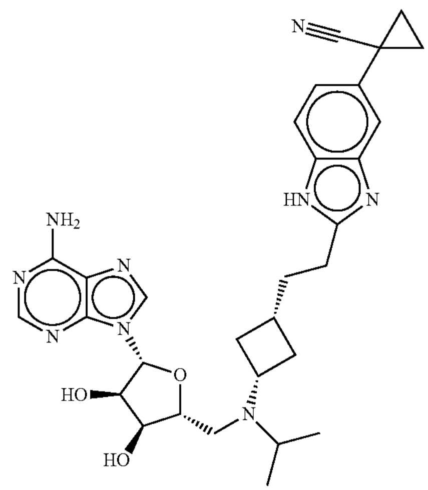 | 1-(2-(2-((1S,3r)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile | 572 (M + H)+ |
| A136 | 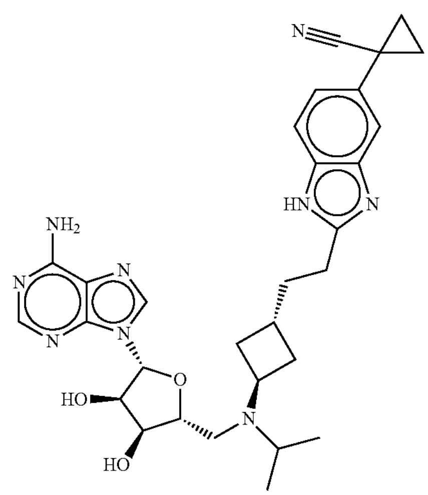 | 1-(2-(2-((1R,3s)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile | 572 (M + H)+ |
| A137 | 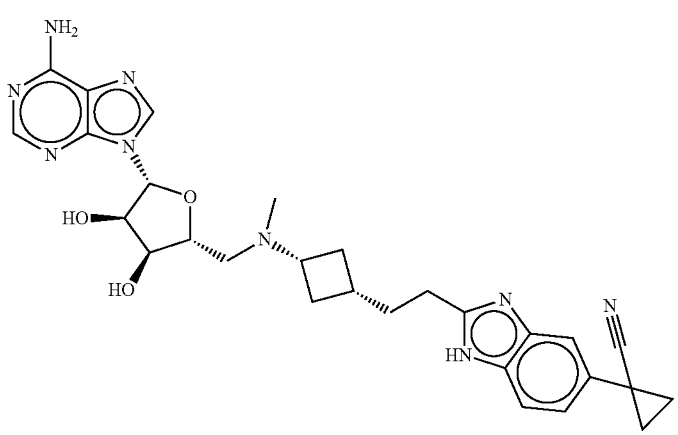 | 1-(2-(2-((1S,3r)-3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile | 544 (M + H)+ |

TABLE 1-continued

| Cmpd No. | Structure | Chemical Name | Data (MS or NMR) |
|---|---|---|---|
| A138 | 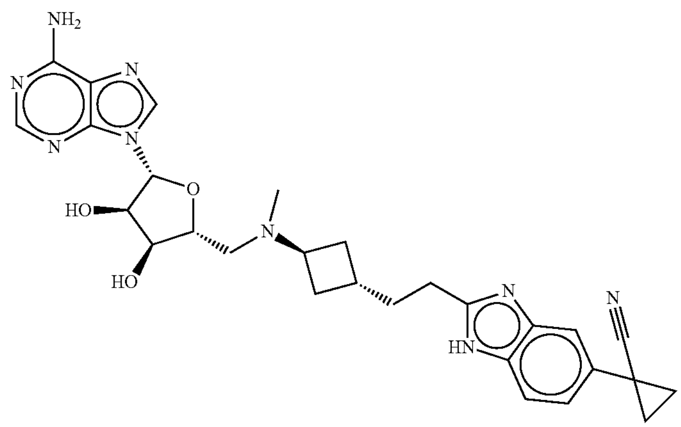 | 1-(2-(2-((1R,3s)-3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropane-carbonitrile | 544 (M + H)+ |
| A139 | 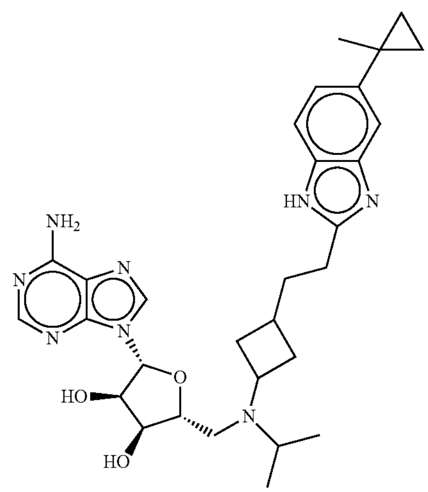 | (2R,3R,4S,5R)-2-(6-amino-9H-purin-9-yl)-5-((isopropyl(3-(2-(5-(1-methylcyclopropyl)-1H-benzo[d]imidazol-2-yl)ethyl)cyclobutyl)amino)methyl)tetrahydrofuran-3,4-diol | 561 (M + H)+ |
| A140 | 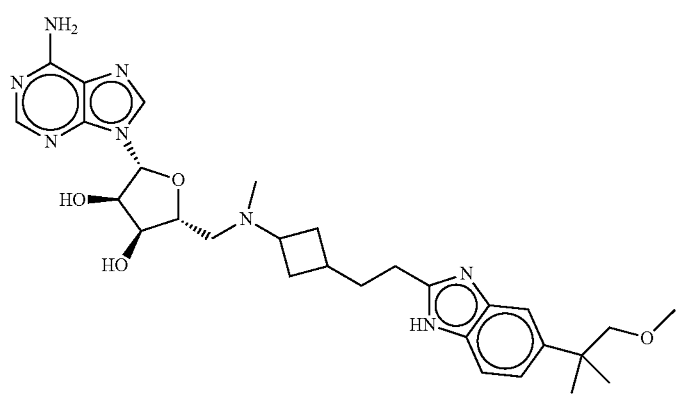 | (2R,3R,4S,5R)-2-(6-amino-9H-purin-9-yl)-5-(((3-(2-(5-(1-methoxy-2-methylpropan-2-yl)-1H-benzo[d]imidazol-2-yl)ethyl)cyclobutyl)(methyl)amino)methyl)tetrahydrofuran-3,4-diol | 565 (M + H)+ |

TABLE 2

| Cmpd. No. | Structures | Chemical Name |
|---|---|---|
| B1 | 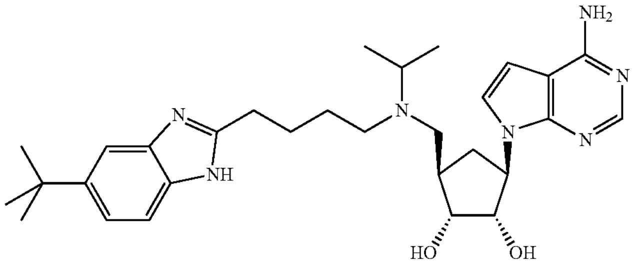 [SMILES: CC(C)N(CCCCc1nc2cc(C(C)(C)C)ccc2[nH]1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-(((4-(5-tert-butyl-1H-benzo[d]imidazol-2-yl)butyl)(isopropyl)amino)methyl)cyclopentane-1,2-diol |
| B2 | 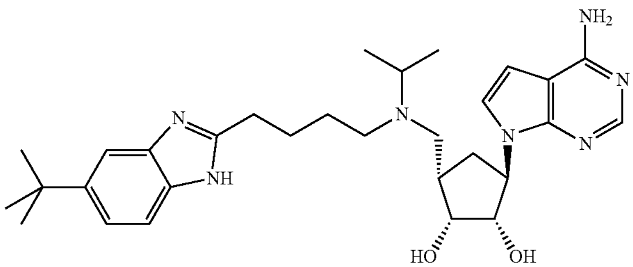 [SMILES: CC(C)N(CCCCc1nc2cc(C(C)(C)C)ccc2[nH]1)C[C@@H]1C[C@@H](n2ccc3c(N)ncnc32)[C@H](O)[C@@H]1O] | (1R,2S,3R,5S)-3-(4-amino-7H-pyrrolo[2,3-d]pyrimidin-7-yl)-5-(((4-(5-tert-butyl-1H-benzo[d]imidazol-2-yl)butyl)(isopropyl)amino)methyl)cyclopentane-1,2-diol |
| B3 | 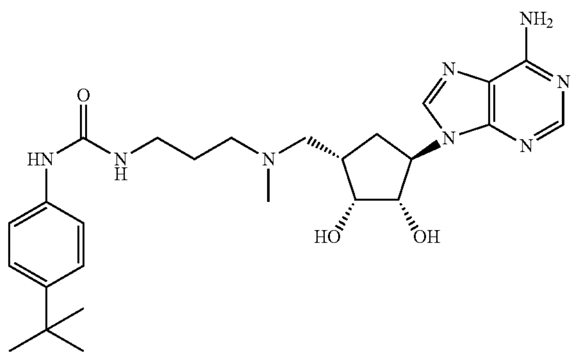 [SMILES: CN(CCCNC(=O)Nc1ccc(C(C)(C)C)cc1)C[C@@H]1C[C@@H](n2cnc3c(N)ncnc32)[C@H](O)[C@@H]1O] | 1-(3-(((((1S,2R,3S,4R)-4-(6-amino-9H-purin-9-yl)-2,3-dihydroxycyclopentyl)methyl)(methyl)amino)propyl)-3-(4-(tert-butyl)phenyl)urea |
| B4 | 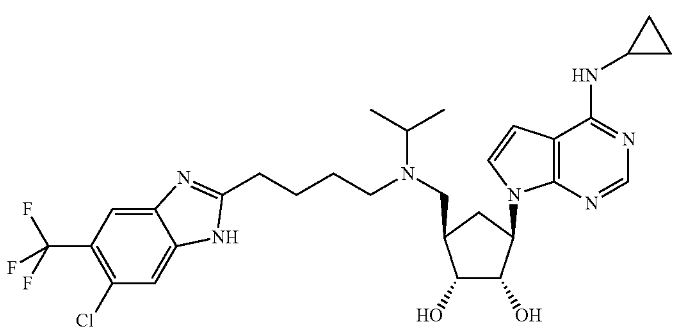 [SMILES: CC(C)N(CCCCc1nc2cc(C(F)(F)F)c(Cl)cc2[nH]1)C[C@H]1C[C@@H](n2ccc3c(NC4CC4)ncnc32)[C@H](O)[C@@H]1O] | (1S,2R,3R,5R)-3-(((4-(6-chloro-5-(trifluoromethyl)-1H-benzo[d]imidazol-2-yl)butyl)(isopropyl)amino)methyl)-5-(4-(cyclopropylamino)-7H-pyrrolo[2,3-d]pyrimidin-7-yl)cyclopentane-1,2-diol |
| B5 | 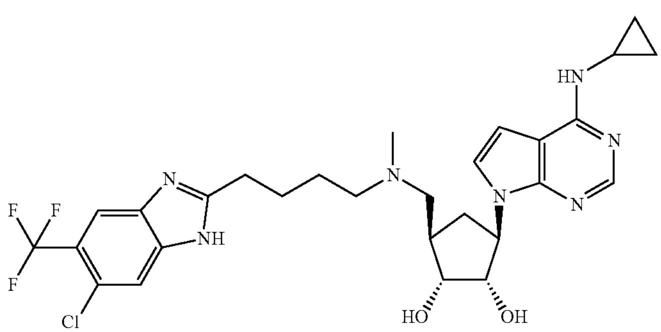 [SMILES: CN(CCCCc1nc2cc(C(F)(F)F)c(Cl)cc2[nH]1)C[C@H]1C[C@@H](n2ccc3c(NC4CC4)ncnc32)[C@H](O)[C@@H]1O] | (1S,2R,3R,5R)-3-(((4-(6-chloro-5-(trifluoromethyl)-1H-benzo[d]imidazol-2-yl)butyl)(methyl)amino)methyl)-5-(4-(cyclopropylamino)-7H-pyrrolo[2,3-d]pyrimidin-7-yl)cyclopentane-1,2-diol |

TABLE 2-continued

| Cmpd. No. | Structures | Chemical Name |
|---|---|---|
| B6 | 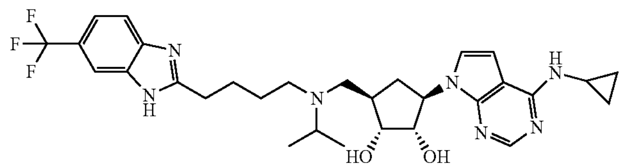 [SMILES: CC(C)N(CCCCc1nc2ccc(C(F)(F)F)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-((isopropyl(4-(6-(trifluoromethyl)-1H-benzo[d]imidazol-2-yl)butyl)amino)methyl)cyclopentane-1,2-diol |
| B7 | 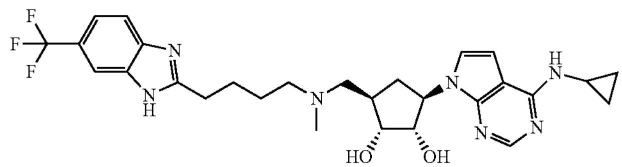 [SMILES: CN(CCCCc1nc2ccc(C(F)(F)F)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-((methyl(4-(6-(trifluoromethyl)-1H-benzo[d]imidazol-2-yl)butyl)amino)methyl)cyclopentane-1,2-diol |
| B8 | 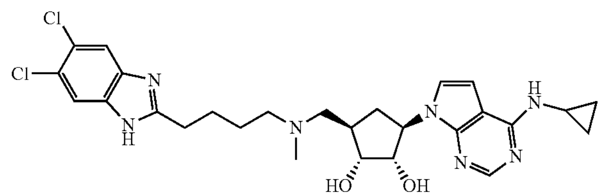 [SMILES: CN(CCCCc1nc2cc(Cl)c(Cl)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(methyl)amino)methyl)cyclopentane-1,2-diol |
| B9 | 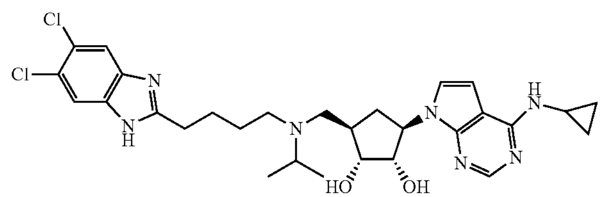 [SMILES: CC(C)N(CCCCc1nc2cc(Cl)c(Cl)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(isopropyl)amino)methyl)cyclopentane-1,2-diol trihydrochloride |
| B10 | 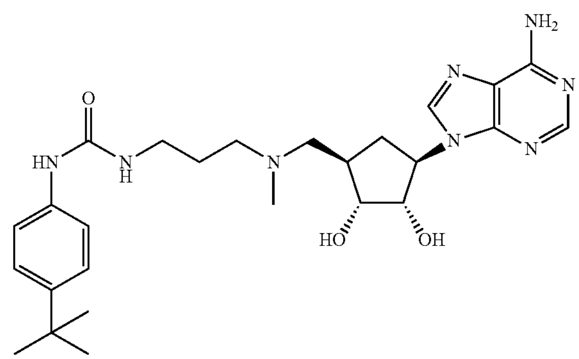 [SMILES: CN(CCCNC(=O)Nc1ccc(C(C)(C)C)cc1)C[C@H]1C[C@@H](n2cnc3c(N)ncnc32)[C@H](O)[C@@H]1O] | 1-(3-((((1R,2R,3S,4R)-4-(6-amino-9H-purin-9-yl)-2,3-dihydroxycyclopentyl)methyl)(methyl)amino)propyl)-3-(4-(tert-butyl)phenyl)urea |
| B11 | 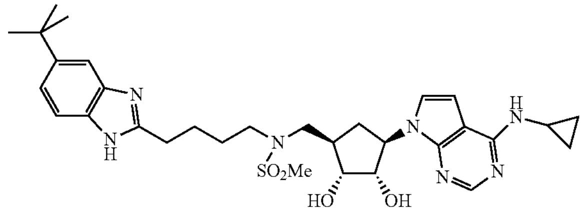 [SMILES: CC(C)(C)c1ccc2[nH]c(CCCCN(C[C@H]3C[C@@H](n4ccc5c(NC6CC6)ncnc54)[C@H](O)[C@@H]3O)S(C)(=O)=O)nc2c1] | N-(4-(5-(tert-butyl)-1H-benzo[d]imidazol-2-yl)butyl)-N-((((1R,2R,3S,4R)-4-(4-(cyclopropylamino)-7H-pyrrolo[2,3-d]pyrimidin-7-yl)-2,3-dihydroxycyclopentyl)methyl)methanesulfonamide |

TABLE 2-continued

| Cmpd. No. | Structures | Chemical Name |
|---|---|---|
| B12 | 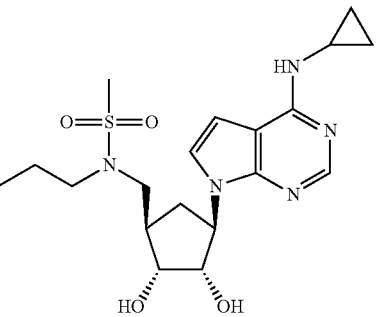 | N-(4-(6-chloro-5-(trifluoromethyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide |
| B13 | 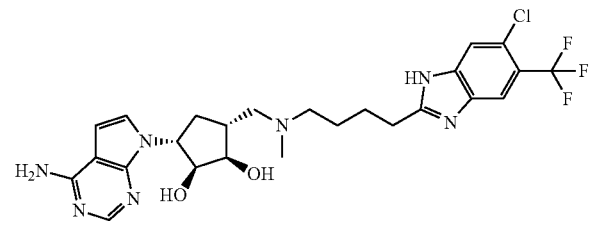 [SMILES: CN(CCCCc1nc2cc(C(F)(F)F)c(Cl)cc2[nH]1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-(((4-(6-chloro-5-(trifluoromethyl)-1H-benzo[d]imidazol-2-yl)butyl)(methyl)amino)methyl)cyclopentane-1,2-diol |
| B14 | 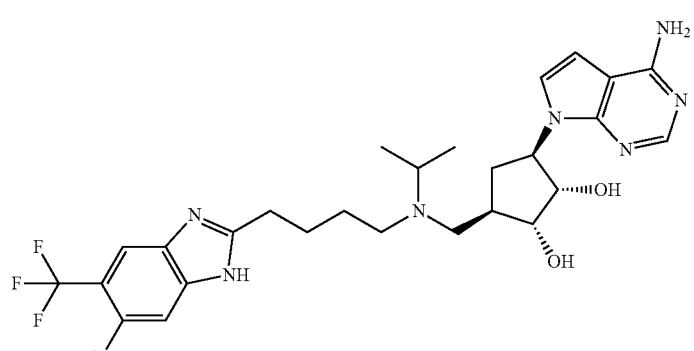 | (1R,2S,3R,5R)-3-(4-amino-7H-pyrrolo[2,3-d]pyrimidin-7-yl)-5-(((4-(6-chloro-5-(trifluoromethyl)-1H-benzo[d]imidazol-2-yl)butyl)(isopropyl)amino)methyl)cyclopentane-1,2-diol |
| B15 | 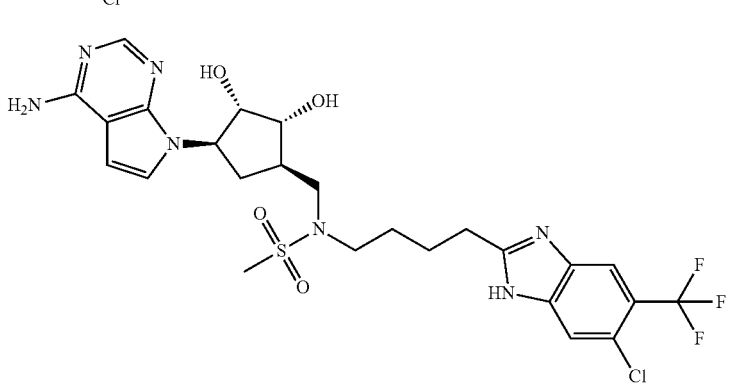 | N-(((1R,2R,3S,4R)-4-(4-amino-7H-pyrrolo[2,3-d]pyrimidin-7-yl)-2,3-dihydroxycyclopentyl)methyl)-N-(4-(6-chloro-5-(trifluoromethyl)-1H-benzo[d]imidazol-2-yl)butyl)methanesulfonamide |
| B16 | 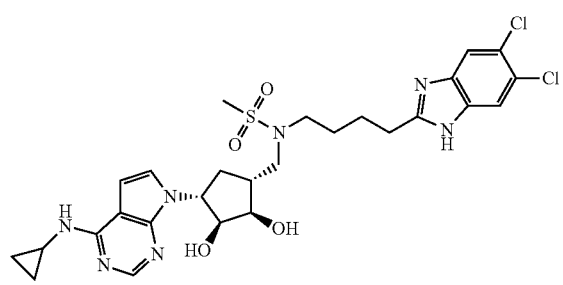 [SMILES: CS(=O)(=O)N(CCCCc1nc2cc(Cl)c(Cl)cc2[nH]1)C[C@H]1C[C@@H](n2ccc3c(NC4CC4)ncnc32)[C@H](O)[C@@H]1O] | N-(((1R,2R,3S,4R)-4-(4-(cyclopropylamino)-7H-pyrrolo[2,3-d]pyrimidin-7-yl)-2,3-dihydroxycyclopentyl)methyl)-N-(4-(5,6-dichloro-1H-benzo[d]imidazol-2-yl)butyl)methanesulfonamide |

TABLE 2-continued

| Cmpd. No. | Structures | Chemical Name |
|---|---|---|
| B17 | 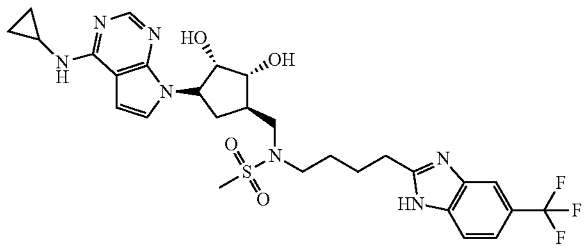 | N-(((1R,2R,3S,4R)-4-(4-(cyclopropylamino)-7H-pyrrolo[2,3-d]pyrimidin-7-yl)-2,3-dihydroxycyclopentyl)methyl)-N-(4-(5-(trifluoromethyl)-1H-benzo[d]imidazol-2-yl)butyl)methanesulfonamide |

TABLE 3

| | Structures |
|---|---|
| SAH | 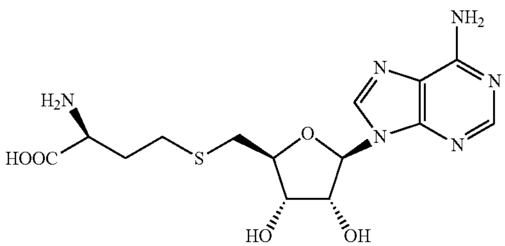 [SMILES: Nc1ncnc2c1ncn2[C@@H]1O[C@H](CSCC[C@H](N)C(=O)O)[C@@H](O)[C@H]1O] |
| C1 | 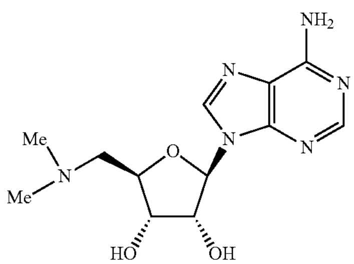 [SMILES: CN(C)C[C@H]1O[C@@H](n2cnc3c(N)ncnc32)[C@H](O)[C@@H]1O] |
| C2 | 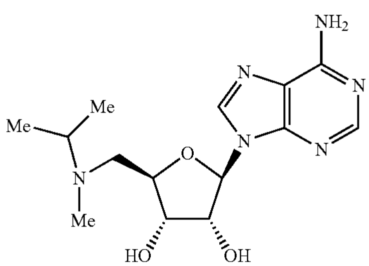 [SMILES: CC(C)N(C)C[C@H]1O[C@@H](n2cnc3c(N)ncnc32)[C@H](O)[C@@H]1O] |
| C64 | 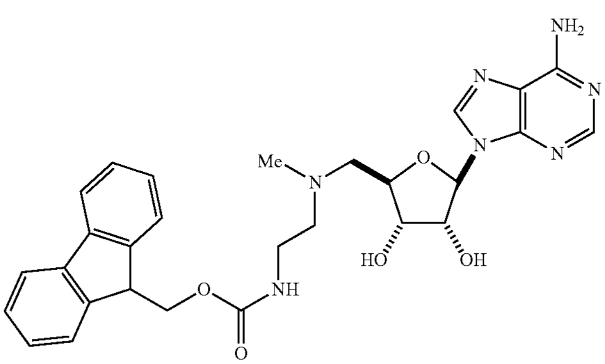 [SMILES: CN(CCNC(=O)OCC1c2ccccc2-c2ccccc21)C[C@H]1O[C@@H](n2cnc3c(N)ncnc32)[C@H](O)[C@@H]1O] |

TABLE 3-continued
C79
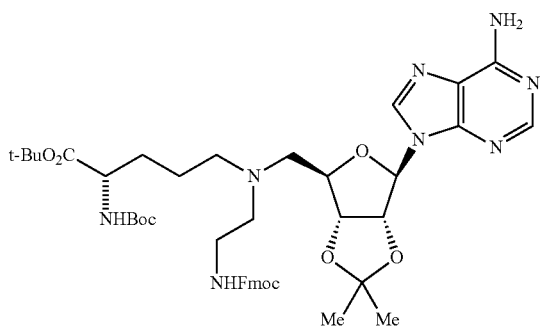
C80
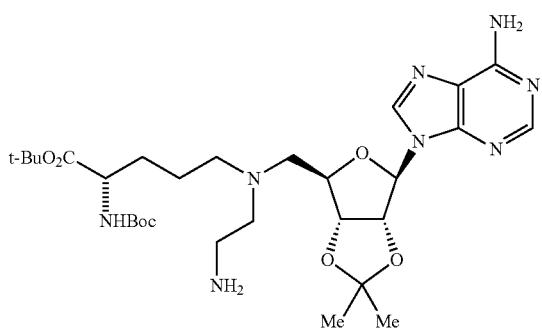
C81
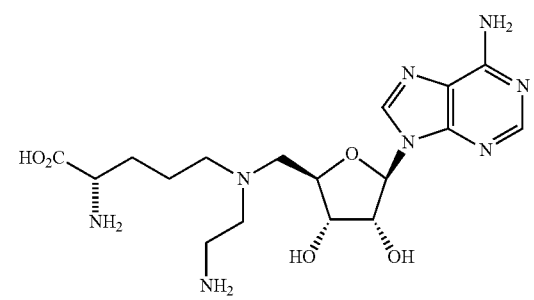 [SMILES: NCCN(CCC[C@H](N)C(=O)O)C[C@H]1O[C@@H](n2cnc3c(N)ncnc32)[C@H](O)[C@@H]1O]
C83
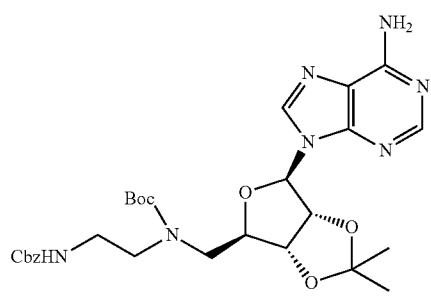 [SMILES: CC(C)(C)OC(=O)N(CCNC(=O)OCc1ccccc1)C[C@H]1O[C@@H](n2cnc3c(N)ncnc32)[C@@H]2OC(C)(C)O[C@@H]21]
C84
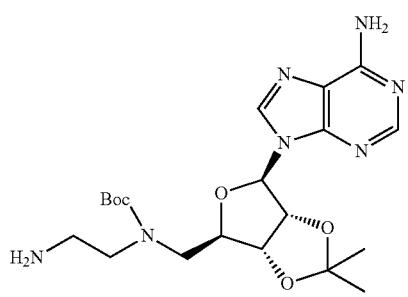 [SMILES: CC(C)(C)OC(=O)N(CCN)C[C@H]1O[C@@H](n2cnc3c(N)ncnc32)[C@@H]2OC(C)(C)O[C@@H]21]

TABLE 3-continued
C85
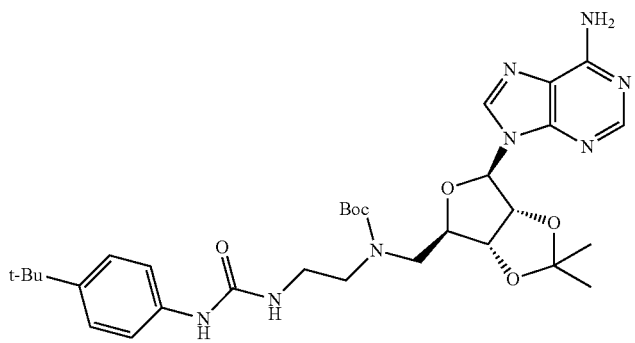 [SMILES: CC(C)(C)OC(=O)N(CCNC(=O)Nc1ccc(C(C)(C)C)cc1)C[C@H]1O[C@@H](n2cnc3c(N)ncnc32)[C@@H]2OC(C)(C)O[C@@H]21]
C86
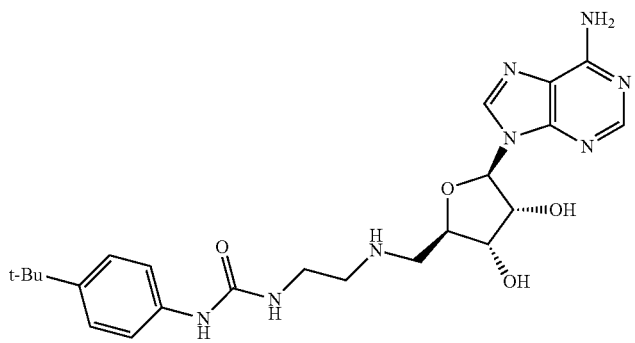 [SMILES: CC(C)(C)c1ccc(NC(=O)NCCNC[C@H]2O[C@@H](n3cnc4c(N)ncnc43)[C@H](O)[C@@H]2O)cc1]
C89
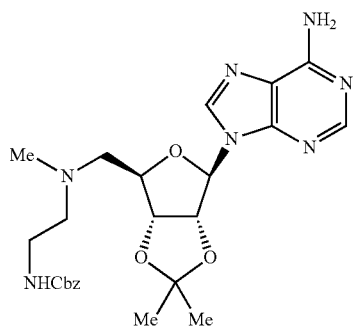 [SMILES: CN(CCNC(=O)OCc1ccccc1)C[C@H]1O[C@@H](n2cnc3c(N)ncnc32)[C@@H]2OC(C)(C)O[C@@H]21]
C90
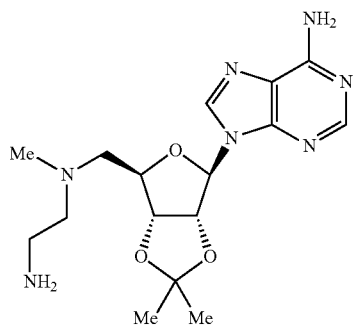 [SMILES: CN(CCN)C[C@H]1O[C@@H](n2cnc3c(N)ncnc32)[C@@H]2OC(C)(C)O[C@@H]21]

TABLE 3-continued
C91
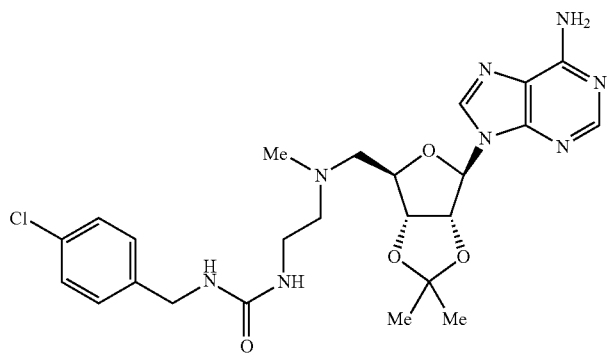 [SMILES: CN(CCNC(=O)NCc1ccc(Cl)cc1)C[C@H]1O[C@@H](n2cnc3c(N)ncnc32)[C@@H]2OC(C)(C)O[C@@H]21]
C92
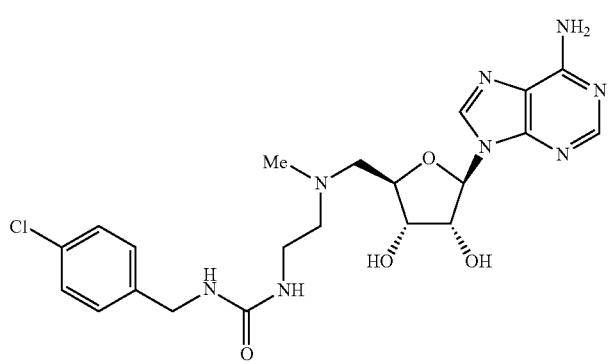 [SMILES: CN(CCNC(=O)NCc1ccc(Cl)cc1)C[C@H]1O[C@@H](n2cnc3c(N)ncnc32)[C@H](O)[C@@H]1O]
C93
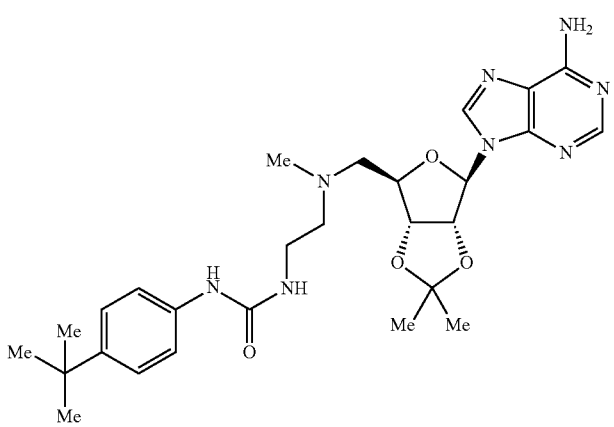 [SMILES: CN(CCNC(=O)Nc1ccc(C(C)(C)C)cc1)C[C@H]1O[C@@H](n2cnc3c(N)ncnc32)[C@@H]2OC(C)(C)O[C@@H]21]
C94
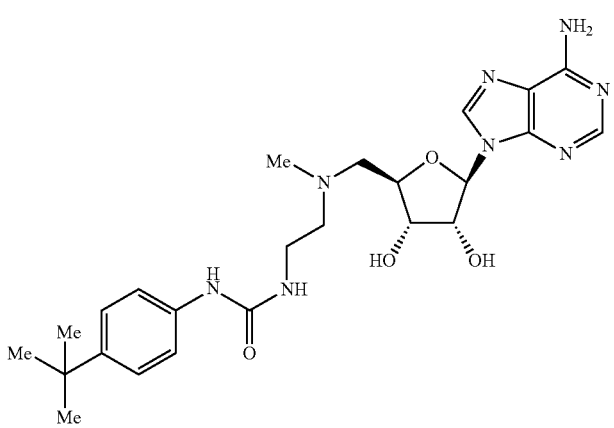 [SMILES: CN(CCNC(=O)Nc1ccc(C(C)(C)C)cc1)C[C@H]1O[C@@H](n2cnc3c(N)ncnc32)[C@H](O)[C@@H]1O]

TABLE 3-continued
C95
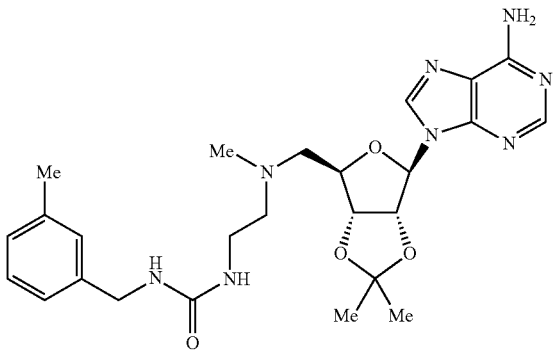 [SMILES: Cc1cccc(CNC(=O)NCCN(C)C[C@H]2O[C@@H](n3cnc4c(N)ncnc43)[C@@H]3OC(C)(C)O[C@@H]32)c1]
C96
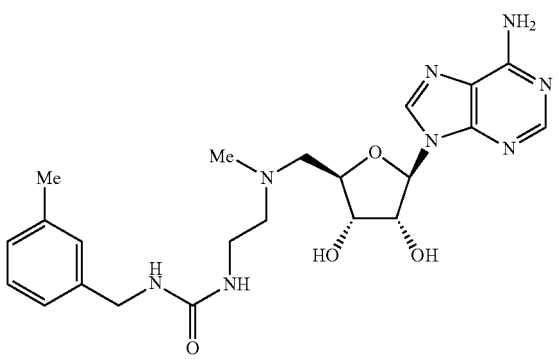 [SMILES: Cc1cccc(CNC(=O)NCCN(C)C[C@H]2O[C@@H](n3cnc4c(N)ncnc43)[C@H](O)[C@@H]2O)c1]
C97
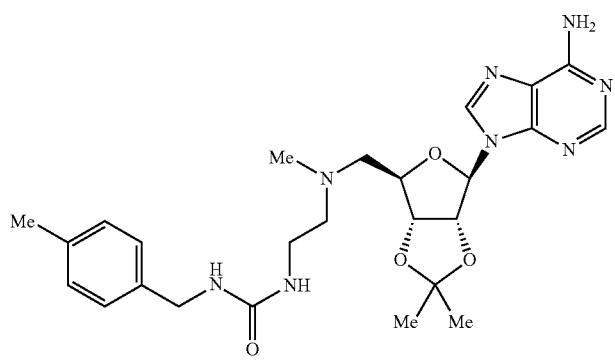 [SMILES: Cc1ccc(CNC(=O)NCCN(C)C[C@H]2O[C@@H](n3cnc4c(N)ncnc43)[C@@H]3OC(C)(C)O[C@@H]32)cc1]
C98
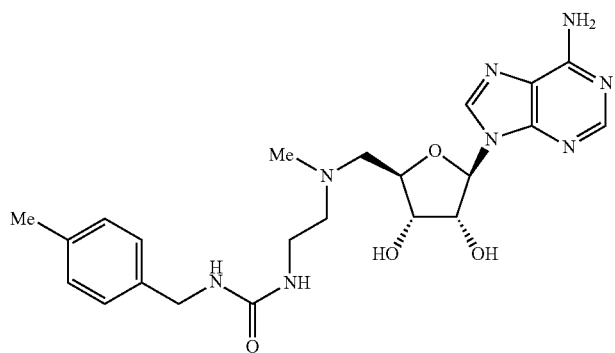 [SMILES: Cc1ccc(CNC(=O)NCCN(C)C[C@H]2O[C@@H](n3cnc4c(N)ncnc43)[C@H](O)[C@@H]2O)cc1]

TABLE 3-continued
C112
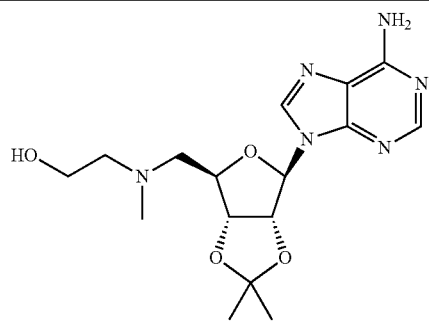
C113
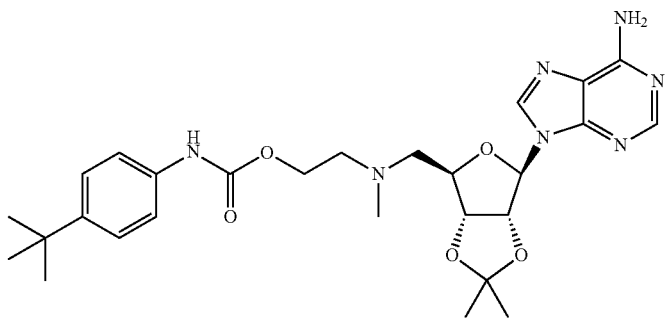 [SMILES: CN(CCOC(=O)Nc1ccc(C(C)(C)C)cc1)C[C@H]1O[C@@H](n2cnc3c(N)ncnc32)[C@@H]2OC(C)(C)O[C@@H]21]
C114
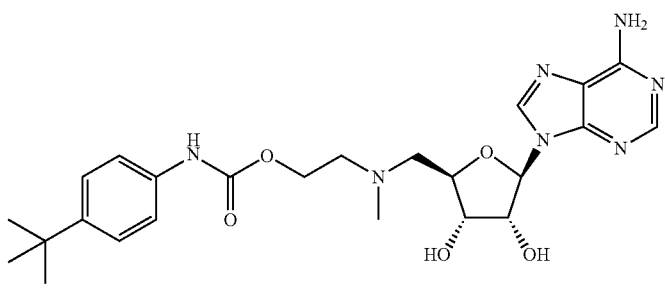 [SMILES: CN(CCOC(=O)Nc1ccc(C(C)(C)C)cc1)C[C@H]1O[C@@H](n2cnc3c(N)ncnc32)[C@H](O)[C@@H]1O]
C115
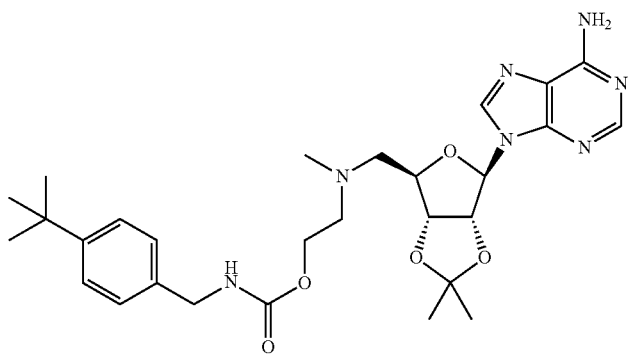 [SMILES: CN(CCOC(=O)NCc1ccc(C(C)(C)C)cc1)C[C@H]1O[C@@H](n2cnc3c(N)ncnc32)[C@@H]2OC(C)(C)O[C@@H]21]
C116
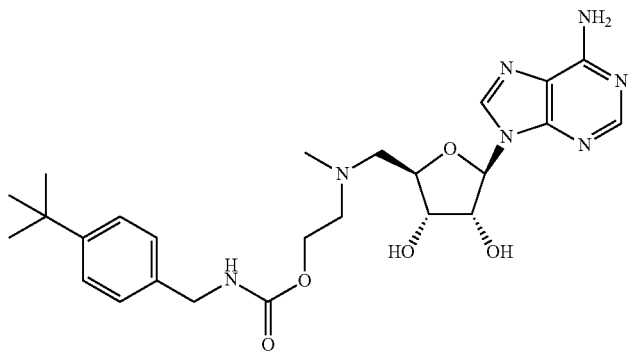 [SMILES: CN(CCOC(=O)NCc1ccc(C(C)(C)C)cc1)C[C@H]1O[C@@H](n2cnc3c(N)ncnc32)[C@H](O)[C@@H]1O]

TABLE 3-continued
C117
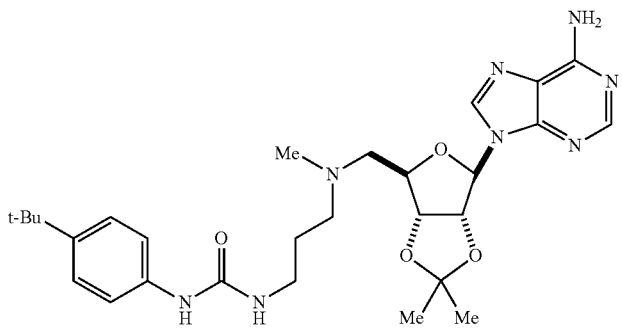
C118
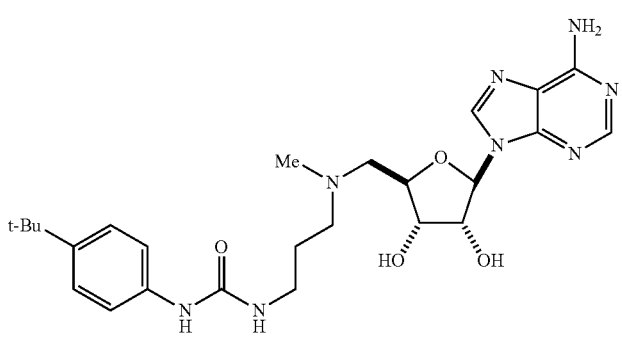
C122
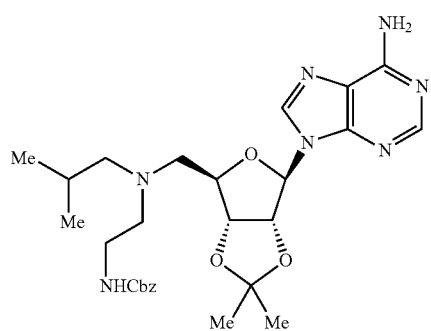 [SMILES: CC(C)CN(CCNC(=O)OCc1ccccc1)C[C@H]1O[C@@H](n2cnc3c(N)ncnc32)[C@@H]2OC(C)(C)O[C@@H]21]
C123
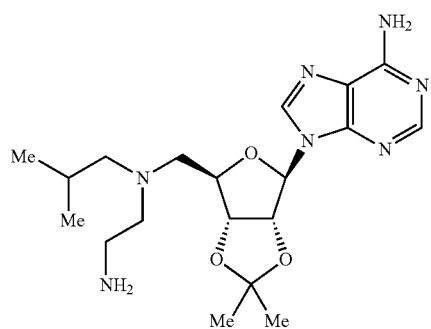 [SMILES: CC(C)CN(CCN)C[C@H]1O[C@@H](n2cnc3c(N)ncnc32)[C@@H]2OC(C)(C)O[C@@H]21]

TABLE 3-continued
C124
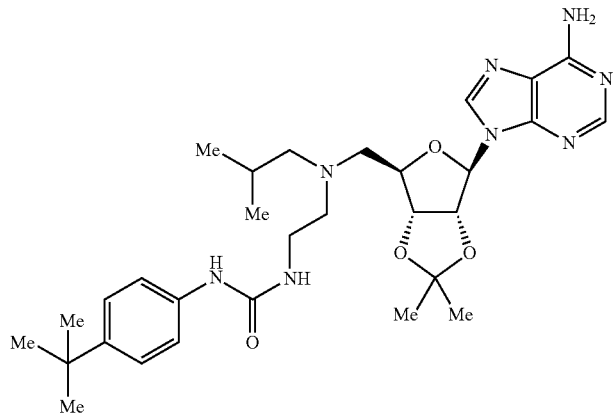 [SMILES: CC(C)CN(CCNC(=O)Nc1ccc(C(C)(C)C)cc1)C[C@H]1O[C@@H](n2cnc3c(N)ncnc32)[C@@H]2OC(C)(C)O[C@@H]21]
C125
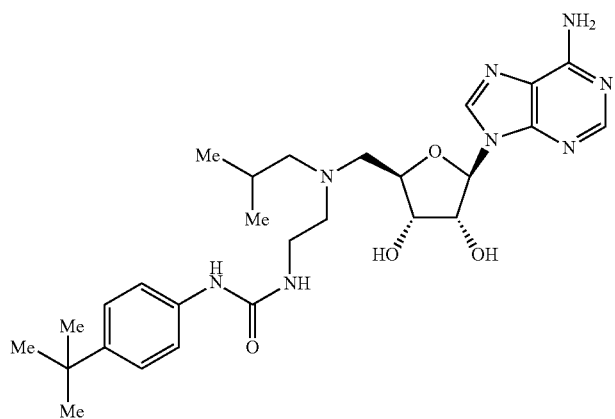 [SMILES: CC(C)CN(CCNC(=O)Nc1ccc(C(C)(C)C)cc1)C[C@H]1O[C@@H](n2cnc3c(N)ncnc32)[C@H](O)[C@@H]1O]
C126
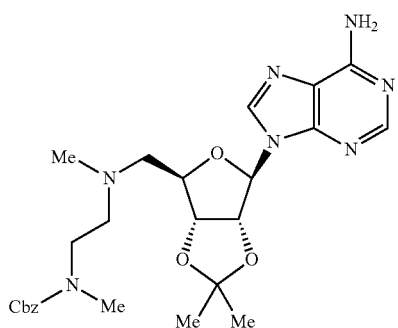 [SMILES: CN(CCN(C)C(=O)OCc1ccccc1)C[C@H]1O[C@@H](n2cnc3c(N)ncnc32)[C@@H]2OC(C)(C)O[C@@H]21]
C127
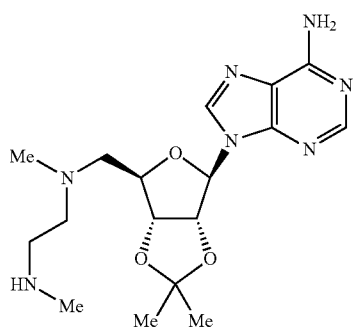 [SMILES: CNCCN(C)C[C@H]1O[C@@H](n2cnc3c(N)ncnc32)[C@@H]2OC(C)(C)O[C@@H]21]

TABLE 3-continued
C128
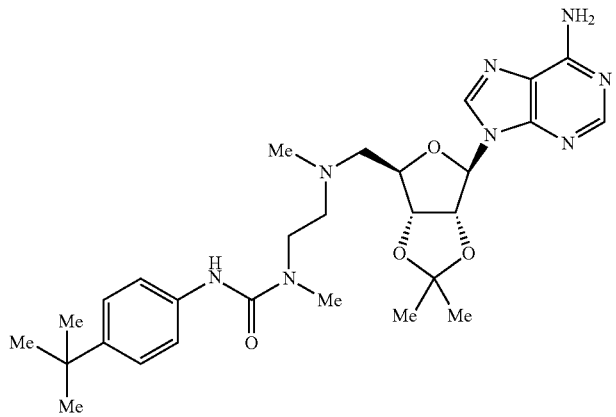 [SMILES: CN(CCN(C)C(=O)Nc1ccc(C(C)(C)C)cc1)C[C@H]1O[C@@H](n2cnc3c(N)ncnc32)[C@@H]2OC(C)(C)O[C@@H]21]
C129
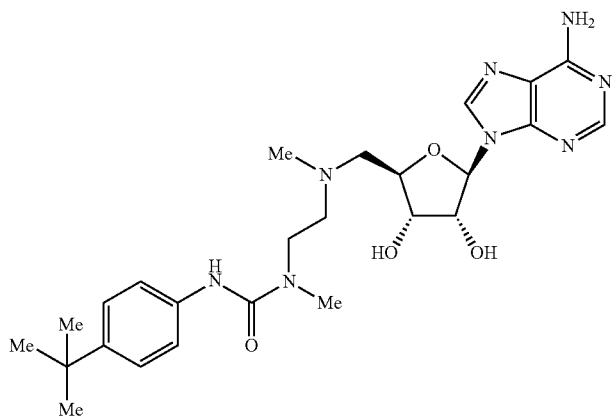 [SMILES: CN(CCN(C)C(=O)Nc1ccc(C(C)(C)C)cc1)C[C@H]1O[C@@H](n2cnc3c(N)ncnc32)[C@H](O)[C@@H]1O]
C130
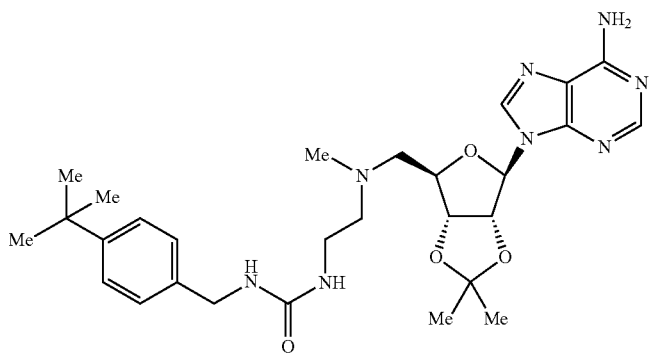 [SMILES: CN(CCNC(=O)NCc1ccc(C(C)(C)C)cc1)C[C@H]1O[C@@H](n2cnc3c(N)ncnc32)[C@@H]2OC(C)(C)O[C@@H]21]
C131
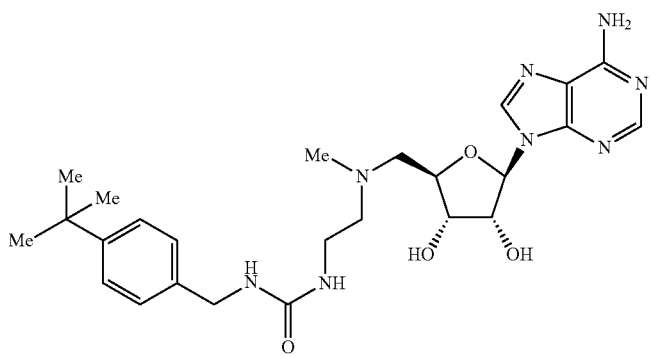 [SMILES: CN(CCNC(=O)NCc1ccc(C(C)(C)C)cc1)C[C@H]1O[C@@H](n2cnc3c(N)ncnc32)[C@H](O)[C@@H]1O]

TABLE 3-continued
C140
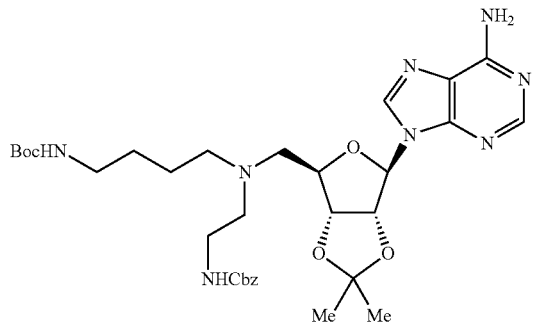 [SMILES: CC(C)(C)OC(=O)NCCCCN(CCNC(=O)OCc1ccccc1)C[C@H]1O[C@@H](n2cnc3c(N)ncnc32)[C@@H]2OC(C)(C)O[C@@H]21]
C141
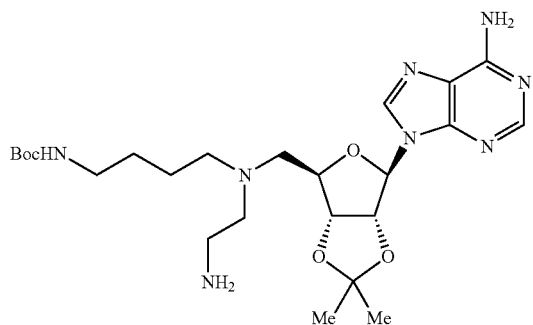 [SMILES: CC(C)(C)OC(=O)NCCCCN(CCN)C[C@H]1O[C@@H](n2cnc3c(N)ncnc32)[C@@H]2OC(C)(C)O[C@@H]21]
C142
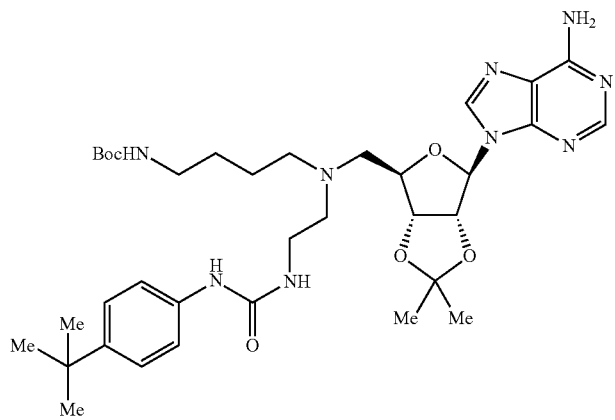 [SMILES: CC(C)(C)OC(=O)NCCCCN(CCNC(=O)Nc1ccc(C(C)(C)C)cc1)C[C@H]1O[C@@H](n2cnc3c(N)ncnc32)[C@@H]2OC(C)(C)O[C@@H]21]
C143
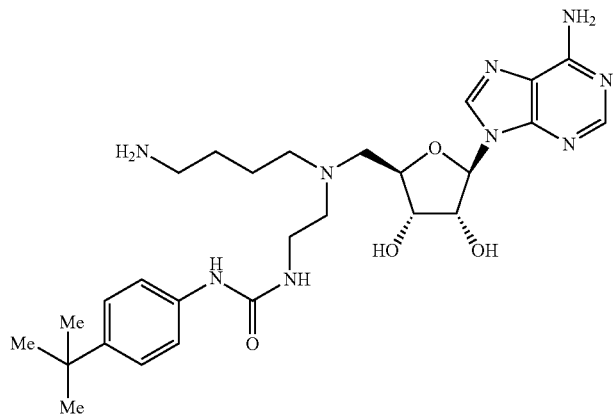 [SMILES: CC(C)(C)c1ccc(NC(=O)NCCN(CCCCN)C[C@H]2O[C@@H](n3cnc4c(N)ncnc43)[C@H](O)[C@@H]2O)cc1]

TABLE 4
D1 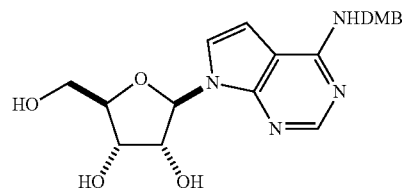
D2 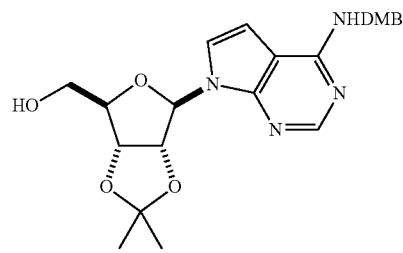
D3 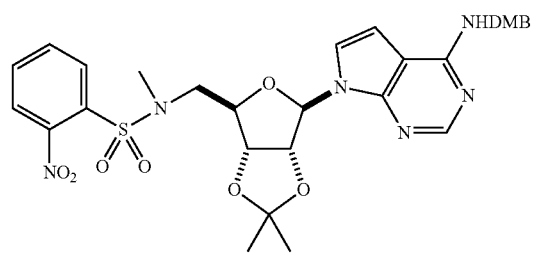
D4 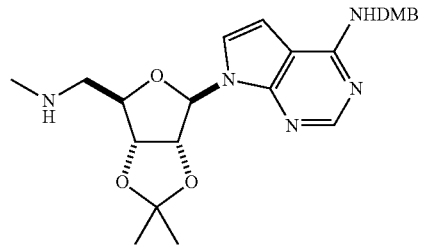
D5 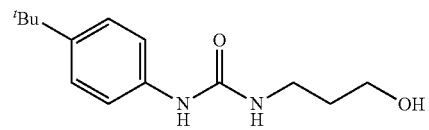 [SMILES: CC(C)(C)c1ccc(NC(=O)NCCCO)cc1]
D6 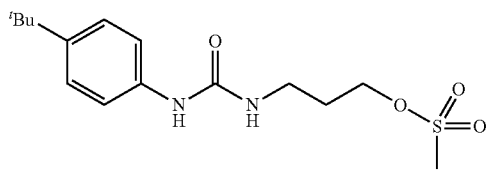 [SMILES: CC(C)(C)c1ccc(NC(=O)NCCCOS(C)(=O)=O)cc1]
D7 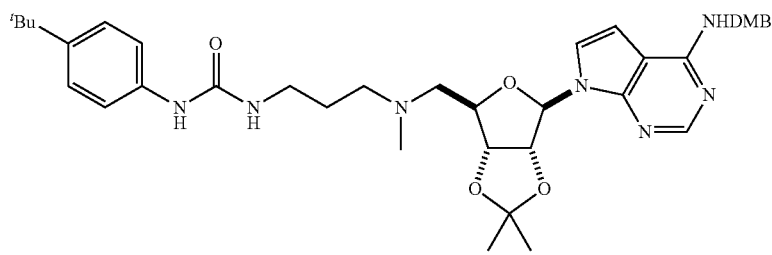

TABLE 4-continued
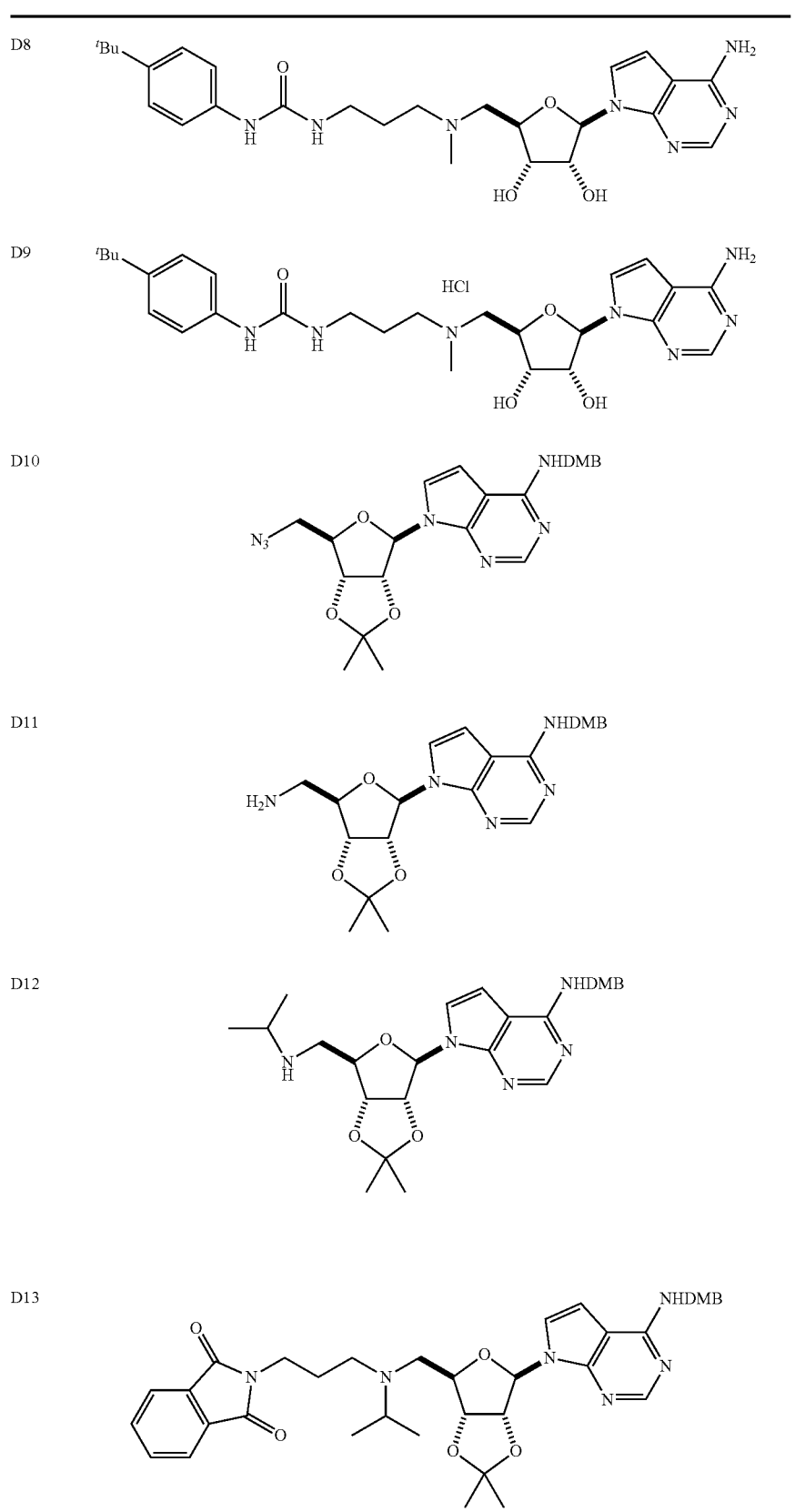

TABLE 4-continued

D14 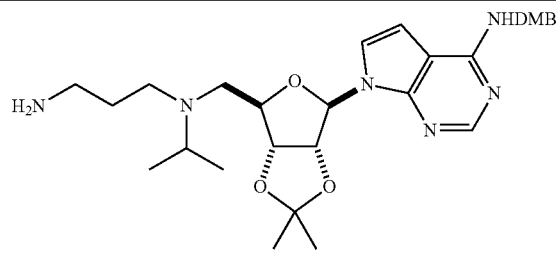

D15 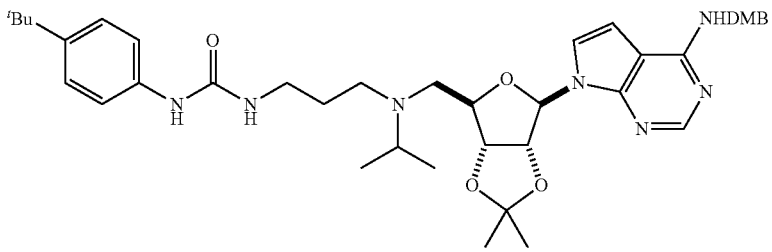

D16 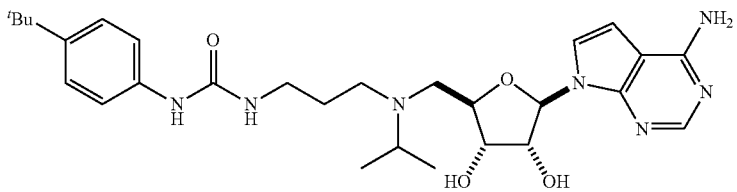

D17 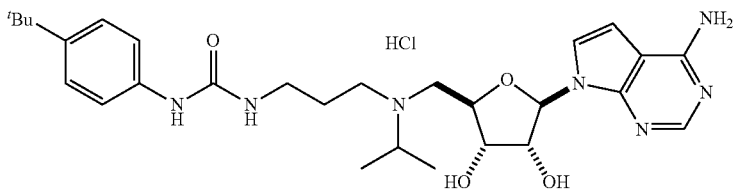

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5- or 6-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spirorings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_3$) occurs more than one time in any constituent or formula for a compound, its definition at each occurrence is independent of its definition at every other occurrence. Thus, for example, if a group is shown to be substituted with 0-2 $R_3$ moieties, then the group may optionally be substituted with up to two $R_3$ moieties and $R_3$ at each occurrence is selected independently from the definition of $R_3$. Also, combinations of substituents and/or variables are permissible, but only if such combinations result in stable compounds.

The term "hydroxy" or "hydroxyl" includes groups with an —OH or —O$^-$.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention (i.e., DOT1L inhibitors) that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

For example, compounds of Formula (I) include those of the following chiral isomers and geometric isomers.

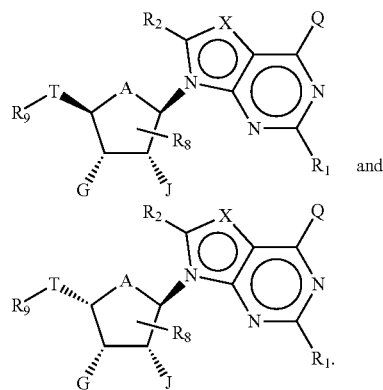

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

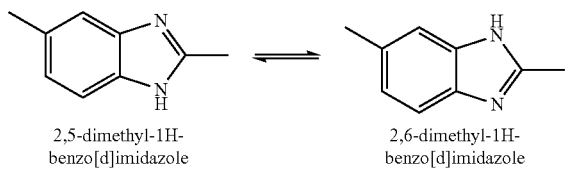

2,5-dimethyl-1H-benzo[d]imidazole 2,6-dimethyl-1H-benzo[d]imidazole

Another example of tautomerism is shown below.

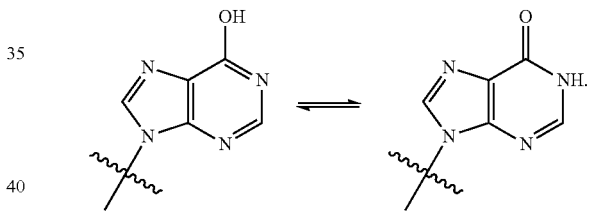

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of any of the Formulae disclosed herein include the compounds themselves, as well as their N-oxides, salts, their solvates, and their prodrugs, if applicable. A salt, for example, can be formed between an anion and a positively charged group (e.g., amino) on the compound or inhibitor (e.g., a substituted nucleoside compound such as a substituted purine or 7-deazapurine compound). Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on the compound or inhibitor (e.g., a substituted nucleoside compound such as a substituted purine or 7-deazapurine compound). Suitable cations include sodium ion, potassium ion, magnesium ion, calcium ion, and an ammonium cation such as tetramethylammonium ion. The compound or inhibitor (e.g., a substituted nucleoside compound such as a substituted purine or 7-deazapurine compound) also include those salts containing quaternary nitrogen atoms. Examples of prodrugs include esters and other pharmaceutically acceptable derivatives, which, upon administration to a subject, are capable of providing active substituted nucleoside compound such as a substituted purine or 7-deazapurine.

Additionally, the compounds of the present invention, for example, the salts of the compounds, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention also provides methods for the synthesis of the compounds of any of the Formulae disclosed herein. The present invention also provides detailed methods for the synthesis of various disclosed compounds of the present invention according to the schemes and the Examples described in WO2012/075381, WO2012/075492, WO2012/082436, WO2012/75500, and U.S. Provisional Application No. 61/682,090, the contents of which are hereby incorporated by reference in their entireties.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For the hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
Ac acetyl
ACN acetonitrile
AcOH acetic acid
atm atmosphere
Bn benzyl
BOC tert-butoxy carbonyl
BOP (benzotriazol-1-yloxy)tris(dimethylamino)phosphonium hexafluorophosphate
Cbz benzyloxycarbonyl
COMU (1-cyano-2-ethoxy-2-oxoethylidenaminooxy)dimethylamino-morpholino-carbenium hexafluorophosphate
d days
DBU 1,8-diazabicyclo[5.4.0]undec-7-ene
DCE 1,2 dichloroethane
DCM dichloromethane
DEA diethylamine
DEAD diethyl azodicarboxylate
DIAD diisopropyl azodicarboxylate
DiBAL-H diisobutylalumininium hydride
DIPEA N,N-diisopropylethylamine (Hunig's base)
DMAP N,N-dimethyl-4-aminopyridine
DMB 2,4 dimethoxybenzyl
DMF dimethylformamide
DMSO dimethylsulfoxide
DPPA diphenylphosphoryl azide
EA or EtOAc ethylacetate
EDC or EDCI N-(3-dimethylaminopropyl)-N'-ethylcarbodiimide
ELS Evaporative Light Scattering
ESI– Electrospray negative mode
ESI+ Electrospray positive mode
$Et_2O$ diethyl ether
$Et_3N$ or TEA triethylamine
EtOH ethanol
FA formic acid
FC flash chromatography
h hours
$H_2O$ water
HATU O-(7-azabenzotriazol-1-yl)-N,N,N',N'-tetramethyluronium hexafluorophosphate
HCl hydrochloric acid
HOAT 1-hydroxy-7-azabenzotriazole
HOBt 1-hydroxybenzotriazole
HOSu N-hydroxysuccinimide
HPLC high performance liquid chromatography
Inj. Vol. injection volume
I.V. or IV intravenous
KHMDs potassium hexamethyldisilazide
LC/MS or LC-MS liquid chromatography mass spectrum
LDA lithium diisopropylamide
LG leaving group
LiHMs lithium hexamethyldisilazide
M Molar
m/z mass/charge ratio
m-CPBA meta-chloroperbenzoic acid
MeCN acetonitrile
MeOD $d_4$-methanol
MeOH methanol
$MgSO_4$ magnesium sulfate
min minutes
MS mass spectrometry or mass spectrum
Ms mesyl
MsCl methanesulfonyl chloride
MsO mesylate
MWI microwave irradiation
$Na_2CO_3$ sodium carbonate
$NaHCO_3$ sodium bicarbonate
NaHMDs sodium hexamethyldisilazide
NaOH sodium hydroxide
NIS N-iodosuccinimide
NMR Nuclear Magnetic Resonance
o/n or O/N overnight
PE petroleum ether
PG protecting group
PKMT protein lysine methyltransferase
PMB para-methoxybenzyl
PMT protein methyltransferase
PPAA 1-propanephosphonic acid cyclic anhydride
ppm parts per million
prep HPLC preparative high performance liquid chromatography
prep TLC preparative thin layer chromatography
p-TsOH para-toluenesulfonic acid
rt or RT room temperature
SAH S-adenosylhomocysteine
SAM S-adenosylmethionine
SAR structure activity relationship
SEM 2-(trimethylsilyl)ethoxymethyl
SEMCl (trimethylsilyl)ethoxymethyl chloride
SFC supercritical chromatography
SGC silica gel chromatography
SPR surface plasmon resonance
STAB sodium triacetoxyborohydride
TBAF tetra-n-butylammonium fluoride
TFA trifluoroacetic acid
TfO triflate
THF tetrahydrofuran
THP tetrahydropyran
TLC thin layer chromatography
Ts tosyl
TsOH tosic acid
UV ultraviolet Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

Compounds suitable for the methods of the invention, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described herein.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

A composition of the present invention comprises a compound of Formula (I), or a pharmaceutically acceptable salt thereof, and one or more therapeutic agents. The present invention provides for the administration of a compound of Formula (I) or a pharmaceutically acceptable salt thereof, and one or more therapeutic agents as a co-formulation or separate formulations, wherein the administration of formulations is simultaneous, sequential, or in alternation. In one embodiment, the one or more therapeutic agents can be an agent that is recognized in the art as being useful to treat the disease or condition being treated by the composition of the present invention. In another embodiment, the one or more therapeutic agents can be an agent that is not recognized in the art as being useful to treat the disease or condition being treated by the composition of the present invention. In one aspect, the other therapeutic agents can be an agent that imparts a beneficial attribute to the composition of the present invention (e.g., an agent that affects the viscosity of the composition). The beneficial attribute to the composition of the present invention includes, but is not limited to, pharmacokinetic or pharmacodynamic co-action resulting from the combination of a compound of Formula (I) and one or more therapeutic agents. For example, the one or more therapeutic agents can be anticancer agents or chemotherapeutic agents. For example, the one or more therapeutic agents can be selected from Ara-C, Daunorubicin, Decitabine, Vidaza, Mitoxantrone, JQ1, IBET151, Panobinostat, Vorinostat, Quizartinib, Midostaurin, Tranylcypromine, LSD1 inhibitor II, Navitoclax, or functional analogs, derivatives, produgs, and metabolites thereof. Preferably, the therapeutic agent is Ara-C or Daunorubicin or functional analogs, derivatives, produgs, and metabolites thereof.

In some embodiments, the therapeutic agents are topoisomerase inhibitors (e.g., Mitoxantrone), hypomethylating agents (e.g., Decitabine or Vidaza), Menin inhibitors (e.g., MI-2), Bromodomain inhibitors (e.g., IBET-151), HDAC inhibitors (e.g., Panobinostat), Bcl-2 inhibitors (e.g., Navitoclax) or FLT inhibitors (e.g., Quizartinib).

In some embodiments, the therapeutic agents are Bromodomain inhibitors (e.g., IBET-151) or Menin inhibitors (e.g., MI-2).

The therapeutic agents set forth below are for illustrative purposes and not intended to be limiting. The present invention includes at least one therapeutic agent selected from the lists below. The present invention can include more than one therapeutic agent, e.g., two, three, four, or five therapeutic agents such that the composition of the present invention can perform its intended function.

In one embodiment, the other therapeutic agent is an anticancer agent. In one embodiment, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In another embodiment, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine-131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; Pkc412; bryostatin; KAI-9803; SF1126; or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate), or lovastatin.

In another aspect, the other therapeutic agent is a chemotherapeutic agent or a cytokine such as G-CSF (granulocyte colony stimulating factor).

In yet another aspect, the other therapeutic agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In another aspect, the other therapeutic agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/ Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

In one embodiment, a composition of the present invention includes a compound of Formula (I) or a pharmaceutically acceptable salt thereof, and one or more anticancer agents. Anticancer agents include, for example, Ara-C, Daunorubicin, Decitabine, Vidaza, Mitoxantrone, JQ1, IBET151, Panobinostat, Vorinostat, Quizartinib, Midostaurin, Tranylcypromine, LSD1 inhibitor II, Navitoclax, or functional analogs, derivatives, produgs, and metabolites thereof.

The present invention provides methods for combination therapy in which a composition comprising a compound of Formula (I) or a pharmaceutically acceptable salt thereof, and one or more other therapeutic agents are administered to a subject in need for treatment of a disease or cancer. The combination therapy can also be administered to cancer cells to inhibit proliferation or induce cell death.

The present invention includes the combination therapy of administering a compound of Formula (I) or a pharmaceutically acceptable salt thereof, and anticancer agents, where the anticancer agents are Ara-C, Daunorubicin, Decitabine, Vidaza, Mitoxantrone, JQ1, IBET151, Panobinostat, Vorinostat, Quizartinib, Midostaurin, Tranylcypromine, LSD1 inhibitor II, Navitoclax.

In one aspect, a compound of Formula (I) or a pharmaceutically acceptable salt thereof and one or more therapeutic agents are administered simultaneously or sequentially.

In one aspect, a compound of Formula (I) or a pharmaceutically acceptable salt thereof is administered prior to administration of the composition of the invention comprising a compound of Formula (I) or a pharmaceutically acceptable salt thereof, and one or more therapeutic agents.

In one aspect, a compound of Formula (I) or a pharmaceutically acceptable salt thereof is administered prior to administration of one or more therapeutic agents, such that the one or more therapeutic agents are administered either in a single composition or in two or more compositions, e.g. administered simultaneously, sequentially, or in alternation.

"Combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. Therapeutic agents may also be administered in alternation.

The combination therapies featured in the present invention can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition of the present invention may be administered in combination with radiation therapy. Radiation therapy can also be administered in combination with a composition of the present invention and another chemotherapeutic agent described herein as part of a multiple agent therapy.

The present invention also provides pharmaceutical compositions comprising a compound of Formula (I) or pharmaceutically acceptable salts thereof, and one or more other therapeutic agent disclosed herein, mixed with pharmaceutically suitable carriers or excipient(s) at doses to treat or prevent a disease or condition as described herein.

In one aspect, the present invention also provides pharmaceutical compositions comprising any compound of Tables 1-4 or pharmaceutically acceptable salts thereof, and one or more therapeutic agents, mixed with pharmaceutically suitable carriers or excipient(s) at doses to treat or prevent a disease or condition as described herein.

In another aspect, the present invention also provides pharmaceutical compositions comprising Compound A2 having the formula:

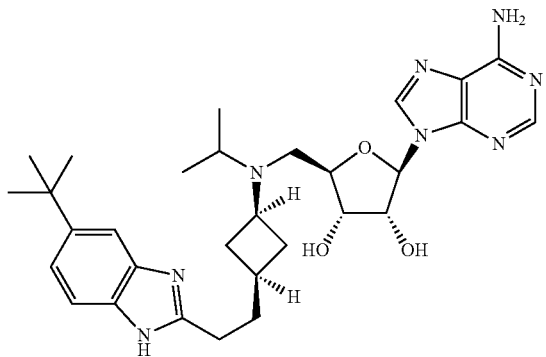 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

or pharmaceutically acceptable salts thereof, and one or more therapeutic agents, mixed with pharmaceutically suitable carriers or excipient(s) at doses to treat or prevent a disease or condition as described herein.

In another aspect, the present invention also provides pharmaceutical compositions comprising Compound D16 having the formula

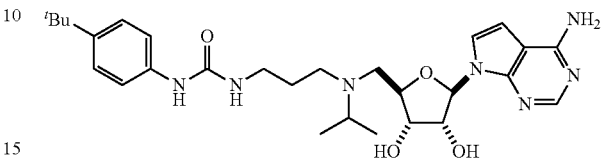

or pharmaceutically acceptable salts thereof, and one or more therapeutic agents, mixed with pharmaceutically suitable carriers or excipient(s) at doses to treat or prevent a disease or condition as described herein.

The pharmaceutical compositions of the present invention can also be administered in combination with other therapeutic agents or therapeutic modalities simultaneously, sequentially, or in alternation.

Mixtures of compositions of the present invention can also be administered to the patient as a simple mixture or in suitable formulated pharmaceutical compositions.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, N.Y.-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below. $IC_{50}$ values for DOT1L inhibition for select DOT1L inhibitors were determined as described in Example 1 and are listed below.

| Compound | DOT1L $IC_{50}$ (μM) |
| --- | --- |
| A2 | 0.00074 |
| A3 | 0.00073 |
| A5 | 0.00059 |
| A69 | 0.00251 |
| A75 | 0.00059 |
| A86 | 0.00062 |
| A87 | 0.0008 |
| A91 | 0.00218 |
| A93 | 0.00292 |

Diseases such as cancers and neurological disease can be treated by administration of modulators of protein (e.g., histone) methylation, e.g., modulators of histone methyltransferase, or histone demethylase enzyme activity. Histone methylation has been reported to be involved in aberrant expression of certain genes in cancers, and in silencing of neuronal genes in non-neuronal cells. The composition of this invention, e.g. a composition comprising any compound of Formula (I) or pharmaceutically acceptable salt thereof and one or more therapeutic agents described herein can be used to treat such diseases, i.e., to decrease or inhibit methylation of histones in affected cells or restore methylation to roughly its level in counterpart normal cells.

The present invention provides compositions and methods for treating or alleviating a symptom of conditions and diseases the course of which can be influenced by modulating the methylation status of histones or other proteins, wherein said methylation status is mediated at least in part by the activity of DOT1L. Modulation of the methylation status of histones can in turn influence the level of expression of target genes activated by methylation, and/or target genes suppressed by methylation. The method includes administering to a subject in need of such treatment, a therapeutically effective amount of a composition of the present invention or a pharmaceutically acceptable salt, prodrug, metabolite, polymorph or solvate thereof, to a subject in need of such treatment.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

The disorder in which DOT1L-mediated protein methylation plays a part can be cancer, a cell proliferative disorder, or a precancerous condition. Exemplary cancers that may be treated include brain and CNS cancer, kidney cancer, ovarian cancer, pancreatic cancer, lung cancer, breast cancer, colon cancer, prostate cancer, or a hematological cancer. For example, the hematological cancer is leukemia or lymphoma. Preferably the cancer is leukemia. The leukemia can be acute or chronic leukemia. In some embodiments, the leukemia is acute myeloid leukemia or acute lymphocytic leukemia. In some embodiments, leukemia that may be treated is leukemia characterized by a chromosomal rearrangement on chromosome 11q23, including chimeric fusion of mixed lineage leukemia gene (MLL) or partial tandem duplication of MLL (MLL-PTD). In some embodiments, leukemia that may be treated is leukemia characterized by the presence of a genetic lesion of MLL. Such genetic lesions include chromosomal rearrangements, such as translocations, deletions, and/or duplications of the MLL gene. MLL has been categorized or characterized as having a chimeric fusion of MLL, partial tandem duplication of the MLL gene (MLL-PTD), or nonrearranged MLL.

The disorder that can be treated by the combination therapy described herein can be a disorder medicated by translocation, deletion and/or duplication of a gene on chromosome 11 q23.

In general, compounds that are methylation modulators can be used for modulating cell proliferation. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a disorder in which DOT1L-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject of the present invention includes any human subject who has been diagnosed with, has symptoms of, or is at risk of developing a cancer or a precancerous condition.

A subject in need thereof may be a subject having a disorder associated DOT1L. A subject in need thereof can have a precancerous condition. Preferably, a subject in need thereof has cancer. A subject in need thereof can have cancer associated with DOT1L. In a preferred aspect, a subject in need thereof has one or more cancers selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, prostate cancer and a hematological cancer. Preferably, a subject in need thereof has a hematologic cancer, wherein the hematologic cancer is leukemia or lymphoma. Exemplary leukemia is MLL. Other hematologic cancers of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A subject in need thereof can be one who has been previously diagnosed or identified as having cancer or a precancerous condition. A subject in need thereof can also be one who is having (suffering from) cancer or a precancerous condition. Alternatively, a subject in need thereof can be one who is having an increased risk of developing such disorder relative to the population at large (i.e., a subject who is predisposed to developing such disorder relative to the population at large).

A subject in need thereof can have cancer associated with increased expression (mRNA or protein) and/or activity level of at least one protein selected from the group consisting of HOXA9, FLT3, MEIS1 and DOT1L. A subject in need thereof may have increased mRNA, protein, and/or activity level of at least of at least one signaling component downstream of at least one protein selected from the group consisting of HOXA9, FLT3, MEIS1 and DOT1L. Such downstream components are readily known in the art, and can include other transcription factors, or signaling proteins. As used herein, the term "increase in activity" refers to increased or a gain of function of a gene product/protein compared to the wild type. Accordingly, an increase in mRNA or protein expression and/or activity levels can be detected using any suitable method available in the art.

Optionally a subject in need thereof has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

In some embodiments, a subject in need thereof may have a secondary cancer as a result of a previous therapy. "Secondary cancer" means cancer that arises due to or as a result from previous carcinogenic therapies, such as chemotherapy. In some embodiments, the secondary cancer is a hematologic cancer, such as leukemia.

The subject may exhibit resistance to DOT1L histone methyltransferase inhibitors or any other therapeutic agent.

The invention also features a method of selecting a combination therapy for a subject having leukemia. The method includes the steps of: detecting the level of HOXA9, FLT3, MEIS1, and/or DOT1L in a sample from the subject; and selecting, based on the presence of the increased level of HOXA9, FLT3, MEIS1, and/or DOT1L a combination therapy for treating leukemia. In one embodiment, the therapy includes administering to the subject a composition of the invention. In one embodiment, the method further includes administrating to the subject a therapeutically effective amount of a composition of the invention. In one embodiment, the leukemia is characterized by partial tandem duplication of the MLL gene. In another embodiment, the leukemia is characterized by overexpression of HOXA9, FLT3, MEIS1 and/or DOT1L.

The methods and uses described herein may include steps of detecting the mRNA, protein and/or activity (function) level of HOXA9, FLT3, MEIS1, and/or DOT1L in a sample from a subject in need thereof prior to and/or after the administration of a composition of the invention (e.g., a composition comprising a compound of Formula (I) or pharmaceutically acceptable salts thereof, and one or more therapeutic agents) to the subject. The presence of the increased level of HOXA9, FLT3, MEIS1, and/or DOT1L in the tested sample indicates the subject is responsive to the combination therapy described herein.

The present invention provides personalized medicine, treatment and/or cancer management for a subject by genetic screening of increased gene expression (mRNA or protein), and/or increased function or activity level of at least one protein selected from the group consisting of HOXA9, FLT3, MEIS1 and DOT1L in the subject. For example, the present invention provides methods for treating or alleviating a symptom of cancer or a precancerous condition in a subject in need thereof by determining responsiveness of the subject to a combination therapy and when the subject is responsive to the combination therapy, administering to the subject a composition of the invention. The responsiveness is determined by obtaining a sample from the subject and detecting increased mRNA or protein, and/or increased activity level of at least one protein selected from the group consisting of HOXA9, FLT3, MEIS1 and DOT1L, and the presence of such gain of expression and/or function indicates that the subject is responsive to the composition of the invention. Once the responsiveness of a subject is determined, a therapeutically effective amount of a composition, for example, a composition comprising a compound of Formula (I) or pharmaceutically acceptable salts thereof, and one or more therapeutic agents, can be administered. The therapeutically effective amount of a composition can be determined by one of ordinary skill in the art.

As used herein, the term "responsiveness" is interchangeable with terms "responsive", "sensitive", and "sensitivity", and it is meant that a subject is showing therapeutic responses when administered a composition of the invention, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the invention, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

An increase in mRNA or protein expression and/or activity levels can be detected using any suitable method available in the art. For example, an increase in activity level can be detected by measuring the biological function of a gene product, such as the histone methyltransferase activity of DOT1L (i.e., methylation of histone substrates such as H3K79 by immunoblot); transcriptional activity of HOXA9 or MEIS1 (i.e., expression levels of HOXA9 or MEIS1 target genes by RT-PCR); or phosphorylation activity of FLT3 (i.e., phosphorylation status of FLT3 targets by immunoblot or radioimmunoassay). Alternatively, a gain of function mutation can be determined by detecting any alternation in a nucleic acid sequence encoding a protein selected from the group consisting of HOXA9, FLT3, MEIS1 and DOT1L. For example, a nucleic acid sequence encoding HOXA9, FLT3, MEIS1 and DOT1L having a gain of function mutation can be detected by whole-genome resequencing or target region resequencing (the latter also known as targeted resequencing) using suitably selected sources of DNA and polymerase chain reaction (PCR) primers in accordance with methods well known in the art. The method typically and generally entails the steps of genomic DNA purification, PCR amplification to amplify the region of interest, cycle sequencing, sequencing reaction cleanup, capillary electrophoresis, and/or data analysis. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Detection of mRNA expression can be detected by methods known in the art, such as Northern blot, nucleic acid PCR, and quantitative RT-PCR. Detection of polypeptide expression (i.e., wild-type or mutant) can be carried out with any suitable immunoassay in the art, such as Western blot analysis.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute lymphocytic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or T is; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph, or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

For example, an in vitro biological assay that can be used includes the steps of (1) mixing a histone substrate (e.g., an isolated histone sample for a histone or modified histone of interest, or an isolated oligonucleosome substrate) with recombinant DOT1L enzyme (e.g., recombinant protein containing amino acids 1-416); (2) adding a candidate compound of the invention to this mixture; (3) adding non-radioactive and $^3$H-labeled S-Adenosyl methionine (SAM) to start the reaction; (4) adding excessive amount of non-radioactive SAM to stop the reaction; (4) washing off the free non-incorporated $^3$H-SAM; and (5) detecting the quantity of $^3$H-labeled histone substrate by any methods known in the art (e.g., by a PerkinElmer TopCount platereader).

For example, an in vitro cell viability assay that can be used includes the steps of (1) culturing cells (e.g., EOL-1 cells) in the presence of increasing concentration of candidate compound (e.g., Compound A2, Compound D16); (2) determining viable cell number every 3-4 days by methods known in the art (e.g., using the Millipore Guava Viacount assay); (3) plotting concentration-dependence growth curves; and optionally (4) calculating $IC_{50}$ values from the concentration-dependence growth curves using methods known in the art (e.g., using GraphPad Prism Software).

For example, a histone methylation assay that can be used includes the steps of (1) culturing cells (e.g., EOL-1 cells) in the presence of candidate compound (e.g., Compound A2 or Compound D16); (2) harvesting the cells; (3) extracting histone proteins, using methods known in the art (e.g., sulfuric acid precipitation); (4) fractionating histone extracts by SDS-PAGE electrophoresis and transferring to a filter; (5) probing the filter with antibodies specific to a protein or methylated-protein of interest (e.g., H3K79me2-specific antibody and total histone H3-specific antibody); and (6) detecting the signal of the antibodies using methods known in the art (e.g., Li-cor Odyssey infrared imager).

For example, a gene expression assay that can be used includes the steps of (1) culturing cells (e.g., EOL-1, Molm13, MV411, LOUCY, SemK2, Reh, HL60, BV173, or Jurkat cells) in the presence or absence of candidate compound (e.g., Compound A2 or Compound D16); (2) harvesting the cells; (3) extracting the RNA using methods known in the art (e.g., Qiagen RNeasy Kit); (4) synthesizing cDNA from the extracted RNA (e.g., Applied Biosystems reverse transcriptase kit); (5) preparing qPCR reactions using, for example, primers and probes (e.g., predesigned labeled primer and probe sets for HOXA9, MEIS1, FLT3, DOT1L, and β2-microglobulin from Applied Biosystems), synthesized sample cDNA, and qPCR master mix reagent (e.g., Applied Biosystems Taqman universal PCR master mix); (6) running samples on PCR machine (e.g., Applied Biosystems); (7) analysis of the data and calculation of relative gene expression.

As used herein, "monotherapy" refers to the administration of a single active or therapeutic compound to a subject in need thereof. Preferably, monotherapy will involve administration of a therapeutically effective amount of a single active compound. For example, cancer monotherapy with one of the compound of the present invention, or a pharmaceutically acceptable salt, prodrug, metabolite, analog or derivative thereof, to a subject in need of treatment of cancer. In one aspect, the single active compound is a compound of the present invention, or a pharmaceutically acceptable salt, prodrug, metabolite, polymorph or solvate thereof.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the present invention e.g., a composition comprising a compound of Formula (I) or a pharmaceutically acceptable salt, prodrug, metabolite, polymorph or solvate thereof and one or more therapeutic agents, can modulate the activity of a molecular target (e.g., a target protein methyltransferase). Modulating refers to stimulating or inhibiting an activity of a molecular target. Preferably, a composition of the invention modulates the activity of a molecular target if it stimulates or inhibits the activity of the molecular target by at least 2-fold relative to the activity of the molecular target under the same conditions but lacking only the presence of said compound. More preferably, a composition of the present invention modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a composition of the present invention demonstrates a minimum of a fourfold differential, preferably a tenfold differential, more preferably a fifty fold differential, in the dosage required to achieve a biological effect. Preferably, a composition of the present invention demonstrates this differential across the range of inhibition, and the differential is exemplified at the $IC_{50}$, i.e., a 50% inhibition, for a molecular target of interest.

Administering a composition of the present invention to a cell or a subject in need thereof can result in modulation (i.e., stimulation or inhibition) of an activity of a protein methyltransferase of interest. Several intracellular targets can be modulated with the compounds of the present invention, including, but not limited to, protein methyltransferase.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a composition of the present invention is not significantly cytotoxic to normal cells. A therapeutically effective amount of a composition is not significantly cytotoxic to normal cells if administration of the composition in a therapeutically effective amount does not induce cell death in greater than 10% of normal cells. A therapeutically effective amount of a composition does not significantly affect the viability of normal cells if administration of the composition in a therapeutically effective amount does not induce cell death in greater than 10% of normal cells. In an aspect, cell death occurs by apoptosis.

Contacting a cell with a composition of the invention can induce or activate cell death selectively in cancer cells. Administering to a subject in need thereof a composition of the present invention can induce or activate cell death selectively in cancer cells. Contacting a cell with a composition of the present invention can induce cell death selectively in one or more cells affected by a cell proliferative disorder. Preferably, administering to a subject in need thereof a composition of the present invention induces cell death selectively in one or more cells affected by a cell proliferative disorder.

The present invention relates to a method of treating or alleviating a symptom of cancer by administering a composition of the present invention to a subject in need thereof, where administration of the composition results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., 18$^{th}$ edition (1990). These texts can, of course, also be referred to in making or using an aspect of the invention The composition of the instant invention can also be utilized to treat or alleviate a symptom of neurologic diseases or disorders. Neurologic diseases or disorders that may be treated with the compounds of this invention include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCAT), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by DOT1, plays a role may be treatable or preventable using compounds and methods described herein.

The present invention provides use of a composition disclosed herein for inhibiting DOT1L activity in a cell. Still another aspect of the invention relates to a use of a composition disclosed herein for reducing the level of methylation of histone H3 lysine residue 79 (H3-K79) in a cell.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1

DOT1L Combination Studies in MLL-Rearranged Cell Lines

Methods

The acute myelogenous leukemia cell lines MV4-11 (MLL-AF4) and MOLM-13 (MLL-AF9) were obtained from American Type Culture Collection (ATCC; Rockville, Md.) and Deutsche Sammlung von Mikroorganismen and Zellkulturen (DSMZ; Braunschweig, Germany) respectively. MV4-11 cells were maintained in IMDM (Invitrogen, supplemented with 10% heat inactivated fetal bovine serum (Life Technologies, Grand Island, N.Y.). MOLM-13 cells were maintained in RPMI-1640 supplemented with 10% fetal bovine serum (Life Technologies, Grand Island, N.Y.). Cultures were maintained in a humidified atmosphere including 5% $CO_2$.

Studies were performed using MLL-rearranged cell lines in vitro to evaluate the anti-proliferative effect of a combination of two agents together on cell growth. Initial proliferation studies were performed to determine the $IC_{50}$ of a given compound in each cell line. The cell counts were measured by ATP quantitation using the Promega Cell Titer Glo kit and luminescence values corresponded to the amount of ATP in a given well.

Figure 2:
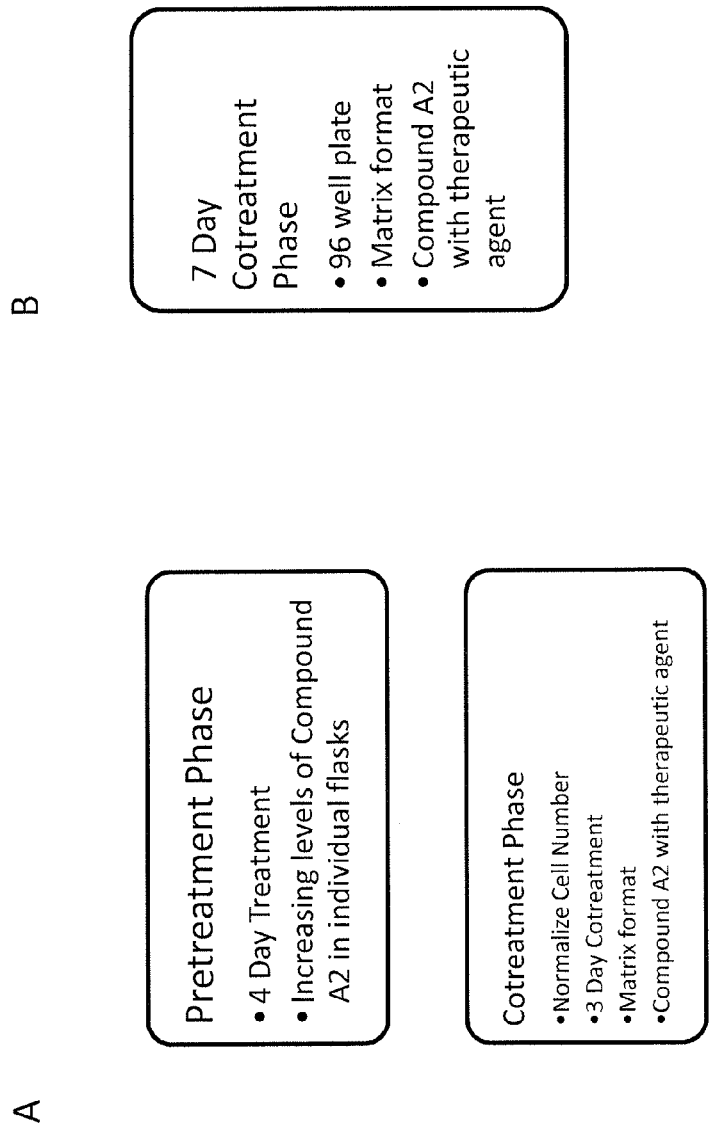
FIG. 2 is a series of diagrams showing the steps of (A) 4-day+3-day ("4+3") treatment experimental design and (B) 7-day treatment experimental design.

Compounds were tested in combination with Compound A2 to study their effect on cell proliferation in either a 4+3 model (cells were pretreated with increasing concentrations of Compound A2 for 4 days, followed by a co-treatment with Compound A2 with test article for 3 days) or a 7 day co-treatment model (FIGS. 1 and 2).

Results

Figure 3:
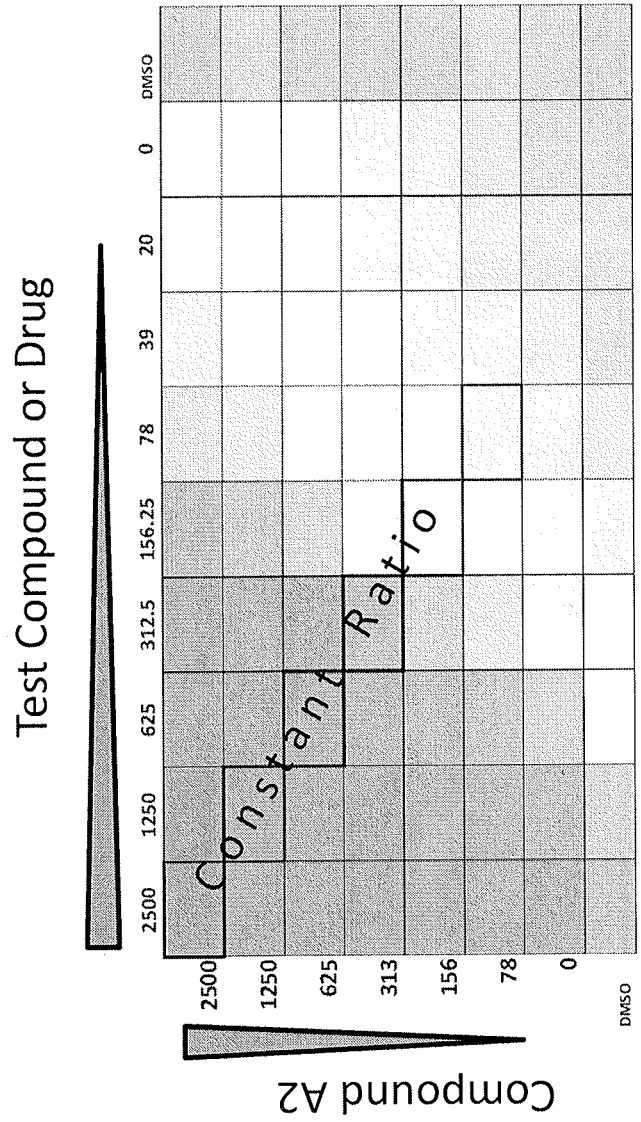
FIG. 3 is diagram showing the experimental design about dosing of the compounds.

Compounds were evaluated for synergy in the co-treatment phase by testing the compounds in a concentration range which was bracketed around their $IC_{50}$ values. The compounds were plated to a 96 well plate in a matrix format (FIG. 3) which includes increasing concentrations of each drug in the combination in a constant ratio, in addition to the effect of each compound alone in the study. Cells were seeded and grown in the log-linear phase for 3 or 7 days in the co-treatment phase. Minimum inhibition (DMSO alone) controls were used in each plate to calculate fraction affected (Fa) of a test well. DMSO concentration was kept at 0.1% v/v.

The drug combination analysis was performed utilizing the Chou-Talalay method (Ref 1). Synergy was determined using the software package Calcusyn by Biosoft. The combination index (CI) is a quantitative term used to describe the level of synergy or antagonism in a given test system. A combination index less than one indicates synergy, and a CI greater than one indicates antagonism. Further, strong synergism is achieved when the CI value falls below 0.3.

Figure 4:
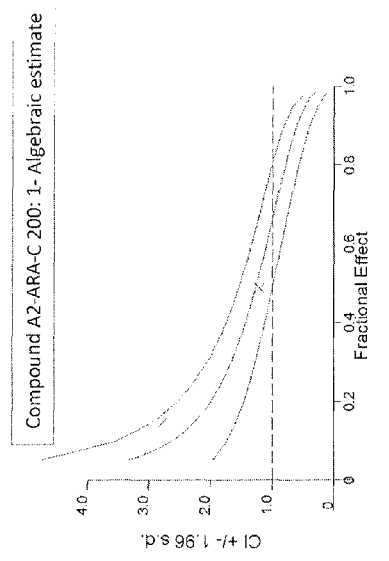
FIG. 4 is a series of graphs showing combination index (CI) values for combinations of Compound A2 and Ara-C in (A) 4+3 and (B) 7-day treatment experiments in MOLM-13 cell line.
Figure 4:
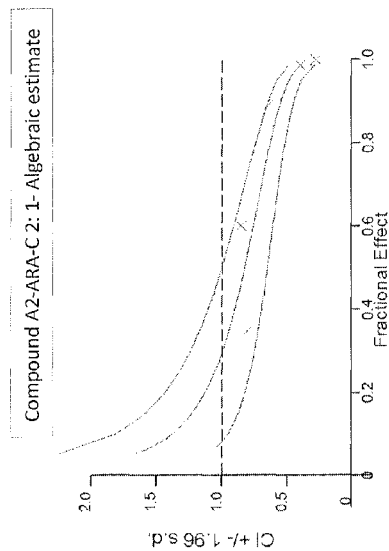
Figure 5:
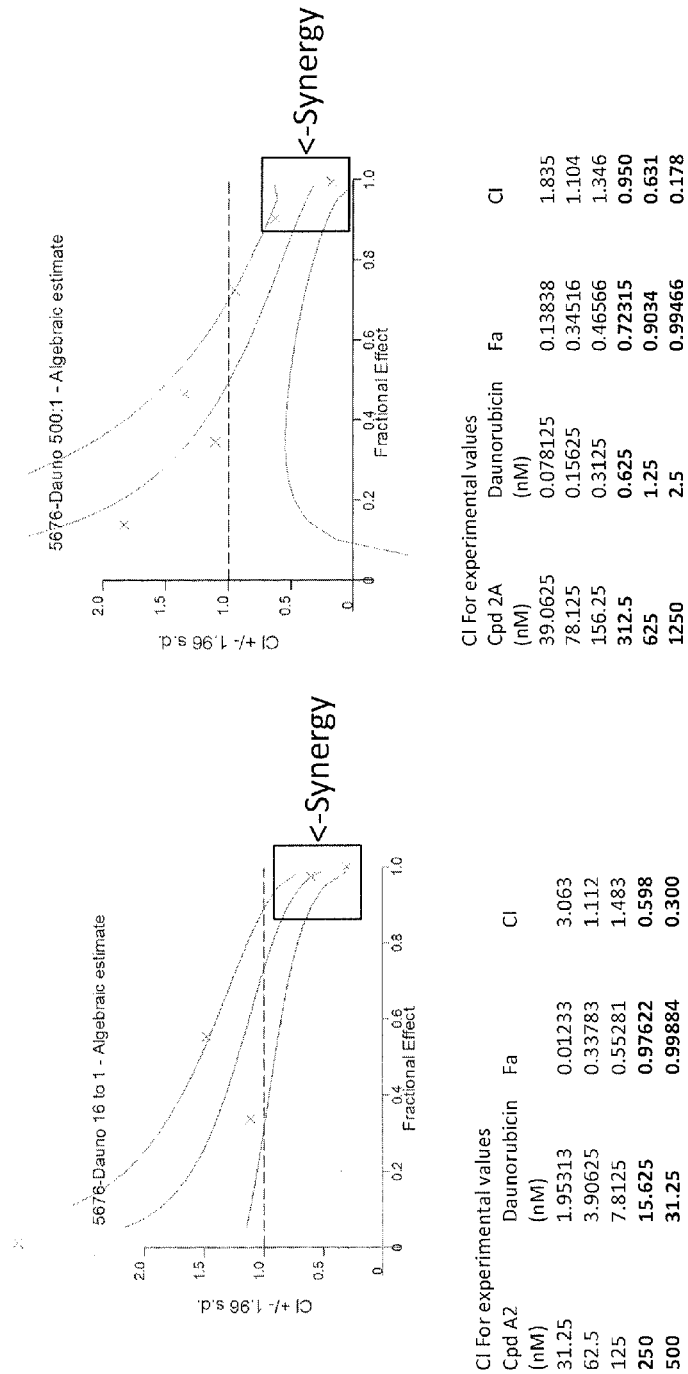
FIG. 5 is a series of graphs showing combination index (CI) values for combinations of Compound A2 and Daunorubicin in (A) 4+3 and (B) 7-day treatment experiments in MOLM-13 cell line.
Figure 6:
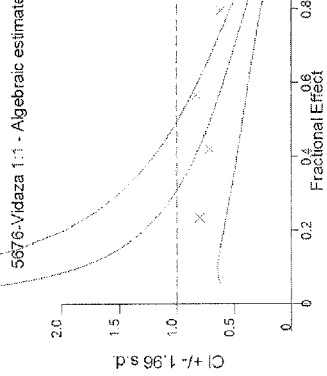
FIG. 6 is a series of graphs showing combination index (CI) values for combinations of Compound A2 and hypomethylating agents (A) Decitabine and (B) Vidaza in a 7-day treatment experiment in MOLM-13 cell line.
Figure 6:
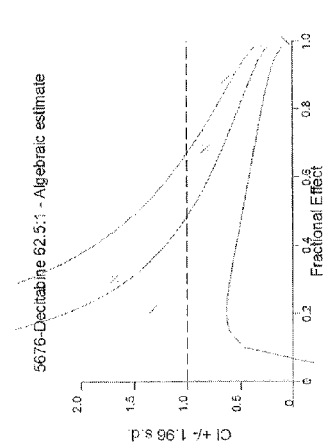
Figure 7:
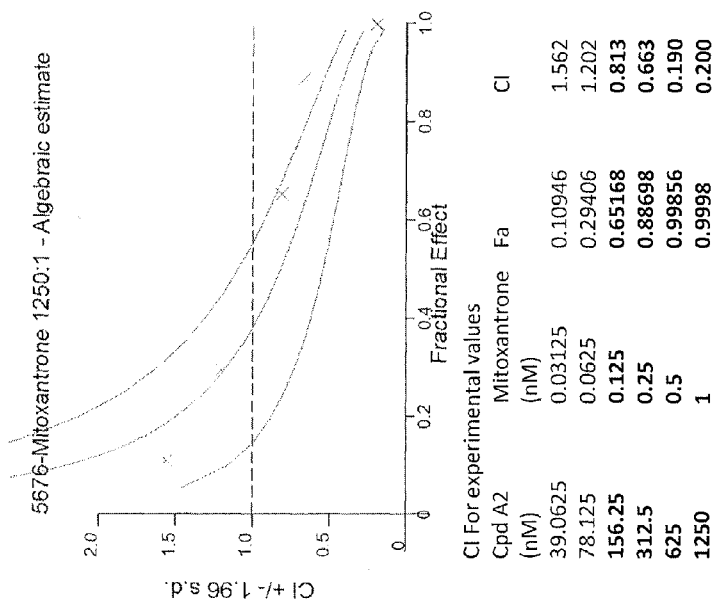
FIG. 7 is a graph showing combination index (CI) values for combinations of Compound A2 and topoisomerase inhibitor, Mitoxantrone, in MOLM-13 cell line.
Figure 8:
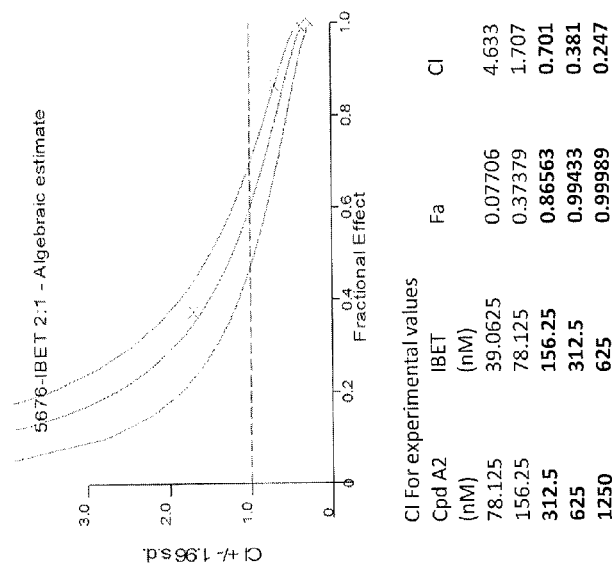
FIG. 8 is a graph showing combination index (CI) values for combinations of Compound A2 and Bromodomain inhibitor, IBET-151, in a 7-day treatment experiment in MOLM-13 cell line.
Figure 9:
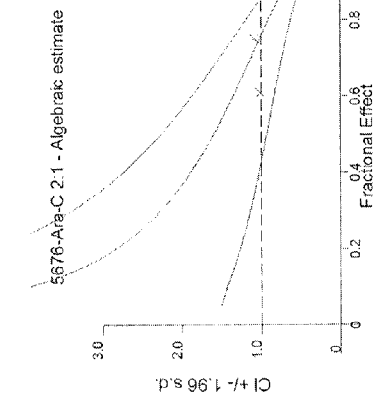
FIG. 9 is a series of graphs showing combination index (CI) values for combinations of Compound A2 and Ara-C in (A) 4+3 and (B) 7-day treatment experiments in MV4-11 cell line.
Figure 9:
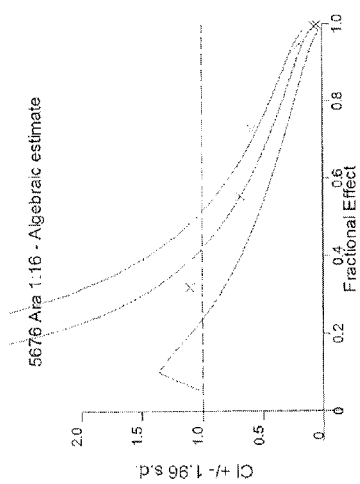
Figure 10:
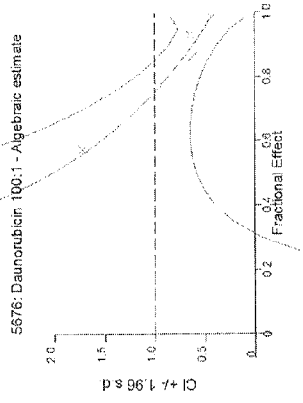
FIG. 10 is a series of graphs showing combination index (CI) values for combinations of Compound A2 and Daunorubicin in (A) 4+3 and (B) 7-day treatment experiments in MV4-11 cell line.
Figure 10:
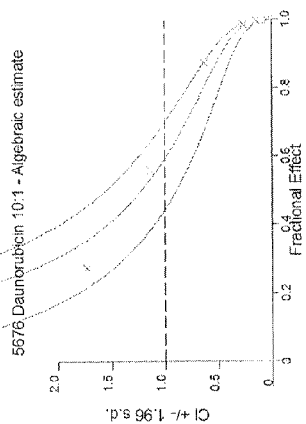
Figure 11:
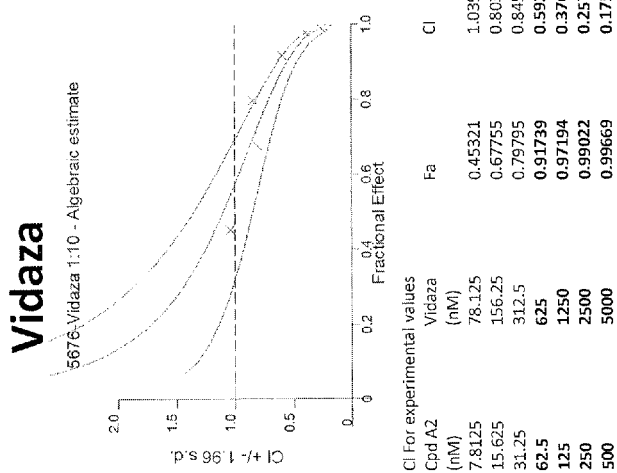
FIG. 11 is a graph showing combination index (CI) values for combinations of Compound A2 and Vidaza in MV4-11 cell line.
Figure 12:
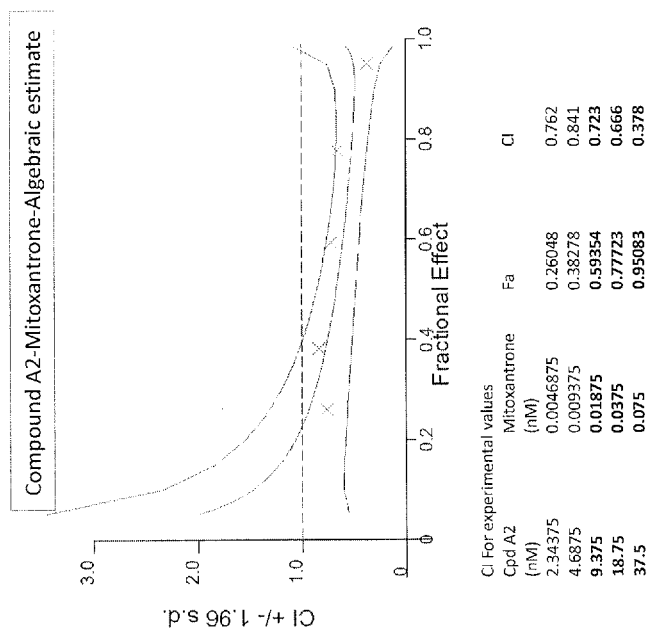
FIG. 12 is a graph showing combination index (CI) values for combinations of Compound A2 and topoisomerase inhibitor, Mitoxantrone, in MV4-11 cell line.
Figure 13:
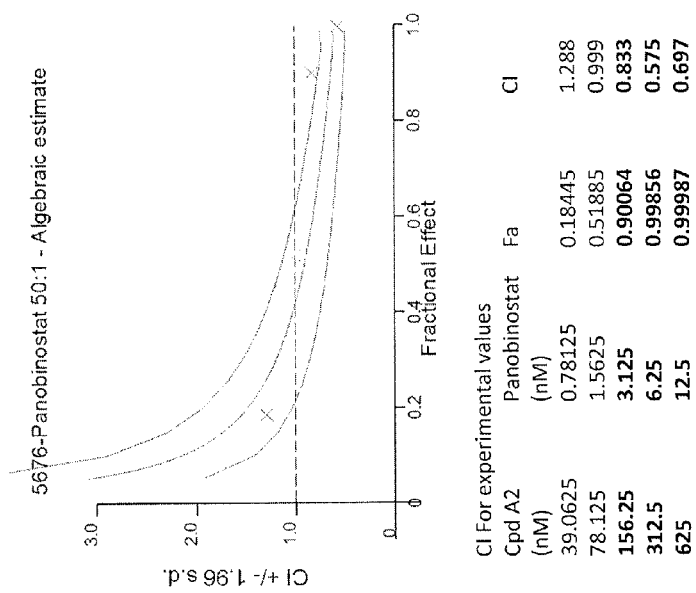
FIG. 13 is a graph showing combination index (CI) values for combinations of Compound A2 and HDAC inhibitor, Panobinostat, in MV4-11 cell line.
Figure 14:
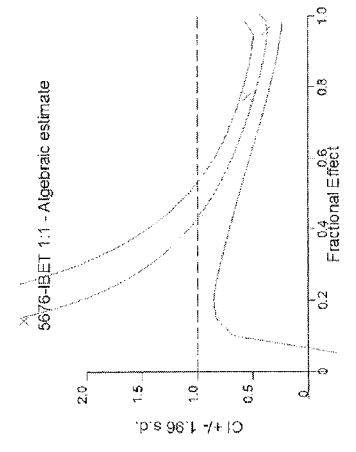
FIG. 14 is a series of graphs showing combination index (CI) values for combinations of Compound A2 and IBET-151 in (A) 4+3 and (B) 7-day treatment experiments in MV4-11 cell line.
Figure 14:
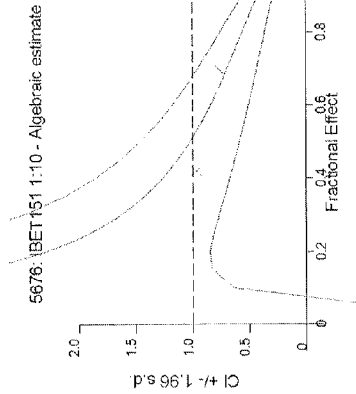

Pretreatment with Compound A2 followed by cotreatment with either Ara-C or Daunorubicin demonstrated synergy in both MV4-11 and MOLM-13 cell lines. In a seven day cotreatment model, synergy with Compound A2 has been shown with the following drugs in the MOLM-13 (MLL-AF9 rearranged) cell line: Ara-C (FIG. 4), Daunorubicin (FIG. 5) Decitabine (strong) (FIG. 6), Vidaza (strong) (FIG. 6), Mitoxantrone (FIG. 7), IBET-151 (FIG. 8). Synergy with Compound A2 has been shown with the following drugs in MV4-11 (MLL-AF4) cell line: Ara-C (FIG. 9), Daunorubicin (FIG. 10), Vidaza (FIG. 11), Mitoxantrone (FIG. 12), IBET-151 (FIG. 14).

Figure 15:
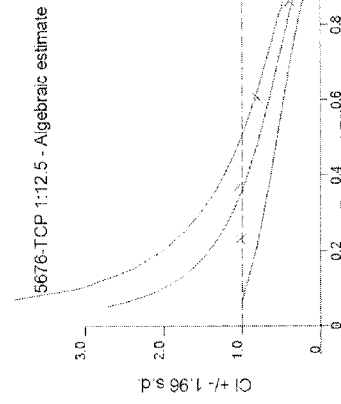
FIG. 15 is a series of graphs showing combination index (CI) values for combinations of Compound A2 and Tranylcypromine in a 7-day treatment experiment in (A) MOLM-13 cell line and (B) MV4-11 cell line.
Figure 15:
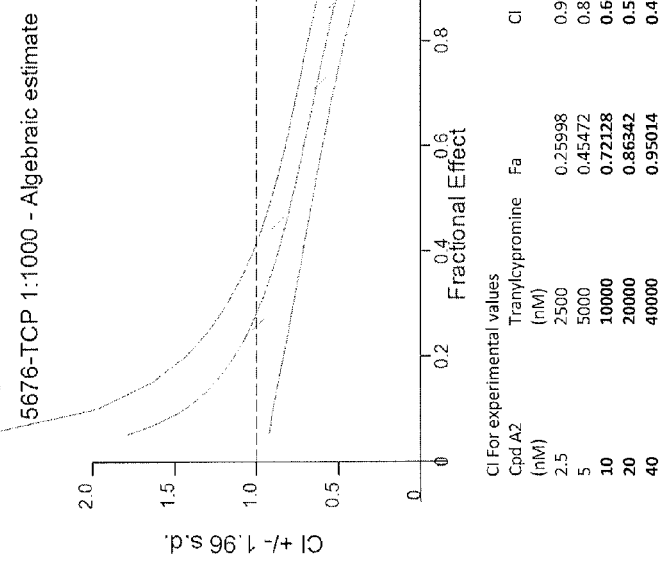
Figure 16:
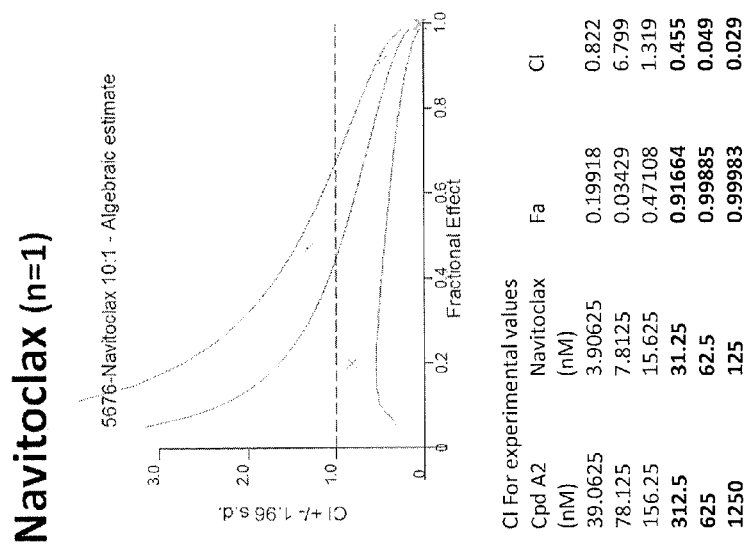
FIG. 16 is a series of graphs showing combination index (CI) values for combinations of Compound A2 and Bcl-2 inhibitor, Navitoclax, in (A) a 7-day treatment experiment in MOLM-13 cell line; (B) a 4+3 treatment experiment in MV4-11 cell line; and (C) a 7-day treatment experiment MV4-11 cell line.
Figure 16:
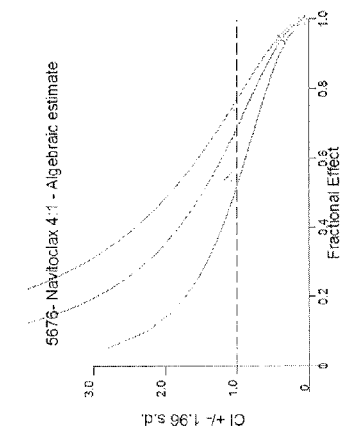
Figure 16:
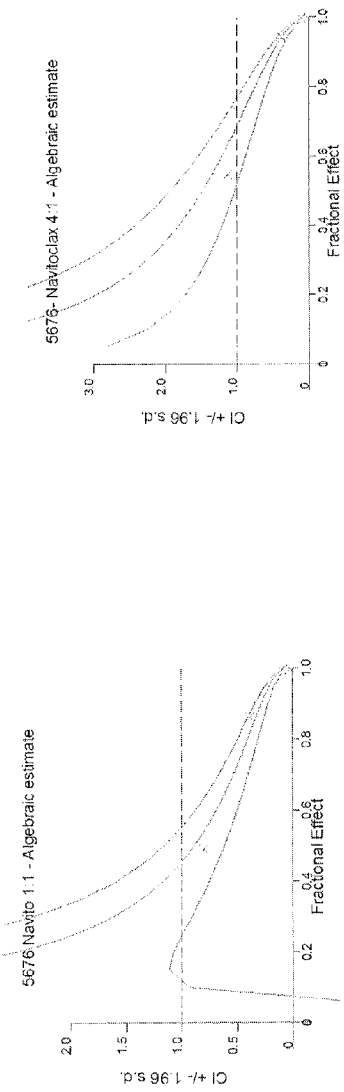
Figure 17:
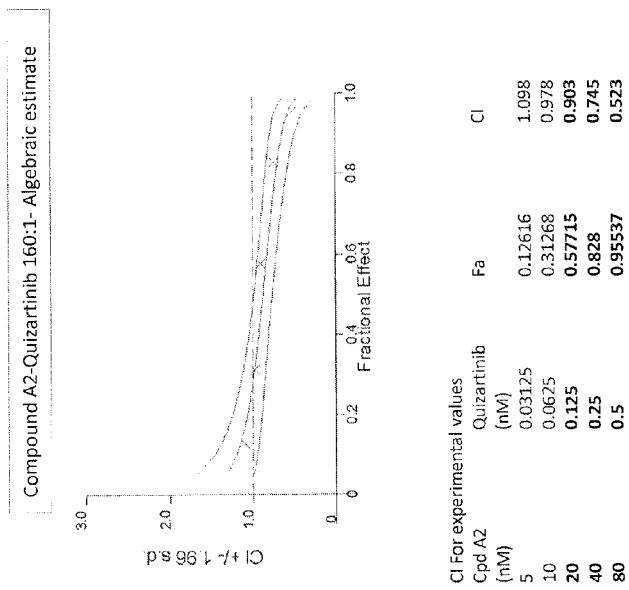
FIG. 17 is a graph showing combination index (CI) values for combinations of Compound A2 and FLT inhibitor, Quizartinib, in a 7-day treatment experiment in MV4-11 cell line.

To this end, it has been demonstrated that LSD1 inhibitor, Tranylcypromine (FIG. 15) and Bcl-2 inhibitor, Navitoclax (FIG. 16) show synergy with Compound A2 in both MOLM (FIGS. 15 and 16) and MV4-11 cell lines (FIGS. 15 and 16). Quizartinib (FIG. 17), a FLT inhibitor has also shown synergy in MV4-11 cells.

TABLE 5

Summary table for combination studies of Compound A2 and exemplary anti-cancer agents.

|  |  | MOLM-13 | MV4-11 |
|---|---|---|---|
| 4 + 3 Model |  Ara-C | Synergy | Synergy |
|  | Daunorubicin | Synergy | Synergy |
| 7 Day | Ara-C | Synergy | Synergy |
| Cotreatment | Daunorubicin | Synergy | Synergy |
|  | Decitabine | Strong Synergy | Additive (no data shown) |
|  | Vidaza | Strong Synergy | Synergy |
|  | Mitoxantrone | Synergy | Synergy |
|  | IBET-151 | Synergy | Synergy |

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A composition comprising Compound A2:

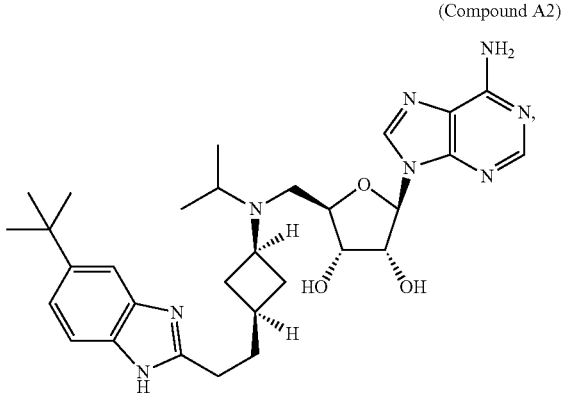 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(Compound A2)

or a pharmaceutically acceptable salt thereof, and one or more therapeutic agents selected from MAP/MEK inhibitors, ara-C, daunorubicin, decitabine, azacitidine, mitoxantrone, IBET151, quizartinib, midostaurin, tranylcypromine, navitoclax, and a combination thereof.

2. The composition of claim 1, wherein the one or more therapeutic agents are MAP/MEK inhibitors.

3. The composition of claim 1, wherein the one or more therapeutic agents are selected from ara-C, daunorubicin, decitabine, azacitidine, mitoxantrone, IBET151, quizartinib, midostaurin, tranylcypromine, navitoclax, and combinations thereof.

4. The composition of claim 1, wherein the one or more therapeutic agents are ara-C, daunorubicin, or selumetinib (AZD-6244).

5. A pharmaceutical composition comprising a therapeutically effective amount of composition of claim 1 and a pharmaceutically acceptable carrier.

6. A method of treating cancer or a precancerous condition comprising administering to a subject in need thereof a therapeutically effective amount of a composition of claim 1.

7. The method of claim 6, wherein the cancer or the precancerous condition can be influenced by modulating the methylation status of histones or other proteins.

8. The method of claim 7, wherein the methylation status is mediated at least in part by the activity of DOT1L.

9. A method of treating or alleviating a symptom of cancer comprising administering to a subject in need thereof a therapeutically effective dose of Compound A2:

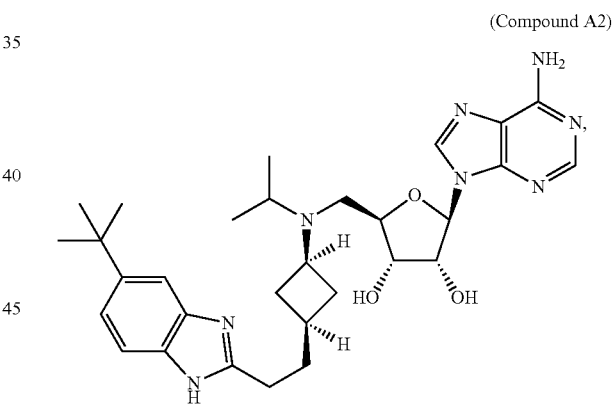

(Compound A2)

or a pharmaceutically acceptable salt thereof and one or more therapeutic agents selected from MAP/MEK inhibitors, ara-C, daunorubicin, decitabine, azacitidine, mitoxantrone, IBET151, quizartinib, midostaurin, tranylcypromine, navitoclax, and a combination thereof, wherein Compound A2 or a pharmaceutically acceptable salt thereof and the one or more therapeutic agents are administered simultaneously or sequentially.

10. The method of claim 9, wherein Compound A2 or a pharmaceutically acceptable salt thereof is administered prior to administration of the one or more therapeutic agents.

11. A method of treating or alleviating a symptom of cancer comprising administering to a subject in need thereof a therapeutically effective dose of Compound A2:

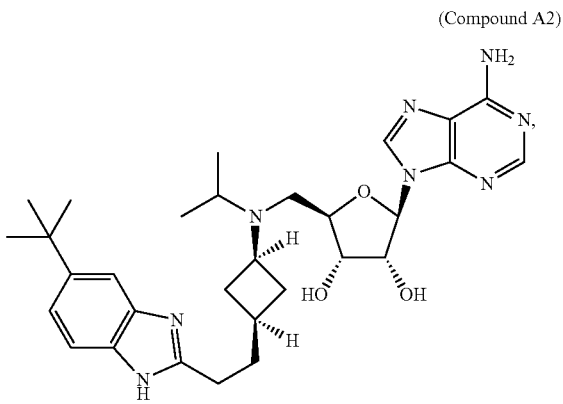 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]
(Compound A2)

or a pharmaceutically acceptable salt thereof, prior to administering a therapeutically effective dose of a composition of claim 1.

12. The method of claim 6, wherein the composition of claim 1 is administered to the subject in need thereof at a dosage of 0.01 mg/kg per day to about 1000 mg/kg per day.

13. The method of claim 9, wherein Compound A2 or a pharmaceutically acceptable salt thereof is administered at a dosage of 0.01 mg/kg per day to about 1000 mg/kg per day.

14. The method of claim 9, wherein each of the one or more therapeutic agents is administered at a dosage of 0.01 mg/kg per day to about 1000 mg/kg per day.

15. The method of claim 6, wherein the subject has demonstrated resistance to any one of the components of the composition of claim 1 when administered as a single agent.

16. The method of claim 6, wherein the one or more therapeutic agents are ara-C, daunorubicin, or selumetinib (AZD-6244).

17. The method of claim 6, wherein the subject has leukemia.

18. The method of claim 17, wherein the leukemia is characterized by a chromosomal rearrangement.

19. The method of claim 18, wherein the chromosomal rearrangement is chimeric fusion of mixed lineage leukemia gene (MLL) or partial tandem duplication of MLL (MLL-PTD).

20. The method of claim 6, wherein the subject has an increased level of HOXA9, Fms-like tyrosine kinase 3 (FLT3), MEIS1, and/or DOT1L.

21. The method of claim 11, wherein the composition of claim 1 is administered to the subject in need thereof at a dosage of 0.01 mg/kg per day to about 1000 mg/kg per day.

22. The method of claim 11, wherein Compound A2 or a pharmaceutically acceptable salt thereof is administered at a dosage of 0.01 mg/kg per day to about 1000 mg/kg per day.

23. The method of claim 11, wherein each of the one or more therapeutic agents is administered at a dosage of 0.01 mg/kg per day to about 1000 mg/kg per day.

* * * * *